(12) United States Patent
Naga et al.

(10) Patent No.: US 12,364,792 B2
(45) Date of Patent: Jul. 22, 2025

(54) DEVICES, SYSTEMS, AND METHODS FOR TREATING INTRALUMINAL CANCER VIA CONTROLLED DELIVERY OF THERAPEUTIC AGENTS

(71) Applicant: Foundry Therapeutics, Inc., Menlo Park, CA (US)

(72) Inventors: Karun D. Naga, Los Altos, CA (US); Stephen W. Boyd, San Francisco, CA (US); Hanson S. Gifford, III, Woodside, CA (US); Mark Deem, Portola Valley, CA (US); John Morriss, Emerald Hills, CA (US); Martin Mayse, Wayzata, MN (US); Honglei Wang, Singapore (SG); Jingnan Luo, Singapore (SG); Daniel Boon Lim Seet, Singapore (SG); Koon Kiat Teu, Singapore (SG); Wei Li Lee, Singapore (SG)

(73) Assignee: Foundry Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 16/960,524

(22) PCT Filed: Jan. 8, 2019

(86) PCT No.: PCT/US2019/012795
§ 371 (c)(1),
(2) Date: Jul. 7, 2020

(87) PCT Pub. No.: WO2019/136490
PCT Pub. Date: Jul. 11, 2019

(65) Prior Publication Data
US 2020/0368398 A1 Nov. 26, 2020

Related U.S. Application Data

(60) Provisional application No. 62/614,884, filed on Jan. 8, 2018.

(30) Foreign Application Priority Data

Oct. 6, 2018 (WO) ................. PCT/US18/54777

(51) Int. Cl.
| | |
|---|---|
| *A61L 27/58* | (2006.01) |
| *A61L 27/54* | (2006.01) |
| *A61L 31/10* | (2006.01) |
| *A61L 31/14* | (2006.01) |
| *A61L 31/16* | (2006.01) |

(52) U.S. Cl.
CPC ............ *A61L 27/58* (2013.01); *A61L 27/54* (2013.01); *A61L 31/10* (2013.01); *A61L 31/148* (2013.01); *A61L 31/16* (2013.01); *A61L 2300/416* (2013.01)

(58) Field of Classification Search
None
See application file for complete search history.

(56) References Cited

U.S. PATENT DOCUMENTS

| | | | |
|---|---|---|---|
| 4,601,893 | A | 7/1986 | Cardinal |
| 4,666,704 | A | 5/1987 | Shalati et al. |
| 4,919,939 | A | 4/1990 | Baker |
| 5,227,165 | A | 7/1993 | Domb et al. |
| 5,451,408 | A | 9/1995 | Mezei et al. |
| 5,458,582 | A | 10/1995 | Nakao |
| 5,540,912 | A | 7/1996 | Roorda et al. |
| 5,618,563 | A | 4/1997 | Berde et al. |
| 5,667,523 | A * | 9/1997 | Bynon ............ A61F 2/91 606/198 |
| 5,700,485 | A | 12/1997 | Berde et al. |

(Continued)

FOREIGN PATENT DOCUMENTS

| | | |
|---|---|---|
| AU | 2012201226 B2 | 8/2014 |
| AU | 2013200515 B2 | 1/2016 |

(Continued)

OTHER PUBLICATIONS

Guo et al. Journal of Controlled Release 2007 118:318-324 (Year: 2007).*
Yuan et al. Materials 2016 9(384):1-11 (Year: 2016).*
Tallury et al. Dental Materials 2007 23:977-982 (Year: 2007).*
Goindi et al. AAPS PharmSciTech 2014 15(4):810-821 (Year: 2014).*
Chun et al. Journal of Gastroenterology and Hepatology 2010 25:234-243 (Year: 2010).*
Lee et al. International Journal of Pharmaceutics 2012 427:276-283 (Year: 2012).*

(Continued)

*Primary Examiner* — Melissa S Mercier
*Assistant Examiner* — Caralynne E Helm
(74) *Attorney, Agent, or Firm* — Fortem IP LLP

(57) ABSTRACT

The devices, systems, and methods disclosed herein may be directed to a delivery system including a therapeutic member configured for endoluminal placement via the delivery system into the esophagus of the patient, wherein the therapeutic member comprises a treatment portion comprising a film for controlled release of a chemotherapeutic agent. The film may comprise a control region, a therapeutic region, and a substantially impermeable base region. The film is configured to release the chemotherapeutic agent in a direction away from the substantially impermeable base region. The delivery system is configured to enable a treatment provider to position the treatment portion of the therapeutic member proximate to a treatment site associated with the esophagus of the patient, and the therapeutic member is configured to administer a therapeutically effective dose to the treatment site for a sustained period following endoluminal placement of the therapeutic member.

5 Claims, 44 Drawing Sheets

(56) References Cited

U.S. PATENT DOCUMENTS

| | | |
|---|---|---|
| 5,747,060 A | 5/1998 | Sackler et al. |
| 5,807,306 A * | 9/1998 | Shapland ............... A61N 1/325 |
| | | 604/21 |
| 5,919,473 A | 7/1999 | Elkhoury |
| 5,931,809 A | 8/1999 | Gruber et al. |
| 5,942,241 A | 8/1999 | Chasin et al. |
| 6,046,187 A | 4/2000 | Berde et al. |
| 6,149,937 A | 11/2000 | Camu et al. |
| 6,214,387 B1 | 4/2001 | Berde et al. |
| 6,248,345 B1 | 6/2001 | Goldenheim et al. |
| 6,326,020 B1 | 12/2001 | Kohane et al. |
| 6,451,335 B1 | 9/2002 | Goldenheim et al. |
| 6,699,908 B2 | 3/2004 | Sackler et al. |
| 6,913,760 B2 | 7/2005 | Carr et al. |
| 7,074,426 B2 | 7/2006 | Kochinke |
| 7,220,433 B2 | 5/2007 | Cui et al. |
| 7,723,291 B2 | 5/2010 | Beals et al. |
| 7,727,954 B2 | 6/2010 | Mckay |
| 7,741,273 B2 | 6/2010 | Mckay |
| 7,824,703 B2 | 11/2010 | Scifert et al. |
| 7,947,301 B2 | 5/2011 | Bischoff et al. |
| 7,993,390 B2 | 8/2011 | Miller et al. |
| 8,067,026 B2 | 11/2011 | Ranade et al. |
| 8,080,059 B2 | 12/2011 | Fell |
| 8,153,149 B2 | 4/2012 | Verity |
| 8,202,531 B2 | 6/2012 | Mckay |
| 8,221,358 B2 | 7/2012 | Mckay |
| 8,231,891 B2 | 7/2012 | King |
| 8,246,571 B2 | 8/2012 | Simonton et al. |
| 8,257,393 B2 | 9/2012 | Cichocki |
| 8,357,388 B2 | 1/2013 | Mckay |
| 8,420,600 B2 | 4/2013 | Burch et al. |
| 8,430,852 B2 | 4/2013 | Bischoff et al. |
| 8,470,360 B2 | 6/2013 | Mckay |
| 8,523,569 B2 | 9/2013 | Neshat |
| 8,524,267 B2 | 9/2013 | Zanella et al. |
| 8,575,092 B2 | 11/2013 | Domb |
| 8,591,531 B2 | 11/2013 | Buevich et al. |
| 8,603,528 B2 | 12/2013 | Kronenthal |
| 8,623,396 B2 | 1/2014 | Gray et al. |
| 8,629,172 B2 | 1/2014 | Mckay et al. |
| 8,632,839 B2 | 1/2014 | Stopek et al. |
| 8,652,504 B2 | 2/2014 | Li et al. |
| 8,652,525 B2 | 2/2014 | Moses et al. |
| 8,663,192 B2 | 3/2014 | Hester et al. |
| 8,697,117 B2 | 4/2014 | Zilberman |
| 8,703,119 B2 | 4/2014 | Yankelson et al. |
| 8,708,966 B2 | 4/2014 | Allen et al. |
| 8,715,223 B2 | 5/2014 | Mckay |
| 8,728,493 B2 | 5/2014 | Burton et al. |
| 8,728,509 B2 | 5/2014 | Mckay |
| 8,750,983 B2 | 6/2014 | Bonutti |
| 8,758,798 B2 | 6/2014 | Stopek et al. |
| 8,795,713 B2 | 8/2014 | Makower et al. |
| 8,809,530 B1 | 8/2014 | Wu et al. |
| 8,822,492 B2 | 9/2014 | Schachter |
| 8,846,068 B2 | 9/2014 | Wohabrebbi et al. |
| 8,865,205 B2 | 10/2014 | Shalaby |
| 8,877,226 B2 | 11/2014 | Zanella et al. |
| 8,889,173 B2 | 11/2014 | Zanella et al. |
| 8,900,620 B2 | 12/2014 | Fulmer et al. |
| 8,911,765 B2 | 12/2014 | Moses et al. |
| 8,920,867 B2 | 12/2014 | Stopek et al. |
| 8,951,552 B2 | 2/2015 | Shalaby et al. |
| 8,956,642 B2 | 2/2015 | Hobot et al. |
| 8,968,767 B2 | 3/2015 | Mckay |
| 8,969,397 B2 | 3/2015 | Burright et al. |
| 8,980,317 B2 | 3/2015 | King |
| 8,999,368 B2 | 4/2015 | Mcdonald et al. |
| 9,005,634 B2 | 4/2015 | Mcdonald et al. |
| 9,011,965 B2 | 4/2015 | Gan et al. |
| 9,023,114 B2 | 5/2015 | Buevich et al. |
| 9,125,814 B2 | 9/2015 | He et al. |
| 9,125,917 B2 | 9/2015 | Mckay et al. |
| 9,132,087 B2 | 9/2015 | Lichter et al. |
| 9,132,194 B2 | 9/2015 | Mckay |
| 9,155,707 B2 | 10/2015 | Ying et al. |
| 9,161,903 B2 | 10/2015 | Drapeau et al. |
| 9,173,732 B2 | 11/2015 | Langer et al. |
| 9,198,758 B2 | 12/2015 | Mckay |
| 9,205,052 B2 | 12/2015 | Kim et al. |
| 9,211,285 B2 | 12/2015 | Mckay et al. |
| 9,265,733 B2 | 2/2016 | Mckay |
| 9,283,283 B2 | 3/2016 | Giammona et al. |
| 9,289,409 B2 | 3/2016 | Zanella et al. |
| 9,295,462 B2 | 3/2016 | Choy et al. |
| 9,302,903 B2 | 4/2016 | Park et al. |
| 9,320,708 B2 | 4/2016 | Scifert et al. |
| 9,351,924 B2 | 5/2016 | Cho et al. |
| 9,352,137 B2 | 5/2016 | Simonton et al. |
| 9,358,223 B2 | 6/2016 | King |
| 9,375,420 B2 | 6/2016 | King |
| 9,402,918 B2 | 8/2016 | Koyakutty et al. |
| 9,402,973 B2 | 8/2016 | Phillips et al. |
| 9,457,176 B2 | 10/2016 | Lee et al. |
| 9,504,749 B2 | 11/2016 | Mckay |
| 9,522,113 B2 | 12/2016 | Spada et al. |
| 9,549,920 B2 | 1/2017 | Wohabrebbi et al. |
| 9,566,241 B2 | 2/2017 | Ravis et al. |
| 9,597,132 B2 | 3/2017 | Houff |
| 9,610,194 B2 | 4/2017 | De Juan et al. |
| 9,610,243 B2 | 4/2017 | Clay et al. |
| 9,623,222 B2 | 4/2017 | Mckay |
| 9,629,818 B2 | 4/2017 | Nadkarni et al. |
| 9,655,994 B2 | 5/2017 | Mckay |
| 9,668,974 B2 | 6/2017 | Amselem et al. |
| 9,669,117 B2 | 6/2017 | Campbell et al. |
| 9,694,079 B2 | 7/2017 | Ottoboni et al. |
| 9,700,567 B2 | 7/2017 | Zanella et al. |
| 9,724,300 B2 | 8/2017 | Yamashita et al. |
| 9,764,066 B2 | 9/2017 | Sim et al. |
| 9,821,091 B2 | 11/2017 | Hossainy et al. |
| 9,833,548 B2 | 12/2017 | Mckay et al. |
| 9,861,590 B2 | 1/2018 | Stopek et al. |
| 9,987,233 B2 | 6/2018 | Helliwell et al. |
| 11,202,754 B2 | 12/2021 | Naga et al. |
| 11,224,570 B2 | 1/2022 | Naga et al. |
| 11,964,076 B2 | 4/2024 | Wang et al. |
| 11,969,500 B2 | 4/2024 | Naga et al. |
| 2001/0044651 A1 | 11/2001 | Steinke et al. |
| 2001/0055607 A1 | 12/2001 | Levin |
| 2002/0106410 A1 | 8/2002 | Masters |
| 2003/0022876 A1 | 1/2003 | Ashton et al. |
| 2003/0036803 A1 | 2/2003 | Mcghan |
| 2003/0074055 A1 * | 4/2003 | Haverkost ............... A61F 2/07 |
| | | 623/1.36 |
| 2003/0118649 A1 | 6/2003 | Gao et al. |
| 2003/0152637 A1 | 8/2003 | Chasin et al. |
| 2003/0157162 A1 | 8/2003 | Krugner-Higby et al. |
| 2003/0190341 A1 | 10/2003 | Shalaby et al. |
| 2003/0215496 A1 | 11/2003 | Patel et al. |
| 2004/0109893 A1 | 6/2004 | Chen et al. |
| 2004/0249441 A1 | 12/2004 | Miller et al. |
| 2005/0019404 A1 * | 1/2005 | Sung ....................... A61L 31/10 |
| | | 424/468 |
| 2005/0043786 A1 * | 2/2005 | Chu ......................... A61F 2/88 |
| | | 623/1.42 |
| 2005/0048115 A1 | 3/2005 | Mangena et al. |
| 2005/0152957 A1 | 7/2005 | Cleary et al. |
| 2005/0158382 A1 | 7/2005 | Cruz et al. |
| 2005/0206048 A1 | 9/2005 | Ryu et al. |
| 2005/0266077 A1 | 12/2005 | Royer |
| 2006/0034887 A1 | 2/2006 | Pelissier |
| 2006/0052823 A1 | 3/2006 | Mirizzi et al. |
| 2006/0079558 A1 | 4/2006 | Aberg et al. |
| 2006/0079559 A1 | 4/2006 | Aberg et al. |
| 2006/0269475 A1 | 11/2006 | Ryu et al. |
| 2007/0071790 A1 | 3/2007 | Ameer et al. |
| 2007/0134292 A1 | 6/2007 | Suokas et al. |
| 2007/0173787 A1 | 7/2007 | Huang et al. |
| 2007/0178138 A1 | 8/2007 | Pal et al. |
| 2007/0258939 A1 | 11/2007 | Lewis et al. |
| 2008/0089923 A1 | 4/2008 | Burkstrand et al. |
| 2008/0095849 A1 | 4/2008 | Wu et al. |

(56) References Cited

U.S. PATENT DOCUMENTS

| | | |
|---|---|---|
| 2008/0132922 A1 | 6/2008 | Buevich et al. |
| 2008/0154241 A1 | 6/2008 | Burkstrand et al. |
| 2008/0228193 A1 | 9/2008 | Matityahu |
| 2008/0241212 A1 | 10/2008 | Moses et al. |
| 2008/0311191 A1 | 12/2008 | Nangia et al. |
| 2009/0076595 A1 | 3/2009 | Lindquist et al. |
| 2009/0087380 A1 | 4/2009 | Fasching et al. |
| 2009/0123508 A1 | 5/2009 | Cheng et al. |
| 2009/0142400 A1 | 6/2009 | Hiles et al. |
| 2009/0155326 A1 | 6/2009 | Mack et al. |
| 2009/0177229 A1 | 7/2009 | Gulotta et al. |
| 2009/0182425 A1 | 7/2009 | Duda et al. |
| 2009/0198197 A1 | 8/2009 | Bischoff et al. |
| 2009/0263321 A1 | 10/2009 | Mcdonald et al. |
| 2009/0263441 A1 | 10/2009 | Mckay |
| 2009/0263443 A1 | 10/2009 | King |
| 2009/0263451 A1 | 10/2009 | King |
| 2009/0264472 A1 | 10/2009 | Wohabrebbi et al. |
| 2009/0264477 A1 | 10/2009 | Zanella et al. |
| 2009/0264489 A1 | 10/2009 | Hildebrand et al. |
| 2009/0325879 A1 | 12/2009 | Norton et al. |
| 2010/0023126 A1 | 1/2010 | Grotz |
| 2010/0055437 A1 | 3/2010 | Fink et al. |
| 2010/0158970 A1 | 6/2010 | Tipton et al. |
| 2010/0168808 A1 | 7/2010 | Citron |
| 2010/0198278 A1 | 8/2010 | Cobian et al. |
| 2010/0203100 A1 | 8/2010 | Cobian et al. |
| 2010/0203102 A1 | 8/2010 | Wohabrebbi |
| 2010/0209471 A1 | 8/2010 | Weber |
| 2010/0222873 A1 | 9/2010 | Atanasoska et al. |
| 2010/0249783 A1 | 9/2010 | Trieu |
| 2011/0027331 A1 | 2/2011 | Hobot |
| 2011/0060309 A1 | 3/2011 | Lee et al. |
| 2011/0081422 A1 | 4/2011 | Masinde et al. |
| 2011/0082545 A1 | 4/2011 | Freund |
| 2011/0129801 A1 | 6/2011 | Barman |
| 2011/0137243 A1 | 6/2011 | Hossainy et al. |
| 2011/0152839 A1 | 6/2011 | Cima et al. |
| 2011/0184037 A1 | 7/2011 | Haddock et al. |
| 2011/0206752 A1 | 8/2011 | Carreno et al. |
| 2011/0224245 A1 | 9/2011 | Schachter |
| 2011/0281882 A1 | 11/2011 | Zhang et al. |
| 2012/0009240 A1 | 1/2012 | Stopek et al. |
| 2012/0097194 A1 | 4/2012 | Mcdaniel et al. |
| 2012/0100192 A1 | 4/2012 | Penhasi et al. |
| 2012/0114740 A1 | 5/2012 | Garcia et al. |
| 2012/0165795 A1 | 6/2012 | Seiler et al. |
| 2012/0239001 A1 | 9/2012 | Barry et al. |
| 2012/0263761 A1 | 10/2012 | Mcdonald et al. |
| 2012/0316199 A1 | 12/2012 | Ward et al. |
| 2013/0018321 A1 | 1/2013 | Mckay |
| 2013/0071463 A1 | 3/2013 | Palasis et al. |
| 2013/0136811 A1 | 5/2013 | Schachter |
| 2013/0158652 A1 | 6/2013 | Palasis et al. |
| 2013/0164347 A1 | 6/2013 | Gensini et al. |
| 2013/0261594 A1 | 10/2013 | Stopek et al. |
| 2013/0280272 A1 | 10/2013 | Trogden et al. |
| 2014/0052183 A1 | 2/2014 | Freese |
| 2014/0065202 A1 | 3/2014 | Ito |
| 2014/0072608 A1 | 3/2014 | Logothetidis et al. |
| 2014/0086971 A1* | 3/2014 | Hall ............... A61L 31/16 514/56 |
| 2014/0088347 A1 | 3/2014 | Frigstad et al. |
| 2014/0105956 A1 | 4/2014 | Banerjee et al. |
| 2014/0107159 A1 | 4/2014 | Ebersole et al. |
| 2014/0170204 A1 | 6/2014 | Desai et al. |
| 2014/0193466 A1 | 7/2014 | Lawrence et al. |
| 2014/0193504 A1 | 7/2014 | Wooley et al. |
| 2014/0214175 A1 | 7/2014 | Barron et al. |
| 2014/0255464 A1 | 9/2014 | Hakimimehr et al. |
| 2014/0271770 A1 | 9/2014 | Clay et al. |
| 2014/0287053 A1 | 9/2014 | Helliwell et al. |
| 2015/0018969 A1 | 1/2015 | Fulmer et al. |
| 2015/0024031 A1 | 1/2015 | Rabinow et al. |
| 2015/0024116 A1 | 1/2015 | Matson et al. |
| 2015/0038415 A1 | 2/2015 | Zupancich |
| 2015/0039097 A1 | 2/2015 | Biris |
| 2015/0150988 A1 | 6/2015 | Shalaby et al. |
| 2015/0246001 A1 | 9/2015 | Zupancich et al. |
| 2015/0272877 A1 | 10/2015 | Shi et al. |
| 2015/0290170 A1 | 10/2015 | Liu et al. |
| 2015/0342964 A1 | 12/2015 | Gray et al. |
| 2016/0038632 A1 | 2/2016 | Shah et al. |
| 2016/0089335 A1 | 3/2016 | Ohri et al. |
| 2016/0136094 A1 | 5/2016 | Criscione et al. |
| 2016/0144040 A1 | 5/2016 | Cheng |
| 2016/0144067 A1 | 5/2016 | Armbruster et al. |
| 2016/0151257 A1 | 6/2016 | Klingman |
| 2016/0184340 A1 | 6/2016 | Kritikou |
| 2016/0287367 A1 | 10/2016 | Rontal |
| 2016/0331853 A1 | 11/2016 | Taub |
| 2016/0339152 A1 | 11/2016 | Bonutti et al. |
| 2016/0354309 A1 | 12/2016 | Heitzmann et al. |
| 2017/0014337 A1 | 1/2017 | Walsh |
| 2017/0079929 A1 | 3/2017 | Davey |
| 2017/0112935 A1 | 4/2017 | Holzer et al. |
| 2017/0128632 A1 | 5/2017 | Mcjames |
| 2017/0182168 A1 | 6/2017 | Ottoboni et al. |
| 2017/0196499 A1 | 7/2017 | Hunter |
| 2017/0196508 A1 | 7/2017 | Hunter |
| 2017/0216597 A1 | 8/2017 | Hou et al. |
| 2017/0239183 A1 | 8/2017 | Reynolds et al. |
| 2017/0246117 A1 | 8/2017 | Helliwell et al. |
| 2017/0281778 A1 | 10/2017 | Ottoboni et al. |
| 2018/0092855 A1 | 4/2018 | Kim et al. |
| 2018/0193537 A1 | 7/2018 | Honglei et al. |
| 2018/0361827 A1 | 12/2018 | Carlson et al. |
| 2019/0351108 A1 | 11/2019 | Wang et al. |
| 2020/0009293 A1 | 1/2020 | Teu et al. |
| 2021/0186868 A1 | 6/2021 | Naga et al. |
| 2021/0308338 A1 | 10/2021 | Ruane et al. |
| 2022/0072207 A1 | 3/2022 | Wang et al. |
| 2022/0117885 A1 | 4/2022 | Naga et al. |
| 2022/0183963 A1 | 6/2022 | Kim et al. |
| 2022/0183964 A1 | 6/2022 | Naga et al. |
| 2023/0136789 A1 | 5/2023 | Ruane et al. |
| 2024/0016774 A1 | 1/2024 | Kim et al. |
| 2024/0226394 A1 | 7/2024 | Wang et al. |
| 2024/0315957 A1 | 9/2024 | Naga et al. |

FOREIGN PATENT DOCUMENTS

| | | |
|---|---|---|
| CN | 1344156 A | 4/2002 |
| CN | 1762331 A | 4/2006 |
| CN | 102000366 A | 4/2011 |
| CN | 102341133 A | 2/2012 |
| CN | 103405748 A | 11/2013 |
| CN | 103703079 A | 4/2014 |
| CN | 104474595 A | 4/2015 |
| CN | 104474595 B | 1/2017 |
| CN | 106344521 A | 1/2017 |
| EP | 0311065 B1 | 2/1994 |
| EP | 1868662 B1 | 5/2010 |
| EP | 2197419 A2 | 6/2010 |
| EP | 2209469 A2 | 7/2010 |
| EP | 2229171 A2 | 9/2010 |
| EP | 2262481 A2 | 12/2010 |
| EP | 2285363 A2 | 2/2011 |
| EP | 2288352 A2 | 3/2011 |
| EP | 2288353 A2 | 3/2011 |
| EP | 2368522 A1 | 9/2011 |
| EP | 2444074 A2 | 4/2012 |
| EP | 2444075 A2 | 4/2012 |
| EP | 2696851 A1 | 2/2014 |
| EP | 2719717 A1 | 4/2014 |
| EP | 3000463 A1 | 3/2016 |
| EP | 3085359 A1 | 10/2016 |
| EP | 2195073 B1 | 3/2017 |
| EP | 2444073 B1 | 5/2017 |
| EP | 2911647 B1 | 3/2018 |
| EP | 2444075 B1 | 9/2018 |
| EP | 3518999 A1 | 8/2019 |
| EP | 3691618 A1 | 8/2020 |
| EP | 3737433 A1 | 11/2020 |

(56) References Cited

FOREIGN PATENT DOCUMENTS

| | | |
|---|---|---|
| EP | 3793536 A1 | 3/2021 |
| EP | 3843710 A1 | 7/2021 |
| GB | 201505527 | 5/2015 |
| JP | H02119866 A | 5/1990 |
| JP | 2000507847 A | 6/2000 |
| JP | 2006512312 A | 4/2006 |
| JP | 2009511196 A | 3/2009 |
| JP | 2012017329 A | 1/2012 |
| JP | 2015522649 A | 8/2015 |
| JP | 2016528949 A | 9/2016 |
| JP | 2018511410 A | 4/2018 |
| JP | 2021072894 A | 5/2021 |
| NO | 2009129433 A2 | 10/2009 |
| WO | 9509613 A1 | 4/1995 |
| WO | 9858653 A1 | 12/1998 |
| WO | 9936071 A1 | 7/1999 |
| WO | 2004089291 A2 | 10/2004 |
| WO | 2006099409 A3 | 3/2007 |
| WO | 2007047420 A2 | 4/2007 |
| WO | 2008061355 A1 | 5/2008 |
| WO | 2008127411 A1 | 10/2008 |
| WO | 2008131089 A2 | 10/2008 |
| WO | 2008136856 A2 | 11/2008 |
| WO | 2009069151 A2 | 6/2009 |
| WO | 2009113972 A2 | 9/2009 |
| WO | 2009129432 A2 | 10/2009 |
| WO | 2009129439 A2 | 10/2009 |
| WO | 2009129453 A2 | 10/2009 |
| WO | 2009129456 A2 | 10/2009 |
| WO | 2009129460 A2 | 10/2009 |
| WO | 2009129464 A2 | 10/2009 |
| WO | 2009129491 A2 | 10/2009 |
| WO | 2009129494 A2 | 10/2009 |
| WO | 2009129509 A2 | 10/2009 |
| WO | 2009129519 A2 | 10/2009 |
| WO | 2009129527 A2 | 10/2009 |
| WO | 2009129531 A2 | 10/2009 |
| WO | 2010016832 A1 | 2/2010 |
| WO | 2010075298 A2 | 7/2010 |
| WO | 2010088697 A2 | 8/2010 |
| WO | 2011098578 A2 | 8/2011 |
| WO | 2011139594 A2 | 11/2011 |
| WO | 2012064963 A1 | 5/2012 |
| WO | 2012142318 A1 | 10/2012 |
| WO | 2013013123 A1 | 1/2013 |
| WO | 2013040325 A1 | 3/2013 |
| WO | 2014016428 A1 | 1/2014 |
| WO | 2014059558 A1 | 4/2014 |
| WO | 2014064140 A1 | 5/2014 |
| WO | 2014066653 A1 | 5/2014 |
| WO | 2014137454 A1 | 9/2014 |
| WO | 2014172572 A1 | 10/2014 |
| WO | 2014204708 A1 | 12/2014 |
| WO | 2015015278 A1 | 2/2015 |
| WO | 2015135907 A1 | 9/2015 |
| WO | 2016123352 A1 | 8/2016 |
| WO | 2016159885 A1 | 10/2016 |
| WO | 2017019829 A1 | 2/2017 |
| WO | 2017034363 A1 | 3/2017 |
| WO | 2017075232 A1 | 5/2017 |
| WO | 2017146819 A1 | 8/2017 |
| WO | 2018009637 A1 | 1/2018 |
| WO | 2018063096 A1 | 4/2018 |
| WO | 2018067882 A1 | 4/2018 |
| WO | 2018172494 A1 | 9/2018 |
| WO | 2018227293 A1 | 12/2018 |
| WO | 2019071243 A1 | 4/2019 |
| WO | 2019136490 | 7/2019 |
| WO | 2019221853 A1 | 11/2019 |
| WO | 2019071243 A8 | 3/2020 |
| WO | 2020046973 A1 | 3/2020 |
| WO | 2020047013 A1 | 3/2020 |
| WO | 2020210764 A1 | 10/2020 |
| WO | 2020210770 A2 | 10/2020 |
| WO | 2021178930 A1 | 9/2021 |
| WO | 2022082196 A1 | 4/2022 |

OTHER PUBLICATIONS

NIHR HSC , et al., "AIGISRx Antibacterial Envelope for Preventing Infection in Implanted Cardiac Devices", Birmingham NIHR Horizon Scanning Centre NIHR HSC Horizon Scanning Review 2012 XP055320647 Retrieved from the Internet URLhttpwwwhsr icnihracuktopicsaigisrxantibacterialenvelopeforpreventinginfection inimplantedcardiacdevices.

Tarakji et al., "Cardiac implantable electronic device infections: Presentation, management, and patient outcomes", Heart Rhythm, vol. 7, No. 8, Aug. 2010. 6 pages.

Voigt et al., "Continued rise in rates of cardiovascular implantable electronic device infections in the United States; temporal trends and causative insights", Pace, vol. 33, Apr. 2010, 6 pages.

Ball et al., Electrospun Solid Dispersions of Maraviroc for Rapid Intravaginal Preexposure Prophylaxis of HIV, Antimicrobial Agents and Chemotherapy, Aug. 2014, vol. 58, No. 8, p. 4855-4865.

Bassi et al., Polymeric films as a promising carrier for bioadhesive drug delivery: Development, characterization and optimization, Saudi Pharmaceutical Journal, (2017) 25, 32-43.

Curley et al., Prolonged Regional Nerve Blockade Injectable Biodegradable Bupivacaine/Polyester Microspheres, Anesthesiology, 1996, 84, 1401-10.

Epstein-Barash et al., Prolonged duration local anesthesia with minimal toxicity, PNAS, Apr. 28, 2009, vol. 106, No. 17, 7125-7130.

European Search Report dated Apr. 30, 2020; European Patent Application No. 17856916.6; 10 pages.

Farid et al., Promote Recurrent Aphthous Ulcer Healing with Low Dose Predisolone Bilayer Mucoadhesive Buccal Film, Current Drug Delivery, vol. 14, No. 1, Jan. 9, 2017, pp. 123-125.

Fites et al., Controlled Drug Release through Polymeric Films, Journal of Pharmaceutical Sciences, vol. 59, No. 5, May 1970, 610-613.

Friess, Wolfgang, Review Article: Collagen—biomaterial for drug delivery, European Journal of Pharmaceutics and Biopharmaceutics, 45 (1998) 113-136.

International Search Report and Written Opinion mailed Feb. 19, 2019; International Application No. PCT/US2018/054777; 15 pages.

International Search Report and Written Opinion mailed Feb. 21, 2019; International Application No. PCT/US2018/054779; 17 pages.

International Search Report and Written Opinion mailed Jul. 24, 2019; International Application No. PCT/US2019/027104; 14 pages.

International Search Report and Written Opinion mailed Jul. 3, 2020; International Application No. PCT/US2020/027852; 14 pages.

International Search Report and Written Opinion mailed Jun. 17, 2020; International Application No. PCT/US2020/027861; 11 pages.

International Search Report and Written Opinion mailed May 10, 2019; International Application No. PCT/US2018/054780; 13 pages.

International Search Report and Written Opinion mailed May 23, 2019; International Application No. PCT/US2019/012795; 15 pages.

International Search Report and Written Opinion mailed Nov. 14, 2019; International Application No. PCT/US2019/048437; 15 pages.

International Search Report and Written Opinion mailed Nov. 20, 2019; International Application No. PCT/US2019/048386; 13 pages.

Irfan et al., Orally disintegrating films: A modern expansion in drug delivery system, Saudi Pharmaceutical Journal, (2016) 24, 537-546.

Ito et al., Three-Layered Microcapsules as a Long-Term Sustained Release Injection Preparation, International Journal of Pharmaceuticals, vol. 384, No. 1-2, Jan. 1, 2010, pp. 53-59.

Jain, Anjali et al., Injectable formulations of ply(lactic acid) and its copolymers in clinical use, Advaned Drug Delivery Reviews, vol. 107, Jul. 14. 2016, pp. 213-227.

Jethara et al., Sustained Release Drug Delivery Systems: a Patent Overview, Aperito Journal of Drug Designing and Pharmacology, 2014: 1:1, 15 pages.

Kanagale et al., Formulation and Optimization of Porous Osmotic Pump-based Controlled Release System and Oxybutynin, AAPA PharmSciTech 2007, 8 (3), Article 53, 7 pages.

(56) References Cited

OTHER PUBLICATIONS

Karki et al., Thin films as an emerging platform for drug delivery, Asian Journal of Pharmaceutical Sciences, II, (2016), 559-574.
Kau et al., Sustained Release of Lidocaine from Solvent-Free Biodegradable Poly [(d,l)-Lactide-co-Glycolide] (PLGA): In Vitro and In Vivo Study, Materials, 2014, 17 pages.
Knecht et al.; Mechanical testing of fixation techniques for scaffold-based tissue-engineered grafts; Journal of Biomedical Materials Research Part B: Applied Biomaterials; vol. 83, No., 1; Feb. 22, 2007; pp. 50-57.
International Search Report and Written Opinion dated Oct. 30, 2017; International Application No. PCT/SG2017/050481; 10 pages.
Lee et al., "Results of a model analysis of the cost-effectiveness of liraglutide versus exenatide added to metformin, glimepiride, or both for the treatment of type 2 diabetes in the United States", Clinical Therapeutics, vol. 32, No. 10, 2010, 12 pages.
Liu et al.; Less harmful acidic degradation of poly(lactic-co-glycolic acid) bone tissue engineering scaffolds through itania nanoparticle addition; International Journal of Nanomedicine; vol. 1, No. 4; Jan. 1, 2006; pp. 541-545.
Liu et al: "Paclitaxel or 5-fluorouracil/esophageal stent combinations as a novel approach for the treatment of esophageal cancer", Biomaterials, vol. 53, Jun. 1, 2015 (Jun. 1, 2015), pp. 592-599.
Mcalvin et al., Local Toxicity from Local Anesthetic Polymeric Microparticles, Anesth Analg., Apr. 2013, 116(4): 794-803.
Ohri et al., Inhibition by Local Bupivacaine-Releasing Microspheres of Acute Postoperative Pain from Hairy Skin Incision, www.anesthesia-analgesia.org, Sep. 2013, vol. 117, No. 3, 14 pages.
Padera et al., Local myotoxicity from sustained release of bupivacaine from microparticles, Anesthesiology, May 2008, 108(5): 921-928.
PCT International Search Report for PCT/SG/2016/050158 mailed Jun. 15, 2016.
Roy et al., Effects of plasticizers and surfactants on the film forming properties of hydroxypropyl methylcellulose for the coating of diclofenac sodium tablets, Saudi Pharmaceutical Journal (2009) 17, 233-241.
Santamaria et al., Drug delivery systems for prolonged duration local anesthesia, Materials Today, vol. 20, No. 1, Jan./Feb. 2017, 22 pages.
Seo et al., Polyurethane membrane with porous surface for controlled drug release in drug eluting stent, Biomaterials Research, 2014, 18:15, 5 pages.
Shaikh et al., "Engineering Stent Based Delivery System for Esophageal Cancer Using Docetaxel", Molecular Pharmaceutics, vol. 12, No. 7, Jul. 6, 2015 (Jul. 6, 2015), pp. 2305-2317.
Shipton, Edward A., New Formulations of Local Anaesthetics—Part I, Anesthesiology Research and Practice, 2012, 12 pages.
Shona Pek, Sustained Release of Bupivacaine for Post-Surgical Pain Relief Using Core-Shell Microspheres, Journal of Materials Chemistry B, 2014, 9 pages.
Sokolsky-Papkov et al., Long-Acting Poly (DL: Lactic Acid-Castor Oil) 3:7-Bupivacaine Formulation: Effect of Hydrophobic Additives, Pharmaceutical Research, Jun. 2011, 10 pages.
Tanabe et al., Controlled Indomethacin Release from Mucoadhesive Film: In Vitro and Clinical Evaluations, Yakugaku Zasshi Journal of the Pharmaceutical Society of Japan, vol. 128, No. 11, Nov. 1, 2008, pp. 1673-1679.
Weiniger, et al., Extended release formulations for local anaesthetic agents, Anaesthesia 2012, 67, 906-916.
Yamamura et al., Pain Relief of Oral Ulcer by Dibucaine-film, Elsevier Science Publishers, Amsterdam, NL, vol. 83, 1999, pp. 625-626.
Yan et al., Towards nanoporous polymer thin film-based drug delivery systems, Thin Solid Films, 517 (2009), 1794-1798.
Zorzetto et al., From micro-to nanostructured implantable device for local anesthetic delivery, International Journal of Nanomedicine, Jun. 8, 2016, 2695-2709.
Hong, Y., et al., "Generating Elastic, Biodegradable Polyurethane/Poly(lactide-co-glycolide) Fibrous Sheets with Controlled Antibiotic Release via Two-Stream Electrospinning", Biomacromolecules, 2008, 1200-1207.
Liu et al., "Evaluation of two polymeric blends (EVA/PLA and EVA/PEG) as coating film materials for paclitaxel-eluting stent application", J Mater Sci: Mater Med (2011) 22: 327-337.
Jin, Zhu, et al., "A PTX/nitinol stent combination with temperature-responsive phase-change 1-hexadecanol for magnetocaloric drug delivery: Magnetocaloric drug release and esophagus tissue penetration".
Kolek, Matthew J., et al., "Use of an Antibacterial Envelope is Associated with Reduced Cardiac Implantable Electronic Device Infections in High-Risk Patients", Pacing and Clinical Electrophysiology, vol. 36, Mar. 2013, 354-361.
Lei, L, et al., "5-Fluorouracil-loaded multilayered films for drug controlled releasing stent application: Drug release, microstructure, and ex vivo permeation behaviors".
Drager, Christiane et al., Prolonged Intercostal Nerve Blockade in Sheep Using Controlled-release of Bupivacaine and Dexamethasome from Polymer Microspheres, Anesthesiology, vol. 89, No. 4, Oct. 1998, pp. 969-979.
De Clercq et al., "Preclinical evaluation of local prolonged release of paclitaxel from gelatin microspheres for the prevention of recurrence of peritoneal carcinomatosis in advanced ovarian cancer", Science Reports, vol. 9, No. 14881, Oct. 16, 2019, pp. 1-19.
International Search Report and Written Opinion dated Feb. 17, 2022, International Application No. PCT/US2021/071861, 10 pages.
De Clercq et al., "Preclinical evaluation of local prolonged release of paclitaxel from gelatin microspheres for the prevention of recurrence of peritoneal carcinomatosis in advanced ovarian cancer", Science Reports, vol. 9, No. 14881, Oct. 16, 2019, 19 pages.
Rong, et al., "PLC films incorporated with paclitaxel/5-flourouracil: Effects of formulation and spacial architecture on drug release", International Journal of Pharmaceutics, vol. 427, 2012, pp. 242-251.
Jackson, et al., "The characterization of paclitaxel-loaded microspheres manufactured from blends of poly(lactic-co-glycolic acid) (PLGA) and low molecular weight diblock copolymers", International Journal of Pharmaceutics 342 (2007) 6-17.

\* cited by examiner

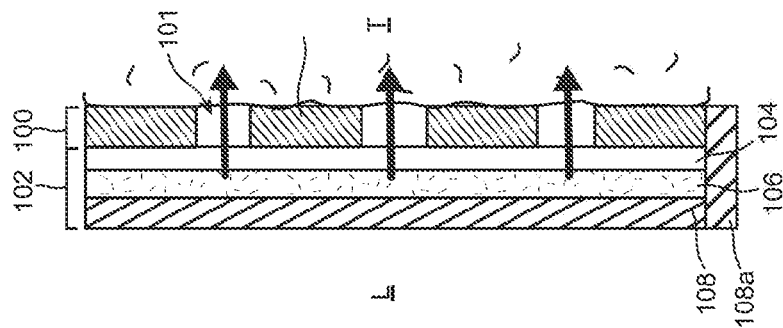
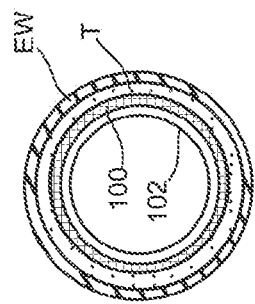
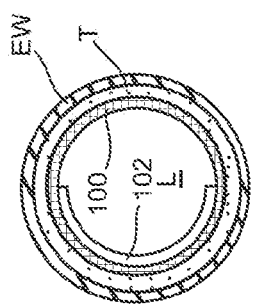
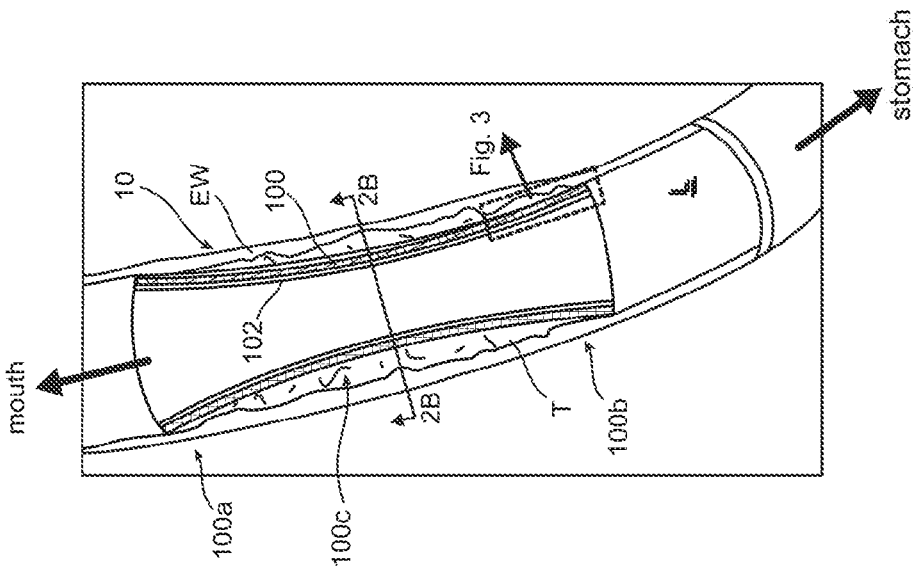

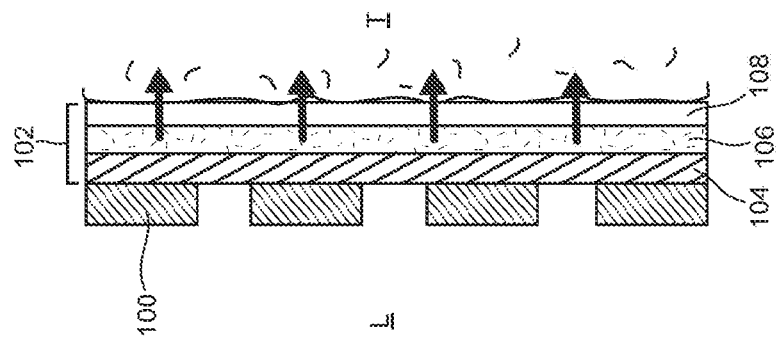
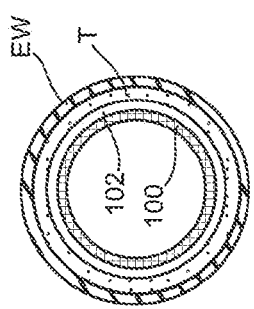
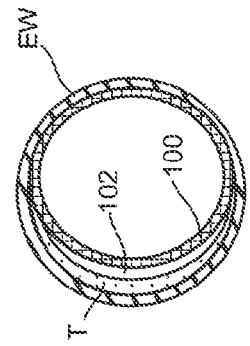
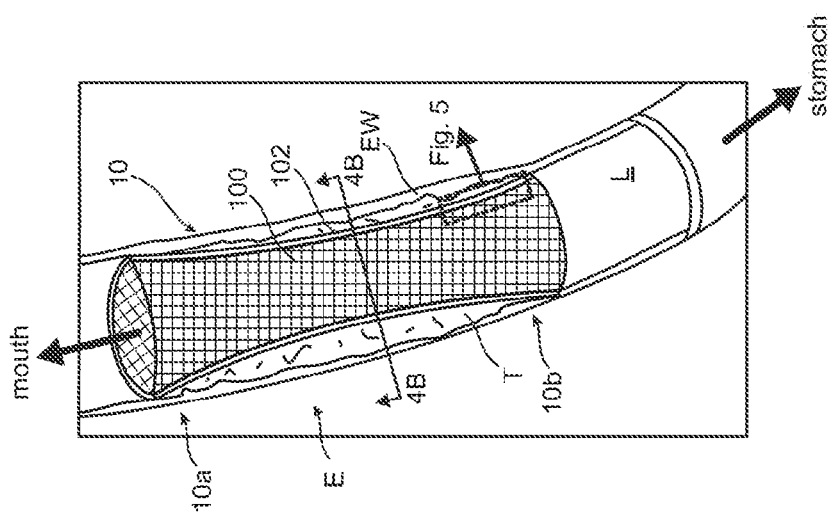

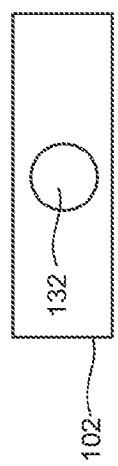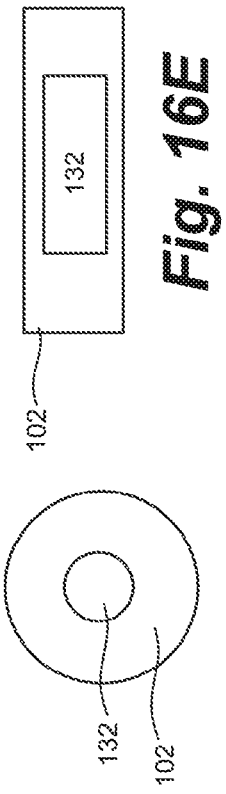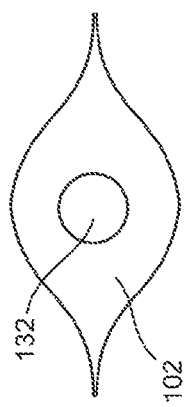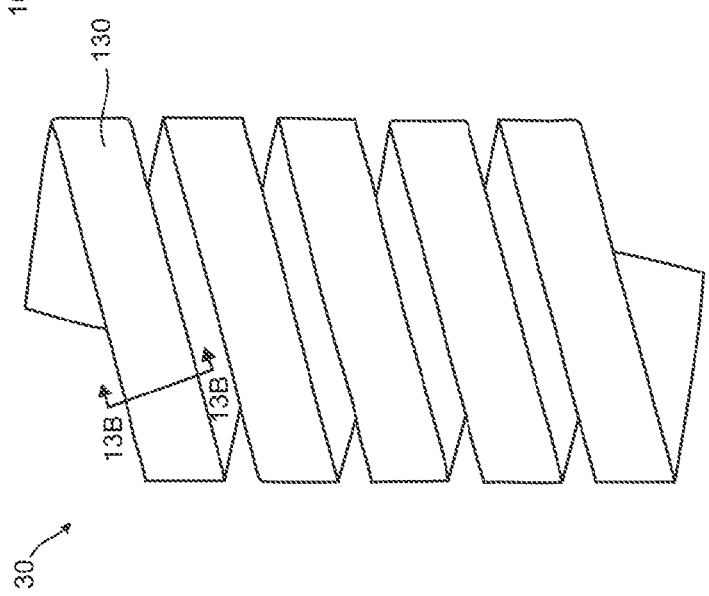
Fig. 16A
Fig. 16B
Fig. 16C
Fig. 16D
Fig. 16E

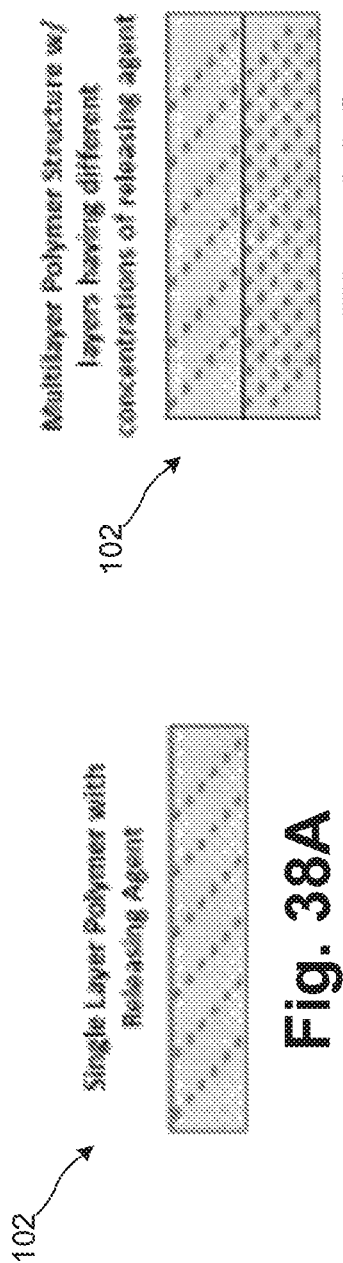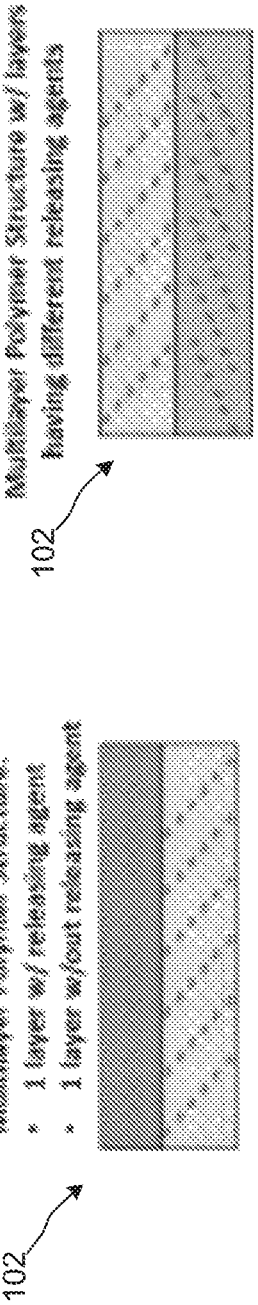
Fig. 38A Single Layer Polymer with Releasing Agent
Fig. 38B Multilayer Polymer Structure: 1 layer w/ releasing agent, 1 layer w/out releasing agent
Fig. 38C Multilayer Polymer Structure w/ layers having different concentrations of releasing agent
Fig. 38D Multilayer Polymer Structure w/ layers having different releasing agents

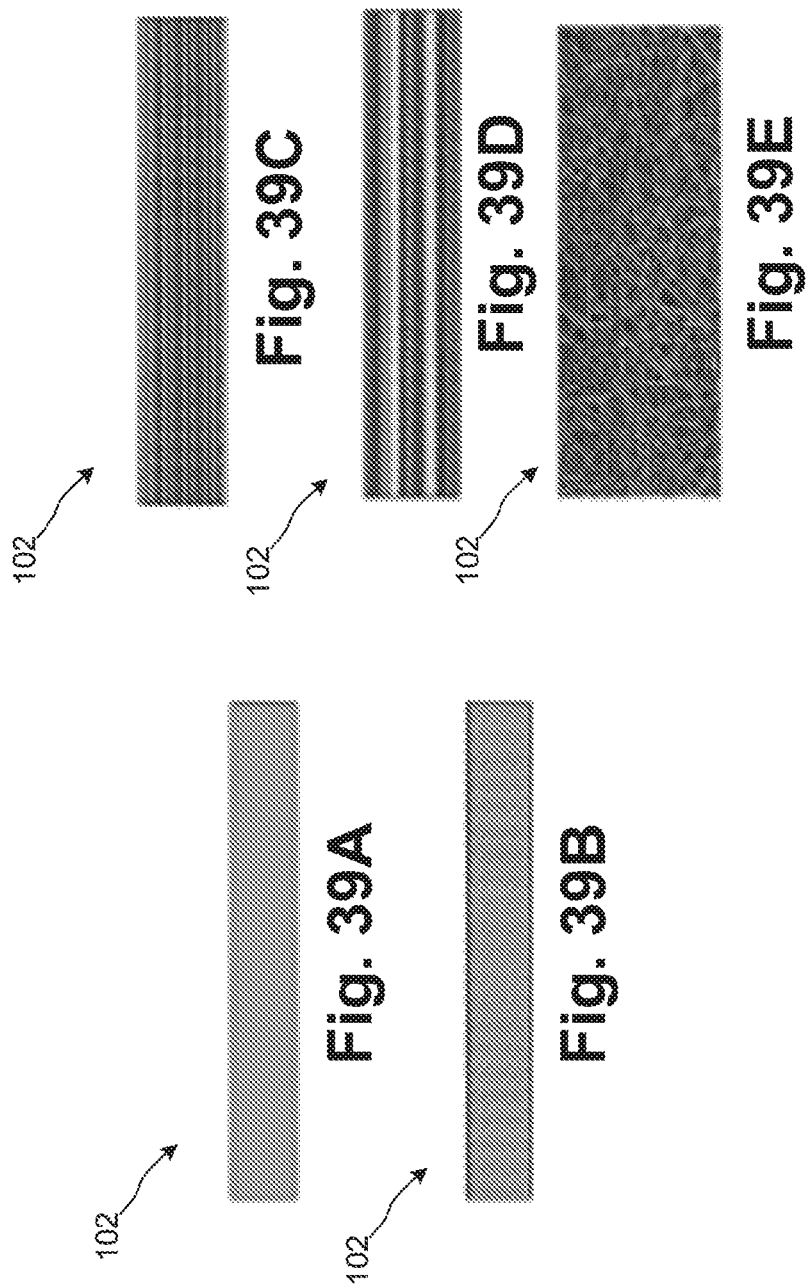

DEVICES, SYSTEMS, AND METHODS FOR TREATING INTRALUMINAL CANCER VIA CONTROLLED DELIVERY OF THERAPEUTIC AGENTS

CROSS-REFERENCE TO RELATED APPLICATION(S)

The present application is a 371 U.S. national phase application of International Application No. PCT/US2019/012795, filed Jan. 8, 2019, which claims the benefit of priority to U.S. Provisional Application No. 62/614,884, filed Jan. 8, 2018, and International Application No. PCT/US2018/054777, filed Oct. 8, 2018, which are incorporated by reference herein in their entireties.

TECHNICAL FIELD

The present technology relates to devices, systems, and methods for treating intraluminal cancer via controlled delivery of therapeutic agents. In particular, the present technology is directed to devices, systems, and methods for treating esophageal cancer.

BACKGROUND

Esophageal cancer is the eighth most common cancer worldwide, with an estimated 456,000 new cases in 2012, and the sixth most common cause of death from cancer with an estimated 400,000 deaths. The incidence rates of esophageal cancer vary greatly based on region, with the highest rates found in Asia, including China and Central Asia, and in Africa. M. Center, et al., *Global Cancer Facts and Figures*, American Cancer Society, 2nd edition, 2008. The United States has a relatively low-incidence rate for carcinoma of esophagus, with approximately 16,640 new cases and 14,500 deaths in 2010. A. Jemal, et al., *Cancer Statistics, 2010*, CA Cancer Journal for Clinicians, Vol. 60, No. 5, pp. 277-300, 2010. Most carcinomas of the esophagus are diagnosed at an advanced stage, with very few patients eligible for potentially curative resection at the time of presentation, leaving palliation as a more realistic option for these patients. T. L. Weigel, et al., *Endoluminal Palliation for Dysphagia Secondary to Esophageal Carcinoma*, Surgical Clinics of North America, Vol. 82, No. 4, pp. 747-761, 2002.

Dysphagia is the predominant symptom in more than 83% of patients with esophageal cancer resulting in weight loss and malnutrition. Gibbs, *The Changing Profile of Esophageal Cancer Presentation and Its Implication for Diagnosis*, J Nat Med Assoc, Vol. 99: pp. 620-626, 2007. Currently, the preferred method for palliation of dysphagia is implanting a self-expanding metal stent ("SEMS") in the esophageal lumen at the site of the tumor. Although SEMS provides immediate palliation of dysphagia for most patients, in some instances the tumor will grow through the openings in the mesh structure, rendering the SEMS ineffective for maintaining patency of the esophageal lumen and/or making it virtually impossible to remove or adjust the positioning of the stent. To address this issue, several conventional SEMS include a thin silicone or plastic covering over the body of the stent to prevent tumor ingrowth. However, the covering also prevents the stent wall from engaging the tumor and/or vessel wall, resulting in poor fixation and potential migration of the stent. These and other shortcomings of conventional SEMS result in complications in up to 53%-65% of patients, with a reintervention rate as high as 50%. J. Martinez et al., *Esophageal Stenting in the Setting of Malignancy*, ISRN Gastroenterology, Vol. 2011, Article ID 719575.

Although SEMS placement is often accompanied by radiation and/or systemically-administered chemotherapy (i.e., intravenously), esophageal and gastric tumors demonstrate innate resistance to most systemically administered chemotherapeutic agents. Moreover, even when the tumor is less resistant than expected, the amount of chemotherapeutic agent that can be delivered is capped because of toxicity risks to the rest of the body. Accordingly, there is a need for improved devices and methods for treating or otherwise palliating the symptoms of esophageal cancer.

SUMMARY

The present technology is directed to devices, systems, and methods for treating intraluminal cancer, especially cancer of the upper gastrointestinal tract between the mouth and the gastroduodenal junction. Several embodiments of the present technology, for example, are directed to devices, systems, and methods for treating esophageal cancer and/or palliating the symptoms of esophageal cancer. FIG. 1, for example, shows a portion of the upper gastrointestinal tract of a human patient including the esophagus E, and an enlarged, cross-sectional view of an esophageal tumor T. As demonstrated by FIG. 1, esophageal tumors extend into the lumen of the esophagus E, thereby obstructing the esophageal lumen. Because of this, patients with esophageal cancer often present with dysphagia (i.e., difficulty swallowing food, liquids, or oral secretions), as well as dysphagia-related symptoms such as pain, poor nutrition, nausea, weight loss, decrease in quality of life, and other symptoms. As the tumor grows, the symptoms worsen. The devices, systems, and methods described herein include a therapeutic member configured to be positioned adjacent a tumor within the esophageal lumen and provide controlled, local delivery of a chemotherapeutic agent to the tumor to eliminate, reduce, stabilize and/or otherwise slow the progression of tumor growth and maintain the patency of the esophageal lumen. In some embodiments, the therapeutic member may additionally cause regression of the tumor.

Because the therapeutic members disclosed herein administer the chemotherapeutic agent locally, the present technology can deliver greater amounts of chemotherapeutic agent to the tumor locally than would be possible through systemic administration without exposing the patient to toxic levels of the agent systemically. In some embodiments, the therapeutic member may be configured to deliver a high, sustained local dose to an esophageal tumor over the course of days, weeks, or months.

In some embodiments, the therapeutic member may be carried by or delivered with one or more anchoring members (such as a stent) to improve fixation of the therapeutic member to the tumor and/or esophageal wall and prevent migration of the therapeutic member. In some embodiments, the therapeutic member may be carried on the surface of the anchoring member, and in some embodiments, the therapeutic member may be separate from the anchoring member and delivered separately. In some embodiments, the combination of release of chemotherapeutic agents from the therapeutic member and the radial resistive and/or chronic outward force of the anchoring member may have a more durable effect on the treatment site (e.g., tumor, esophageal wall, etc.).

The present technology is illustrated, for example, according to various aspects described herein with reference to FIGS. 2A-51B. Various examples of aspects of the present technology are described below as numbered clauses (1, 2, 3, etc.) for convenience. These are provided as examples and do not limit the subject technology.

Clause 1. A device for treating a patient with esophageal cancer, the device comprising:

a therapeutic member configured for endoluminal placement via the delivery system into the esophagus of the patient, wherein the therapeutic member comprises a treatment portion comprising a film for controlled release of a chemotherapeutic agent, the film comprising:

a control region comprising a first polymer and releasing agent mixed with the first polymer, wherein the releasing agent is configured to dissolve when the therapeutic member is placed in vivo to form channels in the control region;

a therapeutic region comprising the chemotherapeutic agent mixed with a second polymer; and a substantially impermeable base region, wherein the film is configured to release the chemotherapeutic agent in a direction away from the substantially impermeable base region, and wherein the therapeutic member is configured to be endoluminally positioned within the esophageal lumen such that the treatment portion of the therapeutic member is proximate to a treatment site associated with the esophagus of the patient, and wherein the therapeutic member is configured to administer a therapeutically effective dose to the treatment site for a sustained period following endoluminal placement of the therapeutic member.

Clause 2. The device of Clause 1, wherein the device includes a delivery system, and wherein the delivery system includes an endoscopic catheter.

Clause 3. The device of Clause 1 or Clause 2, wherein the device includes a delivery system, and wherein the delivery system includes coaxial tubular shafts.

Clause 4. The device of Clause 3, wherein the tubular shafts are concentric.

Clause 5. The device of any one of Clauses 1-4, wherein the delivery system includes an inflatable balloon.

Clause 6. The device of any one of Clauses 1-5, wherein the device includes a delivery system, and wherein the delivery system is an over-the-wire system such that the therapeutic member is delivered over a guidewire to the treatment site.

Clause 7. The device of any one of Clauses 1-6, wherein the device includes a delivery system, and wherein the delivery system includes one or more radiopaque markers configured to orient a clinician.

Clause 8. The device of any one of Clauses 1-7, wherein the device includes a delivery system, and wherein the delivery system includes a handle with one or more actuators configured to be activated by rotational movement.

Clause 9. The device of any one of Clauses 1-8, wherein the device includes a delivery system, and wherein the delivery system is a low-profile delivery system.

Clause 10. The device of any one of Clauses 1-9, wherein the therapeutic member is a cuff.

Clause 11. The device of any one of Clauses 1-9, wherein the therapeutic member is a sleeve.

Clause 12. The device of any one of Clauses 1-11, wherein the therapeutic member is configured such that, when implanted, it extends around less than the full circumference of the esophagus at the treatment site.

Clause 13. The device of any one of Clauses 1-12, wherein the therapeutic member or the treatment portion of the therapeutic member is a removable or replaceable patch.

Clause 14. The device of any one of Clauses 1-13, wherein the therapeutic member is a first therapeutic member, and the device further includes a second therapeutic member.

Clause 15. The device of any one of Clauses 1-14, wherein the treatment portion comprises the entirety of the therapeutic member.

Clause 16. The device of any one of Clauses 1-14, wherein the treatment portion comprises less than the entire therapeutic member such that the treatment portion is a distinct region along the length and/or circumference of the therapeutic member.

Clause 17. The device of Clause 16, wherein the treatment portion extends along only a portion of the length of the therapeutic member.

Clause 18. The device of Clause 16 or Clause 17, wherein the treatment portion extends along only a portion of the circumference of the therapeutic member.

Clause 19. The device of any one of Clauses 16-18 wherein the treatment portion extends along no more than 30, 60, 90, 120, 150, or 180 degrees of the therapeutic member.

Clause 20. The device of Clauses 16-19, wherein the therapeutic member includes multiple treatment portions that are longitudinally and/or radially spaced apart.

Clause 21. The device of any one of Clauses 1-20, wherein the therapeutic member is configured to be removed following a predefined period of time.

Clause 22a. The device of Clause 21, wherein the therapeutic member is a first therapeutic member, and the device is configured such that the first therapeutic member is interchangeable with a second therapeutic member having the same or different type and/or amount of therapeutic agent.

Clause 22b. The device of Clause 21, wherein the treatment portion is a first treatment portion, and the device is configured such that the first treatment portion is interchangeable with a second treatment portion having the same or different type and/or amount of therapeutic agent.

Clause 23. The device of any one of Clauses 1-22b, wherein the therapeutic member comprises a film.

Clause 24. The device of any one of Clauses 1-23, wherein the control region comprises a multilayer structure.

Clause 25. The device of any one of Clauses 1-23, wherein control region comprises a single layer and does not include a releasing agent.

Clause 26. The device of any one of Clauses 1-25, wherein the therapeutic region comprises a multilayer structure.

Clause 27. The device of any one of Clauses 1-26, wherein the therapeutic region comprises a plurality of microlayers.

Clause 28. The device of any one of Clauses 1-27, wherein the therapeutic region includes a releasing agent.

Clause 29. The device of any one of Clauses 1-28, wherein the therapeutic region includes a 1:1, a 2:1, a 3:1, or a 4:1 ratio of drug to polymer.

Clause 30. The device of any one of Clauses 1-29, wherein the therapeutic region includes multiple therapeutic agents.

Clause 31. The device of Clause 30, wherein the multiple therapeutic agents are contained in separate layers of the multilayer structure.

Clause 32. The device of Clause 30, wherein the multiple therapeutic agents are contained within the same layer of the multilayer structure.

Clause 33. The device of any one of Clauses 1-32, wherein the therapeutic region includes one or more vasoconstrictors to increase local absorption of a chemotherapeutic agent.

Clause 34. The device of any one of Clauses 1-33, wherein the base region includes a bioresorbable polymer.

Clause 35. The device of Clause 34, wherein the bioresorbable polymer is the same as the first and second polymers.

Clause 36. The device of Clause 34, wherein the bioresorbable polymer is different from the first and second polymers, and wherein the bioresorbable polymer has a longer degradation period than the first and second polymers.

Clause 37. The device of any one of Clauses 34-36, wherein the bioresorbable polymer includes at least one of polyglycolide (PGA), polycaprolactone (PCL), poly(L-lactic acid) (PLA) Suitable additional bioresorbable polymers and copolymers for use in the present invention include, but are not limited to, poly(alpha-hydroxy acids), poly(lactide-co-glycolide)(PLGA or DLG), poly(DL-lactide-co-caprolactone) (DL-PLCL), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(glycolide-co-carolactone) (PGCL), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, and propylene glycol.

Clause 38. The device of any one of Clauses 1-33, wherein the base region is a non-bioresorbable polymer.

Clause 39. The device of any one of Clauses 1-38, wherein the polymer is a monomer, co-polymer or ter-polymer.

Clause 40. The device of any one of Clauses 1-39, wherein the first and second polymers are the same polymer.

Clause 41. The device of any one of Clauses 1-39, wherein the first and second polymers are different polymers.

Clause 42. The device of any one of Clauses 1-41, wherein the first and/or second polymers have a degradation profile of 3, 6, 9, 12, 15, or 18 months.

Clause 43. The device of any one of Clauses 1-42, wherein the first and/or second polymers are non-bioresorbable polymers comprising at least one of polyurethane, silicone, and poly(ethylene vinyl acetate) (PEVA).

Clause 44. The device of any one of Clauses 1-43, wherein the therapeutic member is configured to be positioned such that the control region is closest to the esophageal wall, the base region is closest to the center of the esophageal lumen, the therapeutic agent region in between control region and the base regions.

Clause 45. The device of any one of Clauses 1-44, wherein a portion of the base region extends laterally even with or beyond the control region, and wherein the portion provides a seal to minimize the loss of therapeutic agent down the esophageal lumen.

Clause 46. The device of any one of Clauses 1-45, wherein the chemotherapeutic agent includes at least one of the chemotherapeutic agents identified in Table 1.

Clause 47. The device of any one of Clauses 1-47, wherein the chemotherapeutic agent comprises multiple agents for combination or sequential dosing Clause 48. The device of any one of Clauses 1-48, wherein the therapeutic region and/or treatment portion is configured to release an adjunctive agent.

Clause 49. The device of Clause 48, wherein the adjunctive agent includes one or more analgesics for pain.

Clause 50. The device of Clause 48 or Clause 49, wherein the adjunctive agent includes one or more anti-inflammatory agents for inflammation.

Clause 51. The device of any one of Clauses 1-50, wherein the therapeutic region includes a therapeutically effective dose of the chemotherapeutic agent and wherein the film is configured to release the chemotherapeutic agent for a sustained period of time.

Clause 52. The device of any one of Clauses 1-51, wherein the therapeutic region is configured to deliver a dose of the chemotherapeutic agent locally to the treatment site, and wherein the dose is higher than the dose received by the treatment site when the chemotherapeutic agent is delivered systemically.

Clause 53. The device of any one of Clauses 1-52, wherein the therapeutic region is configured to deliver a dose of the chemotherapeutic agent over a sustained period, wherein the sustained period if 1, 2, 3, 4, 5, 6, 7, or 8 weeks, or 1, 2, 3, 4, 5, 6, 9, 12, 15, or 18 months.

Clause 54. The device of any one of Clauses 1-53, wherein the therapeutic region is configured to deliver a continuous dose of the chemotherapeutic agent over a predetermined time period.

Clause 55. The device of any one of Clauses 1-53, wherein the therapeutic region is configured to deliver an intermittent dose of the chemotherapeutic agent over a predetermined time period.

Clause 56. The device of any one of Clauses 1-55, wherein the therapeutic member is configured to be secured at the treatment site via at least one of a suture, staple, glue, or hydrogel.

Clause 57. The device of any one of Clauses 1-56, wherein the device includes an anchoring member for securing the therapeutic member at the treatment site.

Clause 58. The device of Clause 57, wherein the anchoring member is integrated with or bonded to the therapeutic member.

Clause 59. The device of Clause 57, wherein the anchoring member is delivered after the therapeutic member is positioned.

Clause 60. The device of Clause 57 or Clause 59, wherein the anchoring member is an off the shelf, commercially available stent.

Clause 61. A system for treating a patient with esophageal cancer, the system comprising
  a delivery system;
  an implant configured for endoluminal placement via the delivery system into the esophagus of the patient, wherein the implant comprises:
    a therapeutic member comprising a treatment portion having a film for controlled release of a chemotherapeutic agent, the film comprising:
      a control region comprising a first polymer and releasing agent mixed with the polymer, wherein the releasing agent is configured to dissolve when the therapeutic member is placed in vivo to form channels in the control region;
      a therapeutic region comprising the chemotherapeutic agent mixed with a second polymer; and
      a substantially impermeable base region,
      wherein the film is configured to release the chemotherapeutic agent in a direction away from the substantially impermeable base region; and
    an anchoring member configured to provide structural support for the therapeutic member following endoluminal placement of the implant,
  wherein the delivery system is configured to enable a treatment provider to position the therapeutic region of the therapeutic member proximate to a treatment site associated with the esophagus of the patient, wherein the therapeutic member is configured to administer a therapeutically effective dose to the treatment site for a sustained period following endoluminal placement of the implant in the esophagus of the patient.

Clause 62. The system of Clause 61, wherein the anchoring member is a stent having sufficient radial resistance to provide structural integrity to the esophageal lumen.

Clause 63. The system of Clause 61 or Clause 62, wherein the anchoring member is configured to prevent and/or slow penetration of the tumor into the lumen.

Clause 64. The system of any one of Clauses 61-63, wherein the anchoring member and therapeutic member have a relative orientation such that upon deployment of the implant, the anchoring member is positioned directly adjacent to the treatment site and the treatment portion of the therapeutic member is configured to release the chemotherapeutic agent through openings in the anchoring member to the treatment site.

Clause 65. The system of any one of Clauses 61-64, wherein the anchoring member is configured to facilitate engagement between the esophagus of the patient and the anchoring member to minimize migration of the implant along the esophagus of the patient.

Clause 66. The system of any one of Clauses 61-65, wherein the anchoring member and the therapeutic member have a relative orientation such that upon deployment of the implant, the therapeutic member is positioned directly adjacent to the treatment site.

Clause 67. The system any one of Clauses 61-66, wherein the implant comprises a modular system that includes multiple components configured for coordinated placement within the esophagus of the patient.

Clause 68. The system of Clause 67, wherein the modular system comprises anchoring member components, therapeutic member components and/or integrated components having both a therapeutic member and an integrated anchoring member.

Clause 69. The system of any one of Clauses 61-68, wherein the therapeutic member is configured to release the chemotherapeutic agent (a) about 360 degrees of at the treatment site or (b) less than 360 degrees for focal release of chemotherapeutic agent.

Clause 70. The system of any one of Clauses 61-69, wherein the therapeutic member and/or anchoring member is configured to be delivered in a subsequent procedure to "touch up" an area requiring treatment or to address at least one of a subsequently developed stricture, obstruction, tumor, and lesion.

Clause 71. The system of any one of Clauses 61-70, wherein the combination of radial resistance (or chronic outward force) from the anchoring member and the release of chemotherapeutic agent from the therapeutic member provide a synergistic clinical benefit to the treatment site.

Clause 72. A method of treating a patient diagnosed with cancer, the method comprising:
  endoluminal delivery of a treatment device to a treatment site in the patient, the treatment device comprising an implant and a delivery system;
  positioning the implant proximate to the treatment site, the implant comprising a therapeutic member and an anchoring member;
  deploying the implant such that a treatment portion of the therapeutic member is adjacent to the treatment site and the anchoring member provides a stabilizing force to the treatment site;
  withdrawing the delivery system from the patient and leaving the implant proximate to the treatment site and the treatment portion of the therapeutic member adjacent to the treatment site;
  delivering via the treatment portion of the therapeutic member a chemotherapeutic agent to the treatment device for a sustained period of time; and
  wherein delivering the chemotherapeutic agent occurs following withdrawal of the delivery system from the patient.

Clause 73. The method of Clause 72 wherein delivery of the chemotherapeutic agent via the therapeutic member and the stabilizing force of the anchoring member provide a synergistic clinical benefit to the treatment site.

Clause 74. The method of Clause 72 or Clause 73 wherein treating a patient diagnosed with cancer comprises treating the patient for esophageal cancer.

Clause 75. The method of any one of Clauses 72-74 wherein placement of the therapeutic member adjacent to the treatment site comprises placement of the therapeutic member adjacent to the esophagus of the patient.

Clause 76. The method of any one of Clauses 72-75 wherein placement of the therapeutic region includes positioning the implant adjacent to at least one of a tumor, lesion, stricture, and/or obstruction in the esophagus of the patient.

Clause 77. The method of any one of Clauses 72-76 wherein treating esophageal cancer comprises palliating and/or treating at least one symptom associated with the esophageal cancer.

Clause 78. The method of Clause 77 wherein the symptom is dysphagia.

Clause 79. The method of Clause 77 or Clause 78 wherein the symptom is pain.

Clause 80. An esophageal stent system for treating a patient with esophageal cancer, the esophageal stent system comprising:
a delivery system;
an implant configured for endoluminal deployment via the delivery system into the esophagus of the patient, wherein the implant comprises:
a therapeutic member having a treatment portion comprising a film for controlled release of a chemotherapeutic agent, the film comprising:
a control region comprising a bioresorbable polymer and a releasing agent mixed with the bioresorbable polymer, wherein the releasing agent is configured to dissolve when the therapeutic member is placed in vivo to form diffusion channels in the control region;
a therapeutic agent region comprising the chemotherapeutic agent mixed with the bioresorbable polymer and the releasing agent;
a substantially impermeable base region comprising the bioresorbable polymer, and
wherein the film is configured to release the chemotherapeutic agent in a direction away from the substantially impermeable base region;
a stent configured for expansion during endoluminal deployment of the implant,
wherein the delivery system is configured to enable a treatment provider to position the treatment portion of the therapeutic member proximate to a treatment site corresponding to a tumor in the esophagus of the patient, and
wherein the treatment portion of the therapeutic member is configured to administer a therapeutically effective dose to the treatment site for a sustained period following endoluminal placement of the implant in the esophagus of the patient, and
wherein the stent is configured to provide structural support to the treatment site following endoluminal deployment of the implant, and
wherein the therapeutic member and stent are configured to provide a synergistic combination of chemotherapeutic agent and structural support to the treatment site.

Clause 80. A method of treating a patient diagnosed with cancer with any of the devices or systems of Clauses 1-71 and 80.

Clause 81. A device for treating a patient with cancer of a body lumen, the device comprising:
a therapeutic member configured for endoluminal placement in the body lumen of the patient, wherein the therapeutic member comprises a treatment portion for controlled release of a chemotherapeutic agent, the treatment portion comprising:
a therapeutic region comprising the chemotherapeutic agent, a polymer, and a releasing agent, wherein the chemotherapeutic agent and the releasing agent are mixed with the polymer, and wherein the releasing agent is configured to dissolve when the therapeutic member is placed in vivo to form diffusion openings in the therapeutic region;
a substantially impermeable base region,
wherein the treatment portion is configured to release the chemotherapeutic agent in a direction away from the substantially impermeable base region, and
wherein the therapeutic member is configured to be endoluminally positioned within the body lumen such that the treatment portion of the therapeutic member is proximate to a treatment site associated with the body lumen of the patient, and wherein the therapeutic member is configured to administer a therapeutically effective dose to the treatment site for a sustained period following endoluminal placement of the therapeutic member.

Clause 81a. The device of Clause 81, wherein the body lumen is a portion of the gastrointestinal tract.

Clause 81b. The device of Clause 81 or Clause 81a, wherein the body lumen is the esophagus.

Clause 82. The device of any one of Clauses 81 to 81b, wherein the therapeutic member is configured to be positioned such that the base region is closer to the center of the lumen than the therapeutic region.

Clause 83. The device of any one of Clauses 81 to 82, further comprising a control region having a polymer mixed with a releasing agent, and wherein a portion of the base region extends laterally even with or beyond the control region, and wherein the portion provides a seal to minimize the loss of therapeutic agent down the lumen.

Clause 84. The device of any one of Clauses 81 to 83, wherein the treatment portion is configured such that, when implanted, it extends around less than the full circumference of the body lumen at the treatment site.

Clause 85. The device of any one of Clauses 81 to 84, wherein the therapeutic member is configured such that, when implanted, it extends around less than the full circumference of the body lumen at the treatment site.

Clause 86. The device of any one of Clauses 81 to 85, wherein the therapeutic member is a first therapeutic member, and the device further includes a second therapeutic member.

Clause 87. The device of any one of Clauses 81 to 86, wherein the treatment portion comprises the entirety of the therapeutic member.

Clause 88. The device of any one of Clauses 81 to 87, wherein the treatment portion comprises less than the entire therapeutic member such that the treatment portion is a distinct region along the length and/or circumference of the therapeutic member.

Clause 89. The device of Clause 88, wherein the treatment portion extends along only a portion of the length of the therapeutic member.

Clause 90. The device of Clause 88, wherein the treatment portion extends along only a portion of the circumference of the therapeutic member.

Clause 91. The device of any one of Clauses 81 to 90, wherein the treatment portion extends along no more than 30, 60, 90, 120, 150, or 180 degrees of the therapeutic member.

Clause 92. The device of any one of Clauses 81 to 91, wherein the therapeutic member includes multiple treatment portions that are longitudinally and/or radially spaced apart.

Clause 93. The device of any one of Clauses 81 to 92, wherein the therapeutic member is configured to be removed following a predefined period of time.

Clause 94. The device of any one of Clauses 81 to 93, wherein the therapeutic member is a first therapeutic member, and the device is configured such that the first therapeutic member is interchangeable with a second therapeutic member having the same or different type of chemotherapeutic agent and/or the same or different amount of chemotherapeutic agent.

Clause 95. The device of Clause, wherein the treatment portion is a first treatment portion, and the device is configured such that the first treatment portion is interchangeable with a second treatment portion having the same or different type of chemotherapeutic agent and/or the same or different amount of chemotherapeutic agent.

Clause 96. The device of any one of Clauses 81 to 95, wherein the therapeutic member comprises a film.

Clause 97. The device of any one of Clauses 81 to 96, wherein the therapeutic region comprises a multilayer structure.

Clause 98. The device of any one of Clauses 81 to 97, wherein the therapeutic region comprises a plurality of microlayers.

Clause 99. The device of any one of Clauses 81 to 99, wherein the therapeutic region includes at least a 0.5:1, a 1:1, at least a 1.5:1, at least a 2:1, at least a 2.5:1, at least a 3:1, at least a 3.5:1, or at least a 4:1 ratio of drug to polymer.

Clause 100. The device of any one of Clauses 81 to 99, wherein the therapeutic region includes at least a 1:4, at least a 1:3, or at least a 1:2 ratio of releasing agent to drug.

Clause 101. The device of any one of Clauses 81 to 100, wherein the releasing agent is a non-ionic surfactant.

Clause 102. The device of any one of Clauses 81 to 101, wherein the releasing agent has hydrophilic properties.

Clause 103. The device of any one of Clauses 81 to 102, wherein the releasing agent is a polysorbate.

Clause 104. The device of any one of Clauses 81 to 103, wherein the releasing agent is Tween 20.

Clause 105. The device of any one of Clauses 81 to 104, wherein the releasing agent is Tween 80.

Clause 106. The device of any one of Clauses 81 to 105, wherein the releasing agent is non-polymeric.

Clause 107. The device of any one of Clauses 81 to 106, wherein the releasing agent is not a plasticizer.

Clause 108. The device of any one of Clauses 81 to 107, wherein the therapeutic region and/or treatment portion is configured to release an adjunctive agent.

Clause 109. The device of Clause 108, wherein the adjunctive agent includes one or more analgesics for pain.

Clause 110. The device of Clause 108 or Clause 109, wherein the adjunctive agent includes one or more anti-inflammatory agents for inflammation.

Clause 111. The device of any one of Clauses 108 to 110, wherein the adjunctive agent includes one or more vasoconstrictors to increase local absorption of the chemotherapeutic agent.

Clause 112. The device of any one of Clauses 81 to 111, wherein the polymer is bioabsorbable.

Clause 113. The device of any one of Clauses 81 to 112, wherein the polymer is non-biodegradable.

Clause 114. The device of any one of Clauses 81 to 113, wherein the polymer is poly(lactide-co-caprolactone) (PLCL).

Clause 115. The device of Clause 114, wherein the polymer includes at least one of polyglycolide (PGA), polycaprolactone (PCL), poly(L-lactic acid) (PLA), poly (alpha-hydroxy acids), poly(lactide-co-glycolide)(PLGA or DLG), poly(DL-lactide-co-caprolactone) (DL-PLCL), poly-caprolactone (PCL), poly(L-lactic acid) (PLA), poly(trimethylene carbonate) (PTMC), polydioxanone (PDO), poly (4-hydroxy butyrate) (PHB), polyhydroxyalkanoates (PHA), poly(phosphazene), polyphosphate ester), poly (amino acid), polydepsipeptides, poly(butylene succinate) (PBS), polyethylene oxide, polypropylene fumarate, poly-iminocarbonates, poly(lactide-co-caprolactone) (PLCL), poly(glycolide-co-caprolactone) (PGCL) copolymer, poly (D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly (glycolide-co-carolactone) (PGCL), poly(ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethyl-cellulose or salts thereof, Carbopol®, poly(hydroxyethyl-methacrylate), poly(methoxyethylmethacrylate), poly (methoxyethoxy-ethylmethacrylate), polymethylmethacrylate (PMMA), methylmethacrylate (MMA), gelatin, polyvinyl alcohols, and propylene glycol.

Clause 116. The device of any one of Clauses 81 to 115, wherein the polymer is a first polymer and the base region includes a second polymer.

Clause 117. The device of Clause 116, wherein the first polymer and the second polymer are the same.

Clause 118. The device of Clause 117, wherein the first polymer and the second polymer are different.

Clause 119. The device of any one of Clauses 116 to 118, wherein both the first and second polymer are bioabsorbable.

Clause 120. The device of any one of Clauses 116 to 119, wherein at least one of the first polymer and the second polymer is non-biodegradable.

Clause 121. The device of Clause 116, wherein both of the first polymer and the second polymer are non-biodegradable.

Clause 122. The device of any one of Clauses 116 to 121, wherein the second polymer has a longer degradation period than the first polymer.

Clause 123. The device of any one of Clauses 116 to 121, wherein the first polymer has a longer degradation period than the second polymer.

Clause 124. The device of any one of Clauses 116 to 123, wherein the first polymer and/or the second polymer is poly(lactide-co-caprolactone) (PLCL).

Clause 125. The device of any one of Clauses 116 to 124, wherein the first polymer and/or the second polymer include at least one of polyglycolide (PGA), polycaprolactone (PCL), poly(L-lactic acid) (PLA) Suitable additional bioresorbable polymers and copolymers for use in the present invention include, but are not limited to, poly(alpha-hydroxy acids), poly(lactide-co-glycolide)(PLGA or DLG), poly (DL-lactide-co-caprolactone) (DL-PLCL), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly (lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly (gycolide-trimethylene carbonate), poly(glycolide-co-carolactone) (PGCL), poly(ethyl glutamate-co-glutamic acid), poly(tert-butyloxy-carbonylmethyl glutamate), poly (glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly (methoxyethoxy-ethylmethacrylate), polymethylmethacrylate (PMMA), methylmethacrylate (MMA), gelatin, polyvinyl alcohols, and propylene glycol.

Clause 126. The device of any one of Clauses 81 to 125, wherein the polymer is a monomer, co-polymer or terpolymer.

Clause 127. The device of any one of Clauses 81 to 126, wherein the first and/or second polymers have a degradation profile of 3, 6, 9, 12, 15, or 18 months.

Clause 128. The device of any one of Clauses 81 to 127, wherein the first and/or second polymers are non-bioresorbable polymers comprising at least one of polyurethane, silicone, and poly(ethylene vinyl acetate) (PEVA).

Clause 129. The device of any one of Clauses 81 to 128, wherein the chemotherapeutic agent includes at least one of the chemotherapeutic agents identified in Table 1.

Clause 130. The device of any one of Clauses 81 to 129, wherein the chemotherapeutic agent comprises multiple agents for combination or sequential dosing.

Clause 131. The device of any one of Clauses 81 to 130, wherein the therapeutic region includes multiple chemotherapeutic agents.

Clause 132. The device of Clause 131, wherein the treatment portion comprises multiple layers, and wherein the multiple chemotherapeutic agents are contained in separate layers.

Clause 133. The device of Clause 132, wherein the multiple chemotherapeutic agents are contained within the same layer of the multilayer structure.

Clause 134. The device of any one of Clauses 81 to 133, wherein the therapeutic region is configured to deliver a dose of the chemotherapeutic agent locally to the treatment site, and wherein the dose is higher than the dose received by the treatment site when the chemotherapeutic agent is delivered systemically.

Clause 135. The device of any one of Clauses 81 to 134, wherein the therapeutic region is configured to release the chemotherapeutic agent for at least 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, 12, months, 13 months, 14 months, 15 months, 16 months, 17 months, or 18 months.

Clause 136. The device of any one of Clauses 81 to 135, wherein the therapeutic region is configured to deliver a continuous dose of the chemotherapeutic agent over a predetermined time period.

Clause 137. The device of Clause 136 wherein the predetermined time period is at least 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, 12, months, 13 months, 14 months, 15 months, 16 months, 17 months, or 18 months.

Clause 138. The device of any one of Clauses 81 to 137, wherein the therapeutic region is configured to deliver an intermittent dose of the chemotherapeutic agent over a predetermined time period.

Clause 139. The device of Clause 138 wherein the predetermined time period is at least 3 days, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, 12, months, 13 months, 14 months, 15 months, 16 months, 17 months, or 18 months.

Clause 140. The device of any one of Clauses 81 to 139, wherein the therapeutic region, the treatment portion, and/or the therapeutic member carry at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, and at least 1000 mg of chemotherapeutic agent.

Clause 141. The device of any one of Clauses 81 to 140, wherein the therapeutic region releases 5%, 10%, 15%, 20%, 25%, 30%, 35%, 40%, 50% 55%, 60%, 65%, 70%, 75%, 80%, 85%, 90%, 95%, 99%, 100% of the chemotherapeutic agent over a period of 1 day to 6 months, 5 days to 5 months, 10 days to 4 months, 20 days to 3 months, or 1 month to 2 months 2 months to 8 months, 3 months to 9 months, 4 months to 10 months, 5 months to 11 months, 3 months to 12 months, 3 months to 13 months, 2 months to 14 months, 2 months to 15 months, or 3 months to 16 months after the therapeutic member is implanted in the lumen.

Clause 142. The device of any one of Clauses 81 to 141, wherein the therapeutic member releases no more than 50% of the chemotherapeutic agent therein over the first 2 weeks, 3 weeks, 4 weeks, 5 weeks, 6 weeks, 8 weeks, 3 months, 4 months, 5 months, 6 months, 7 months, or 8 months.

Clause 143. The device of any one of Clauses 81 to 142, wherein the therapeutic member comprises a strip having an expanded state in which the strip curls around a central longitudinal axis such that, when the therapeutic member is implanted within the lumen, the strip curves around and is in contact with an inner surface of the wall defining the body lumen.

Clause 144. The device of Clause 143, wherein the strip curves around only a portion of the circumference of the body lumen wall in the expanded state.

Clause 145. The device of Clause 143, wherein the strip curves around at least the entire circumference of the body lumen wall in the expanded state.

Clause 146. The device of Clause 143, wherein the strip extends between two longitudinal ends, and wherein the ends of the strip are spaced apart when the strip is curled in the expanded state.

Clause 147. The device of Clause 143, wherein the strip extends between two longitudinal ends, and wherein the ends of the strip overlap when the strip is curled in the expanded state.

Clause 148. The device of Clause 143, wherein the strip has a width extending between lateral edges.

Clause 149. The device of Clause 143, wherein, when the in the expanded state, the strip forms a spiral shape.

Clause 150. The device of Clause 143, wherein, when in a delivery state, the strip forms a substantially linear shape and when in the expanded state, the strip forms a spiral shape.

Clause 151. The device of Clause 143, wherein, when in the expanded state, the strip forms a series of helical windings.

Clause 152. The device of Clause 151, wherein the lateral edges of adjacent helical windings are spaced apart in the expanded state.

Clause 153. The device of Clause 151, wherein the lateral edges of at least some of the adjacent helical windings overlap in the expanded state.

Clause 154. The device of Clause 151, wherein the lateral edges of at least some of the adjacent helical windings abut in the expanded state.

Clause 155. The device of Clause 151, wherein the lateral edges of adjacent helical windings are spaced apart in the expanded state, and wherein the strip has a collapsed configuration for delivery through a catheter lumen to the treatment site, the lateral edges of adjacent helical windings being closer together in the collapsed state than in the expanded state.

Clause 156. The device of any one of Clauses 81 to 155, wherein the therapeutic member is a sleeve.

Clause 157. The device of any one of Clauses 81 to 156, wherein the therapeutic member is a band.

Clause 158. The device of any one of Clauses 81 to 157, wherein the therapeutic member is a cuff.

Clause 159. The device of any one of Clauses 81 to 158, wherein the device includes a support member for securing the therapeutic member at the treatment site.

Clause 160. The device of Clause 159, wherein the support member is integrated with or bonded to the treatment portion.

Clause 161. The device of Clause 159 or Clause 160, wherein the support member is only coupled to a periphery of the treatment portion.

Clause 161a. The device of any one of Clauses 159 to 161, wherein the support member is positioned radially outwardly of the treatment portion such that the support member is between the treatment portion and the tumor and/or the body lumen when the device is implanted within the body lumen.

Clause 161b. The device of any one of Clauses 159 to 161a, wherein the support member is surrounded by the treatment portion.

Clause 162. The device of any one of Clauses 81 to 161, wherein:
the therapeutic member includes a protruding portion that extends radially away from the therapeutic member and into adjacent esophageal tissue when the therapeutic member is implanted at the treatment site, and
the therapeutic member is configured to administer the chemotherapeutic agent at a depth within the esophageal wall.

Clause 163. The device of Clause 162, wherein the protruding portion terminates within mucosal tissue.

Clause 164. The device of Clause 162, wherein the protruding portion terminates at a depth within the esophageal wall between mucosal tissue and submucosal tissue.

Clause 165. The device of Clause 162, wherein the protruding portion terminates within submucosal tissue.

Clause 166. The device of Clause 162, wherein the protruding portion terminates at a depth within the esophageal wall between submucosal tissue and muscle tissue.

Clause 167. The device of Clause 162, wherein the protruding portion terminates within muscle tissue.

Clause 168. The device of Clause 162, wherein the therapeutic member is configured to administer the chemotherapeutic agent to mucosal tissue of the esophageal wall.

Clause 169. The device of Clause 162, wherein the therapeutic member is configured to administer the chemotherapeutic agent to submucosal tissue of the esophageal wall.

Clause 170. The device of Clause 162, wherein the therapeutic member is configured to administer the chemotherapeutic agent to an annular space between a submucosal layer and a muscle layer of the esophageal wall.

Clause 171. The device of Clause 162, wherein the protruding portion is substantially linear.

Clause 172. The device of Clause 162, wherein the protruding portion is configured to curve as it extends into the esophageal tissue.

Clause 173. The device of Clause 172, wherein the protruding portion curves around at least a portion of an annular space between a submucosal layer and a muscle layer of the esophageal wall.

Clause 174. The device of any one of Clauses 81 to 173, wherein the treatment portion further includes a control region comprising a polymer and a releasing agent.

Clause 175. The device of Clause 174 wherein the control region does not include the chemotherapeutic agent.

Clause 176. The device Clause 174 or Clause 175, wherein the control region completely encapsulates the therapeutic region.

Clause 177. The device of any one of Clauses 174 to 176, wherein the control region covers only a portion of the therapeutic region.

Clause 178. The device of any one of Clauses 174 to 177, wherein the control region is positioned between at least a portion of the therapeutic region and at least a portion of the base region.

Clause 179. The device of any one of Clauses 174 to 178, wherein the therapeutic region is positioned between at least a portion of the control region and at least a portion of the base region.

Clause 180. The device of any one of Clauses 174 to 179, wherein the polymer in the control region is the same as the polymer in the therapeutic region.

Clause 181. The device of any one of Clauses 174 to 179, wherein the polymer in the control region is different than the polymer in the therapeutic region.

Clause 182. The device of any one of Clauses 174 to 181, wherein the amount of releasing agent in the control region is the same amount of releasing agent in the therapeutic region.

Clause 183. The device of any one of Clauses 174 to 181, wherein the amount of releasing agent in the control region is different than the amount of releasing agent in the therapeutic region.

Clause 184. The device any of any one of Clauses 174 to 182, wherein the control region is a first control region, and wherein the treatment portion includes a second control region.

Clause 185. The device of any one of Clauses 174 to 184, wherein the first control region has the same polymer as the second control region.

Clause 186. The device of any one of Clauses 174 to 184, wherein the first control region has a different polymer than the second control region.

Clause 187. The device of any one of Clauses 174 to 186, wherein the first control region has a different amount of releasing agent than the second control region.

Clause 188. The device of any one of Clauses 174 to 186, wherein the first control region has a different amount of releasing agent than the second control region.

Clause 189. The device of any one of Clauses 81 to 188, wherein the first control region has a different amount of releasing agent than the second control region.

Clause 190. The device of any one of Clauses 174 to 189, wherein the treatment portion includes a plurality of control regions, and wherein at least one of the control regions has a different amount of releasing agent and/or a different polymer than another one of the control regions.

Clause 191. The device of any one of Clauses 174 to 190, wherein the polymer in the control region includes one or more of the polymers of Clause 115.

Clause 192. A system for treating a patient with cancer within a body lumen, the system comprising:
an implant configured for endoluminal placement via the delivery system into the body lumen of the patient, wherein the implant comprises:
a therapeutic member comprising a treatment portion for controlled release of a chemotherapeutic agent, the treatment portion comprising:
a therapeutic region comprising the chemotherapeutic agent, a polymer and a releasing agent, wherein the chemotherapeutic agent, the polymer, and the releasing agent are mixed together, wherein the releasing agent is configured to dissolve when the therapeutic member is placed in vivo to form channels in the control region;
a substantially impermeable base region,
wherein the treatment portion is configured to release the chemotherapeutic agent in a direction away from the substantially impermeable base region; and
an anchoring member configured to provide structural support for the therapeutic member following endoluminal placement of the implant,
wherein the therapeutic member is configured to administer a therapeutically effective dose to the treatment site for a sustained period following endoluminal placement of the implant in the body lumen of the patient.

Clause 193. The system of Clause 192, wherein the body lumen is an esophagus.

Clause 194. The system of Clause 192 or Clause 193, wherein the body lumen is a portion of the gastrointestinal tract.

Clause 195. The system of any one of Clauses 192 to 194, wherein the therapeutic member is any of the therapeutic members of Clauses 81 to 191.

Clause 196. The system of any one of Clauses 192 to 195, further comprising a delivery system that is configured to enable a treatment provider to position the therapeutic region of the therapeutic member proximate to a treatment site associated with the body lumen of the patient.

Clause 197. The system of any one of Clauses 192 to 196, wherein the anchoring member is a stent having sufficient radial resistance to provide structural integrity to the esophageal lumen.

Clause 198. The system of any one of Clauses 192 to 197, wherein the anchoring member is configured to prevent and/or slow penetration of the tumor into the lumen.

Clause 199. The system of any one of Clauses 192 to 198, wherein the anchoring member and therapeutic member have a relative orientation such that upon deployment of the implant, the anchoring member is positioned directly adjacent to the treatment site and the treatment portion of the therapeutic member is configured to release the chemotherapeutic agent through openings in the anchoring member to the treatment site.

Clause 200. The system of any one of Clauses 192 to 199, wherein the anchoring member and the therapeutic member have a relative orientation such that upon deployment of the implant, the therapeutic member is positioned directly adjacent to the treatment site.

Clause 201. The system of any one of Clauses 192 to 200, wherein the implant comprises a modular system that includes multiple components configured for coordinated placement within the body lumen of the patient.

Clause 202. A method of treating a patient diagnosed with cancer, the method comprising:
endoluminal delivery of a treatment device to a treatment site in the patient, the treatment device comprising an implant and a delivery system;
positioning the implant proximate to the treatment site, the implant comprising a therapeutic member and an anchoring member;
deploying the implant such that a treatment portion of the therapeutic member is adjacent to the treatment site and the anchoring member provides a stabilizing force to the treatment site;
withdrawing the delivery system from the patient and leaving the implant proximate to the treatment site and the treatment portion of the therapeutic member adjacent to the treatment site;
delivering via the treatment portion of the therapeutic member a chemotherapeutic agent to the treatment device for a sustained period of time; and
wherein delivering the chemotherapeutic agent occurs following withdrawal of the delivery system from the patient.

Clause 203. The method of Clause 202, further comprising administering a therapeutically effective dose to treat esophageal cancer.

Clause 204. The method of Clause 203, wherein administering the therapeutically effective dose provides palliation of dysphagia associated with the esophageal cancer.

Clause 205. The method of Clause 203 or Clause 204, wherein administering the therapeutically effective dose prevents growth of the tumor into the esophageal lumen.

Clause 206. The method of any one of Clauses 203 to 205, wherein administering the therapeutically effective dose prevents invasion by the tumor into the stent.

Clause 207. The method of any one of Clauses 203 to 206, wherein administering the therapeutically effective dose enhances durability of the stent by reducing and/or preventing overgrowth and/or ingrowth of the tumor, and/or migration of the stent.

Clause 208. The method of any one of Clauses 203 to 207, wherein administering the therapeutically effective dose causes local regression of the tumor.

Clause 209. The method of Clause 208, wherein the tumor is a squamous cell carcinoma.

Clause 210. The method of any one of Clauses 202 to 209, wherein the therapeutic member is any of the therapeutic members of Clauses 81-191.

Clause 211. An esophageal stent system for treating a patient with esophageal cancer, the esophageal stent system comprising:
a delivery system;
an implant configured for endoluminal deployment via the delivery system into the esophagus of the patient, wherein the implant comprises:
a therapeutic member having a treatment portion comprising a film for controlled release of a chemotherapeutic agent, the film comprising:
a control region comprising a bioresorbable polymer and a releasing agent mixed with the bioresorbable polymer, wherein the releasing agent is configured to dissolve when the therapeutic member is placed in vivo to form diffusion channels in the control region;
a therapeutic agent region comprising the chemotherapeutic agent mixed with the bioresorbable polymer and the releasing agent;
a substantially impermeable base region comprising the bioresorbable polymer, and
wherein the film is configured to release the chemotherapeutic agent in a direction away from the substantially impermeable base region;
a stent configured for expansion during endoluminal deployment of the implant,
wherein the delivery system is configured to enable a treatment provider to position the treatment portion of the therapeutic member proximate to a treatment site corresponding to a tumor in the esophagus of the patient, and
wherein the treatment portion of the therapeutic member is configured to administer a therapeutically effective dose to the treatment site for a sustained period following endoluminal placement of the implant in the esophagus of the patient, and
wherein the stent is configured to provide structural support to the treatment site following endoluminal deployment of the implant, and
wherein the therapeutic member and stent are configured to provide a synergistic combination of chemotherapeutic agent and structural support to the treatment site.

Clause 212. The system of Clause 211, wherein the therapeutic member is any of the therapeutic members of Clauses 81 to 191.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 2A is a cross-sectional view of a treatment device in accordance with the present technology, shown positioned adjacent a tumor within the esophagus of a patient.

FIGS. 2B and 2C are cross-sectional end views of different configurations of the treatment device shown in FIG. 2A.

FIG. 3 is an enlarged cross-sectional view of a portion of the treatment device shown in FIG. 2A.

FIG. 4A is a cross-sectional view of a treatment device in accordance with the present technology, shown positioned adjacent a tumor within the esophagus of a patient.

FIGS. 4B and 4C are cross-sectional end views of different configurations of the treatment device shown in FIG. 4A.

FIG. 5 is an enlarged cross-sectional view of a portion of the treatment device shown in FIG. 4A.

FIG. 16A is a front view of a treatment device in accordance with the present technology.

FIGS. 16B-16E are cross-sectional end views of different expandable member configurations in accordance with the present technology.

FIGS. 36-45 are cross-sectional views of a treatment portion in accordance with the present technology.

DETAILED DESCRIPTION

Figure 1:
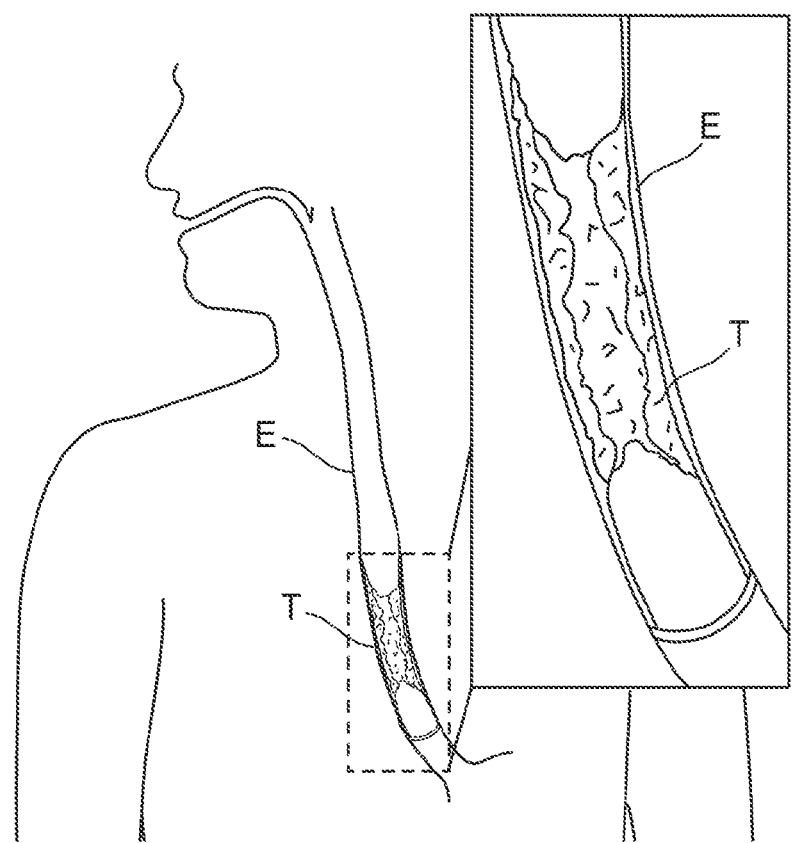
FIG. 1 is a schematic illustration of a portion of the upper gastrointestinal tract of a human patient, with an enlarged, cross-sectional view of an esophageal tumor.

Certain specific details are set forth in the following description and in FIGS. 2A-51B to provide a thorough understanding of various embodiments of the technology. For example, many embodiments are described below with respect to treating esophageal cancer and/or treating the symptoms of esophageal cancer. In other applications and other embodiments, however, the technology can be used to treat other intraluminal cancers, especially those arising within the gastrointestinal tract between the mouth and the stomach (e.g., stomach/gastric cancer, colorectal cancer, duodenal cancer). For example, the devices, systems, and methods disclosed herein can be used to in the throat region to treat pharyngeal cancer or in the bronchial tree to treat lung cancer. Other details describing well-known structures and systems often associated with stents and associated delivery devices and procedures have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 2A-51B.

I. Selected Embodiments of Treatment Devices

FIG. 2A is a cross-sectional view of a treatment device 10 in accordance with the present technology, shown in an expanded state positioned adjacent a tumor T within the esophagus E of a patient. FIG. 2B is a cross-sectional end view of the treatment device 10 shown in FIG. 2A. As shown in FIGS. 2A and 2B, in some embodiments the treatment device 10 includes an anchoring member 100 and a therapeutic member 102 carried on an inner surface of the anchoring member 100. The anchoring member 100 may be a generally tubular structure configured to expand from a low-profile state to a deployed state in apposition with a treatment site (e.g., the tumor T and/or esophageal wall EW). In the embodiment shown in FIGS. 2A and 2B, the anchoring member 100 does not include a polymer cover on its exterior surface such that the material comprising the tubular structure is exposed and in direct contact with the tumor T and/or the esophageal wall EW. The anchoring member 100 is configured to provide structural support to the treatment device 10, engage the tumor T and/or esophageal wall EW to secure the treatment device 10 to a selected region of the esophagus E, as well as bolster the integrity of the esophageal wall EW.

In some embodiments, the therapeutic member 102 is bonded or otherwise adhered to the inner surface of the anchoring member 100. In other embodiments, the treatment device may include a therapeutic member 102 without an anchoring member 100. The therapeutic member 102 may comprise a biocompatible carrier loaded with one or more therapeutic agents and configured for a controlled, sustained release of the therapeutic agent(s) following in vivo placement of the therapeutic member. In some embodiments, the therapeutic member may be a thin, multilayer film loaded with a therapeutic agent, wherein, as described in greater detail below, the therapeutic member 102 is configured to release the therapeutic agent(s) radially outwardly towards the tumor T, thereby inhibiting growth of the tumor T. In embodiments comprising a therapeutic member 102 and anchoring member 100, the combined effect of the therapeutic agent released from the therapeutic member and radial resistance (e.g., hoop strength, chronic outward force, etc.) of the anchoring member may prevent growth of the tumor T into the sidewall of the of the anchoring member 100 and towards the esophageal lumen L to prevent ingrowth of the tumor T and maintain luminal patency. In some embodiments it may be desirable to extend members 100 and 102 further down lumen L into the gastroesophageal junction, the junction between the esophagus and the stomach, and into the proximal stomach itself (not shown).

As depicted in FIGS. 2A and 2B, in some embodiments the tubular structure forming the anchoring member 100 may be a mesh structure. As used herein, "mesh" or "mesh structure" refers to any material (or combination of materials) having one or more openings extending therethrough. For example, in some embodiments, the anchoring member 100 comprises a plurality of filaments (e.g., wires, threads, sutures, fibers, etc.) that have been braided or woven into a tubular shape and heat set. In some embodiments, the mesh structure may be a stent formed of a laser-cut tube or laser-cut sheet, or the mesh structure may be a stent formed via thin film deposition. The anchoring member is in the form of a flat wire coil attached to a single longitudinal strut, a slotted tube, a helical band that extends circumferentially and longitudinally along the length of the anchoring member, a modular ring, a coil, a basket, a plurality of rings attached by one or more longitudinal struts, a braided tube surrounding a stent, a stent surrounding a braided tube, and/or any suitable configuration or embodiment disclosed herein.

In some embodiments, the anchoring member 100 may be formed of a superelastic material (e.g., nickel-titanium alloys, etc.) or other resilient materials such as stainless steel, cobalt-chromium alloys, etc. configured to self-expand when released from a delivery catheter. For example, the anchoring member may self-expand when pushed through the distal opening of the catheter, or by the delivery catheter being pulled proximally of the anchoring member. In some embodiments the anchoring member 100 may self-expand upon release from other constraining mechanisms (e.g., removable filaments, etc.). In some embodiments, the anchoring member 100 may be expanded manually (e.g., via balloon expansion, a push wire, a pull wire, etc.). When deployed, the anchoring member may apply a radially outward force on the tumor sufficient to increase luminal patency, thus providing immediate palliation of dysphagia.

In some embodiments, the anchoring member includes gold, magnesium, iridium, chromium, stainless steel, zinc, titanium, tantalum, and/or alloys of any of the foregoing metals or including any combination of the foregoing metals. In some embodiments, anchoring member may include collagen or other suitable bioresorbable or biodegradeable materials such as PLA, PLG, PLGA etc. In certain embodiments, the metal comprising the mesh structure may be highly polished and/or surface treated to further improve its hemocompatibility. The mesh structure may be constructed solely from metallic materials without the inclusion of any polymer materials, or may include a combination of polymer and metallic materials. For example, in some embodiments the anchoring member may include silicone, polyurethane, polyethylene, polyesters, polyorthoesters, polyanhyrides, and other suitable polymers. This polymer may form a complete tube to block passage of tumor or drug though the anchoring member, or it may have microscopic pores to allow passage of drug but not tumor cells, or it may have small or large openings. In addition, all or a portion of the anchoring member may include a radiopaque coating to improve visualization of the device during delivery, and/or the anchoring member may include one or more radiopaque markers.

The mesh structure may have a first end portion 100a, a second end portion 100b, and a body portion 100c extending between the first end portion 100a and the second end portion 100b. As shown in FIG. 2A, in some embodiments the first and/or second end portions 100a, 100b, may flare outwardly such that the average diameter of the anchoring member 100 along the body portion 100c is less than the average diameter of the individual first and/or second end portions 100a, 100b.

Figures 7A, 7B, 7C:
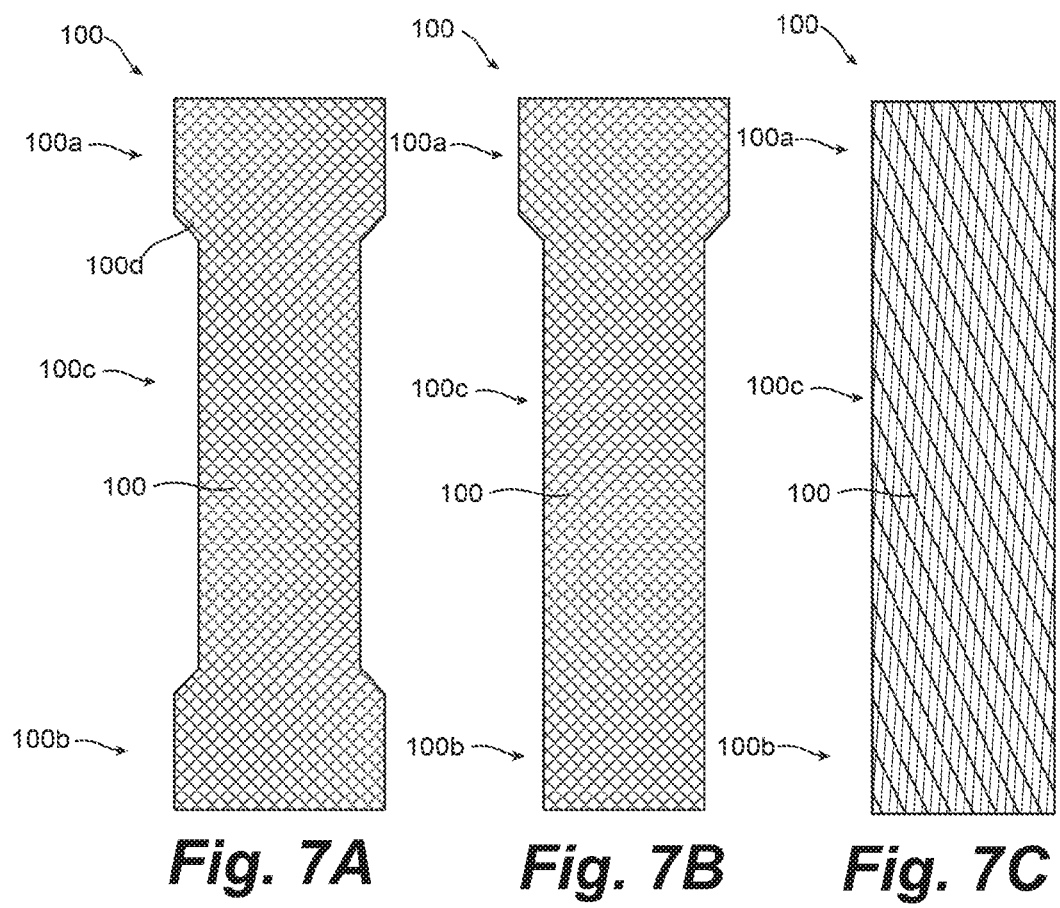
FIGS. 7A-7C show different anchoring members for use with the treatment devices of the present technology.
Figure 8A:
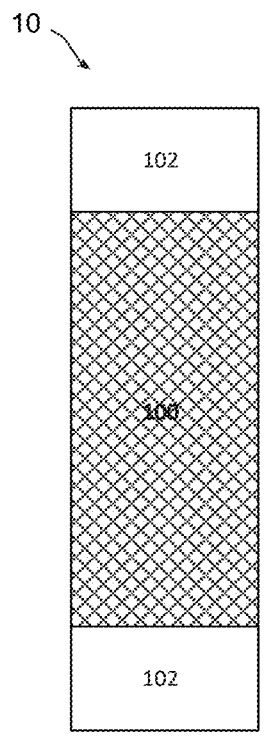
FIGS. 8A-8D show treatment devices in accordance with the present technology having different combinations of anchoring members and therapeutic members.
Figure 8B:
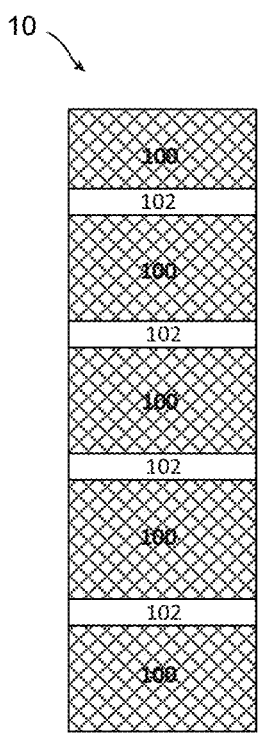
Figure 8C:
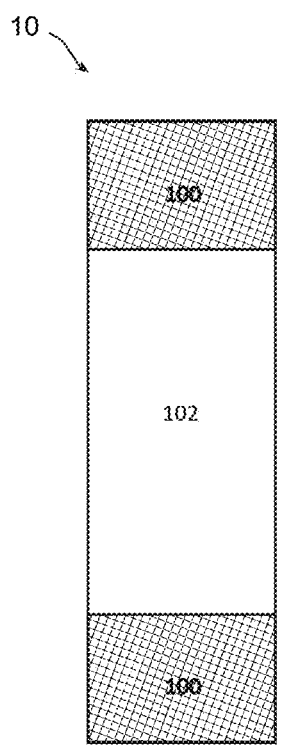
Figure 8D:
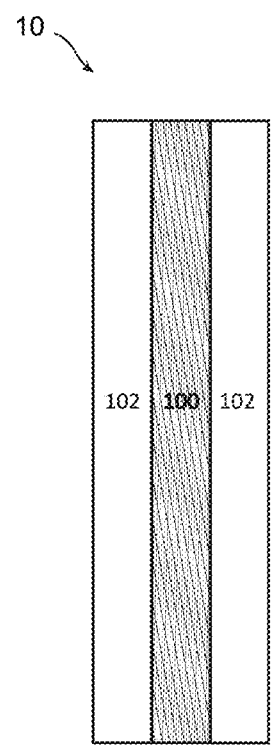

In some embodiments, the anchoring member 100 may have other suitable shapes, sizes, and configurations. For example, in some embodiments the anchoring member 100 may have a generally constant diameter along its length (i.e., no expanded end portions), as depicted in FIG. 7C. In some embodiments, only one of the first and second end portions 100a, 100b has a larger diameter, as shown in FIG. 7B. In several aspects of the technology, the mesh structure may include an intermediate region 100d between the body 100c and one or both of the first and/or second end portions 100a, 100b. For example, as depicted in FIG. 7A, in such embodiments the diameter of the intermediate region 100d tapers in the direction of the body 100c, and the first and second end portions 100a, 100b may have a generally constant diameter. To improve fixation, in some embodiments the anchoring member 100 may have one or more protrusions extending radially outwardly from the mesh structure along all or a portion of its length. For example, the anchoring member 100 may include one or more barbs, hooks, ribs, tines, and/or other suitable traumatic or atraumatic fixation members. In some embodiments, the anchoring member 100a/b may extend past the intermediate region 100d and extend over a portion of the body 100c (this area can remain uncovered to aid fixation without overgrowth).

Referring to FIG. 2A, the treatment device 10 is positioned within the esophageal lumen such that the first end portion 100a is positioned closer to the mouth along the gastrointestinal tract and the second end portion 100b is positioned closer to the stomach along the gastrointestinal tract. In some embodiments, the treatment device 10 may be positioned so that the first end portion 100a is closer to the stomach and the second portion 100b is closer to the mouth.

Additional examples of anchoring members suitable for use with the treatment devices and/or therapeutic members of the present technology may be embodied in commercially available esophageal stent systems, including, for example, Ultraflex™ (Boston Scientific), WALLSTENT™ (Boston Scientific), WallFlex™ (Boston Scientific), PolyFlex™ (Boston Scientific), Niti-S™ (Taewoong Medical), and others.

As previously mentioned, the therapeutic member 102 may be bonded or otherwise adhered to an inner surface of the anchoring member 100. For example, the therapeutic member 102 may be bonded to the anchoring member 100 by adhesive bonding, such as cyanoacrylate or UV curing medical grade adhesive, chemical or solvent bonding, and/or thermal bonding, and other suitable means. The therapeutic member 102 may also be sewn or riveted to the anchoring member 100. In some embodiments, the therapeutic member 102 may be woven into the anchoring member 100 at one or more sections of the anchoring member 100. In some embodiments, the anchoring member 100 may be dip coated in a solution comprising the material elements of the therapeutic member 102, and/or the anchoring member 100 may be spray coated with the therapeutic member 102. Sections of the anchoring member 100 may be selectively masked such that only certain portions of the anchoring member 100 may be coated with the therapeutic member 102. In some embodiments, the anchoring member 100 may be originally in the form of a sheet, and the sheet may be embedded into the therapeutic member 102 (for example, with the therapeutic member 102 as a multilayer film construction.) The resulting sheet structure (i.e., the anchoring member 100 embedded within the therapeutic member 102) may be rolled into a tubular structure (with or without the adjacent ends attached) for delivery into the body. In some embodiments, the therapeutic member may be coated with a bioresorbable adhesive derived from polyethylene glycol (PEG or PEO), for example, or from other hydrogels. The PEG or hydrogel may also be integral to the therapeutic member 102 via mixing in solution with the therapeutic member materials and not a separate coating.

The therapeutic member 102 may be disposed along all or a portion of the length of the mesh structure, all or a portion of the circumference of the mesh structure, and/or cover or span all or some of the openings in the mesh structure depending on the location of the tumor T and/or the local esophageal anatomy. For example, the volume, shape, and coverage of the tumor may vary patient-to-patient. In some cases, the tumor T may extend around the entire inner circumference of the esophagus E. In such a scenario, it may be desirable to use a treatment device having a therapeutic member 102 extending around the entire circumference of the anchoring member 100, as illustrated in FIG. 2B. In other cases, the tumor T may extend around only a portion of the inner circumference of the esophagus E. In this example, it may be desirable to use a treatment device having a therapeutic member 102 extending around less than the entire circumference of the anchoring member 100 (see FIG. 2C and FIG. 8D) to reduce exposure of potentially healthy tissue to the chemotherapeutic agents.

In some cases, this therapeutic member may be elastically expandable, such that a tubular therapeutic member expands with the anchoring member as it is deployed. It may also be less elastic but can be folded for delivery in a compact form. Alternatively, it could be configured to change shape as it is expanded. For example, a tubular therapeutic member could have a pattern of overlapping longitudinal slots, so that it expands into a diamond-shaped pattern as it is expanded. The expanded pattern of the therapeutic member may align with the pattern of the anchoring member, or it may be totally independent of the anchoring member. This approach may enable the highest volume of drug to be delivered in the most compact delivery format, while still enabling expansion on delivery and flexion, compression and expansion while swallowing.

Figure 9:
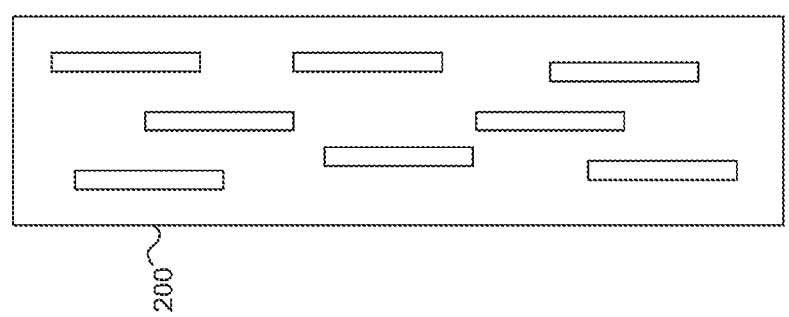
FIG. 9 is a front view of an anchoring member in accordance with the present technology.

In addition, the length of the therapeutic member 102 may be selected (relative to the length of the anchoring member 100) based on the length of the tumor T and/or the surface area of exposed anchoring member 100 desired for fixation. For example, the length of the therapeutic member 102 may be generally the same as the length of the anchoring member 100 (as shown in FIG. 2A), less than the length of the anchoring member 100 (see, for example, FIGS. 8A-8C), or greater than the length of the anchoring member 100. In some embodiments, the therapeutic member 102 may be disposed at different portions of the anchoring member 100 that are spaced apart along the length of the anchoring member 100 (i.e., longitudinally/axially staggered) (see, for example, FIGS. 8A-8C) and/or spaced apart about the circumference of the anchoring member 100 (i.e., circumferentially staggered) (see, for example, FIG. 8D). For example, in some embodiments the treatment device 10 may include a plurality of therapeutic members 102 in the form of circumferential bands spaced apart along the length of the anchoring member 100 (see, for example, FIGS. 8A and 8B). In several embodiments, the anchoring member 100 may comprise a tubular structure 200 having a plurality of longitudinal slots along its length, as depicted in FIG. 9. This slotted tubular structure allows the anchoring member to expand into a diamond pattern on delivery, and to expand, contract, and deform during swallowing. The increased pore size afforded by the slots may improve delivery of the therapeutic agent to the tumor.

In some embodiments, such as those depicted in FIGS. 2A and 2B, the therapeutic member 102 may cover the entirety of the inner surface of the mesh structure. In other words, in such embodiments, the therapeutic member 102 may be disposed along the entire length and complete circumference of the anchoring member 100, and span all of the openings in the mesh structure (as shown in FIG. 3). In some embodiments, the therapeutic member 102 covers or spans less than all the openings in the mesh structure. As shown in FIGS. 4A-5, in some embodiments the therapeutic member 102 may be disposed on an exterior surface of the anchoring member 100 such that the therapeutic member 102 is positioned radially outwardly of the anchoring member 100 when the treatment device 10 is positioned within the esophagus E.

Figure 6:
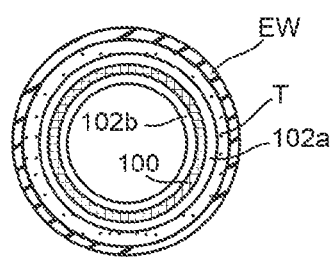
FIG. 6 is an end cross-sectional view of a treatment device in accordance with the present technology.

In some embodiments, the treatment device 10 may include two or more therapeutic members 102 (e.g., two therapeutic members, three therapeutic members, four therapeutic members, five therapeutic members, six therapeutic members, etc.). For example, as shown in FIG. 6, in some embodiments the treatment device 10 may include a first therapeutic member 102a disposed at the exterior surface of the anchoring member 100, and a second therapeutic member 102b disposed at the interior surface of the anchoring member 100. The first and second therapeutic members 102a, 102b may have the same or different therapeutic agent, the same or different degradation rate, the same or different dosage, etc. The outer anchoring member might be optimized to engage with the tissue of the esophageal wall to prevent migration, and the inner anchoring member might be optimized to hold the therapeutic member in place. The inner anchoring member might also have a continuous polymer membrane to prevent migration of therapeutic agent into the esophageal lumen.

Figure 10:
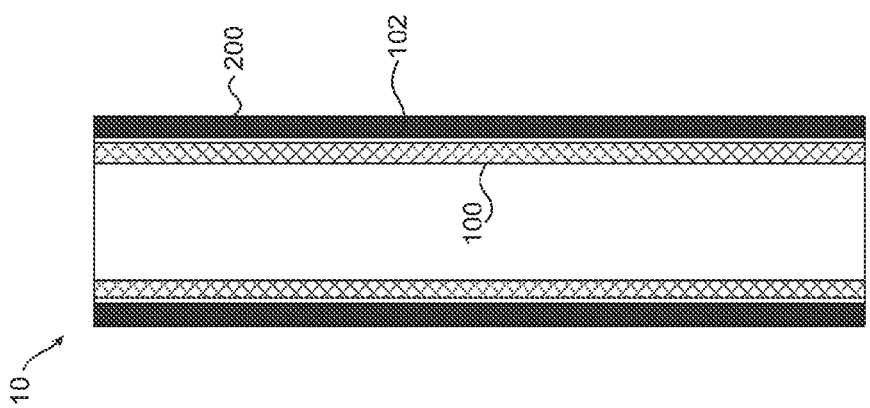
FIG. 10 is a front view of a treatment device including two anchoring members in accordance with the present technology.

In some embodiments, the treatment device 10 may include two or more anchoring members 100 (e.g., two anchoring members, three anchoring members, four anchoring members, five anchoring members, six anchoring members, etc.). For example, as shown in FIG. 10, in some embodiments the treatment device 10 may include an outer anchoring member 200 and an inner anchoring member 100 sandwiched between the outer and inner anchoring members 200, 100.

Referring to FIG. 3, the therapeutic member 102 may be a thin, flexible film configured for controlled release of a therapeutic agent when implanted in a patient. The therapeutic agent may include one or more chemotherapeutic agents. Examples of therapeutic agents are described in greater detail below under the heading "Therapeutic Agents." In some embodiments, the therapeutic member 102 is sufficiently flexible and/or elastic such that it may be compressed within a delivery catheter for intravascular delivery to the treatment site (with or without the anchoring member 100).

The film may include a therapeutic region 106 comprising a polymer film containing the one or more therapeutic agents (such as a chemotherapeutic agent), a control region 104 configured to regulate the release of the therapeutic agent(s) from the film, and a base region 108 configured to provide directional release capability to the film. If the anchoring member has a continuous impermeable membrane, the base region 108 may be eliminated or replaced by another control region 104. The control region 104 may include one or more bioresorbable polymers and one or more releasing agents. When the multilayer film is implanted within the esophageal lumen L, the control region 104 comes into contact with physiological fluids which dissolve one or more releasing agents within the control region 104 at a rate higher than that of the degradation rate of the bioresorbable polymer. Dissolution of the releasing agent causes channels or voids to form in the control region 104, thereby enabling the controlled release of the therapeutic agent (e.g., diffusion)

radially outwardly through the openings 101 in the mesh structure and towards the tumor T and/or esophageal wall EW, as indicated by the arrows in FIG. 3. Each of the therapeutic region 106, the control region 104, and the base region 108 is described in greater detail below.

As shown in FIG. 3, the control region 104 may comprise the outermost region of the film (e.g., radially farthest from the center of the esophageal lumen L) such that the control region 104 is adjacent the mesh structure of the anchoring member 100 and between (a) the therapeutic region 106 and (b) the anchoring member 100 and tumor T. This way, the control region 104 is well positioned to regulate the release of therapeutic agent from the therapeutic region 106.

In some embodiments, the control region 104 may comprise a single layer of biodegradable, bioresorbable polymer mixed with a releasing agent (see, for example, FIG. 39A). In some embodiments, the control region 104 may include multiple layers of biodegradable, bioresorbable polymer (see, for example, FIGS. 39B-39D). For example, the control region 104 may include as few as two layers of biodegradable, bioresorbable polymer or as many as 10 or 15 layers or more. The layers of the control region 104 may be micro-thin sheets or layers (i.e., microlayers), each having a thickness of from approximately 5 µm to 150 µm, 5 µm to 100 µm, 5 µm to 50 µm, 5 µm to 25 µm, 5 µm to 10 µm, 5 µm to 7 µm, or 7 µm to 9 µm. In some embodiments of the multi-layered control region 104, at least one layer may comprise a polymer mixed with a releasing agent, and at least one other layer may comprise a polymer having no releasing agent mixed therein (see, for example, FIG. 39B). In some embodiments, the multi-layer control region 104 may include multiple layers having a releasing agent mixed into each polymer layer. In such an embodiment, at least two of the releasing agent/polymer layers may have different concentrations of the releasing agent (see, for example, FIG. 39C). In some embodiments, each of the releasing agent/polymer layers may have different releasing agents in different concentrations (see, for example, FIG. 39D). One or more layers of the film may contain a hydrogel, such as PEG, to facilitate adherence of the tissue to the anchoring member.

The therapeutic region 106 may include a plurality of micro layers bonded together (e.g., 15 layers, 20 layers, 25 layers, etc.). In some embodiments, the therapeutic region 106 may comprise a layer comprised only of essentially pure therapeutic agent, or a pharmaceutically acceptable salt thereof (i.e., no polymer or other agents) (for example, see FIG. 40A). In some embodiments, the therapeutic region 106 may comprise a single layer of polymer loaded with a therapeutic agent (see, for example, FIG. 40B). In such embodiments, the therapeutic agent may be dissolved into the polymer which is then applied as a single layer to the film construct via any number of methods (e.g., dip coating, spray coating, solvent casting, etc.). In some embodiments, the therapeutic agent may be imbedded or impregnated in the polymer layer in a solid, fibrous or particulate form.

In several embodiments, the therapeutic region 106 may comprise multiple, micro-thin sheets of biodegradable, bioresorbable polymer, where each micro-thin sheet (or layer) is loaded with one or more therapeutic agents (see, for example, FIG. 40C). In such embodiments, the micro-thin sheets may have a substantially uniform construction and are stacked and bonded together. These micro-thin polymer sheets may each have a thickness from approximately 5 µm to 100 µm, 5 µm to 50 µm, 5 µm to 25 µm, 5 µm to 10 µm, 5 µm to 7 µm, or 7 to 9 µm thick, with the overall thickness of the therapeutic region 106 based on the total number of micro-thin sheets that are stacked. Due to heat compression bonding, the thickness of the total microlayer structure will be less than the sum of the thicknesses of each micro-thin sheet. The reduction in thickness of the microlayer structure from the sum of the thicknesses of each micro-thin sheet may be 50%, 40%, 30%, 25%, or 20%. As described in greater detail below, this multilayer structure of the therapeutic region 106 may provide increased control over therapeutic agent release kinetics.

In accordance with several embodiments of the present technology, the therapeutic region 106 may have a multilayer or microlayer structure where the individual sheets or layers of the therapeutic region 106 may not have uniform construction or properties (see, for example, FIG. 40D.) In such embodiments, each sheet may have differences in dimensions (e.g., thickness), polymer composition, relative proportion/concentration of polymer to therapeutic agent to releasing agent (optional), etc., in order to achieve the most clinically desirable release kinetics. In still some embodiments, the therapeutic region 106 may comprise electrospun nanofibers made of a biodegradable, bioresorbable polymer that is loaded with one or more therapeutic agents (see, for example, FIG. 40E.

In some embodiments in which the therapeutic region 106 comprises more than one therapeutic agent, the therapeutic region 106 may comprise a first therapeutic agent and a second therapeutic agent, wherein the multilayer film is configured to release from the therapeutic region 106 the first and second therapeutic agents at the same time. This configuration may be particularly useful in treatments where multi-modal pharmacological therapy is clinically indicated. In some embodiments, the multilayer film may be configured to release from the therapeutic region 106 the first and second therapeutic agents at different times (e.g., as part of a sequenced dosage regimen).

Referring still to FIG. 3, the base region 108 may comprise the innermost region of the film (i.e., radially closest to the center of the esophageal lumen) such that the base region 108 is positioned between the esophageal lumen L and the therapeutic region 106. In some embodiments, the base region 108 may be configured to provide structural support to the therapeutic region 106 and/or film. The base region 108 may comprise a low porosity, high density of bioresorbable polymer, which is substantially impermeable, that provides controlled directionality of released therapeutic agent by blocking or impeding passage of the therapeutic agent from the therapeutic region 106. Accordingly, the agents released from the therapeutic region 106 take a path of lesser resistance through the control region 104 opposite the base region 108, away from the lumen L and towards the targeted tumor T. The base region 108 and its position relative to the therapeutic region 106 may be particularly beneficial for concentrating the therapeutic agent towards the targeted tumor and reducing or altogether avoiding the unwanted release of the therapeutic agent into the esophageal lumen L. As depicted in FIG. 3, in some embodiments the base region 108 optionally extends radially outwardly beyond the therapeutic region 106 (and/or the control region 104 and anchoring member 100) at the longitudinal ends of the device 10 to prevent loss of released therapeutic agent up and down the lumen L. In other embodiments, the therapeutic region 106 is thin enough that the exposed edges of the therapeutic region do not release more therapeutic agent than is desired over any time period. In some embodiments, the film does not include a base region and is comprised solely of the control region 104 and the therapeutic region 104. In several embodiments, the film comprises a single region (e.g., one layer) that includes the therapeutic agent, the releasing agent, and a polymer.

In some embodiments of the present technology, the construction/composition of other layers of the multilayer film can be varied to facilitate the release of therapeutic agent. For example, the base region 108, the therapeutic region 106, and the control layer of the multilayer film depicted in FIG. 3 may have different porosities ranging from low porosity in the base region 108 to higher porosities in the therapeutic agent and control layers to facilitate the release of therapeutic agent from the multilayer film. In additional embodiments, the porosities of the edges of the multilayer film, or within portions of any of the individual layers, can be varied to properly regulate or manipulate the release of therapeutic agent. Additionally or alternatively, the diffusion release of therapeutic agent can be modulated by altering the relative concentration of releasing agent in each of the layers. To prevent undesirable release of therapeutic agent or further regulate the release of therapeutic agent the edges of the multilayer film may be sealed by adhesive, chemicals, solvents, or heat. Additionally, a bioresorbable polymer may be wrapped around the entire multilayer film and sealed on the top or bottom surface creating a control region structure similar to that depicted in FIG. 3. The control region may be incorporated as the final wrapped layer to seal the edges. Additionally, a control region solution may be prepared and the entire film sample dip- or spray-coated in the control region.

In some embodiments, all or a portion of the base region may be permeable. For example, such a configuration may be desirable in cases where the tumor grows in between struts or within openings at the surface of the anchoring member to direct the chemotherapeutic agent radially inward toward the esophageal lumen. In some embodiments, the base region may include an adjunctive agent (described in greater detail below), such as anti-inflammatory or functional coating such that food debris and other matter passing through the esophagus do not adhere to the stent.

Additional examples of therapeutic members, base regions, control regions, therapeutic regions, and therapeutic agents suitable for use with the treatment devices of the present technology are described in U.S. Provisional Application No. 62/569,349, filed Oct. 6, 2017, which is incorporated herein by reference in its entirety.

II. Therapeutic Agents

The therapeutic agent carried by the therapeutic member of the present technology may be any biologically active substance (or combination of substances) that provides a therapeutic effect in a patient in need thereof. The therapeutic agent may include one or more chemotherapeutic agents and/or photosensitizing agents (such as one or more porphyrin-based compounds, chlorins, and dyes) in combination with one or more chemoprotectants (e.g., leucovorin), one or more vasoconstrictors (e.g., epinephrine, clonidine, etc.), and one or more adjunctive agents (see discussion below). Unless otherwise specified, "chemotherapeutic agent" as used herein includes photosensitizing agents.

As mentioned above, the therapeutic agent may include one or more chemotherapeutic agents. In some embodiments, the therapeutic agent may include only a single chemotherapeutic agent, such as, for example, those listed in Table 1 below. In some embodiments, the therapeutic agent may include two or more chemotherapeutic agents for simultaneous or sequential release. Exemplary combinations of chemotherapeutic agents include, for example, any combination of the chemotherapeutic agents in the first column of Table 1, as well as those listed in column 2 of Table 1 below.

TABLE 1

| Examples of Single Chemotherapeutic Agents | Examples of Combinations of Chemotherapeutic Agents |
|---|---|
| Ramucirumab | 5-FU leucovorin calcium (together referred to as "5-FU-LIV") |
| docetaxel | 5-FU, leucovorin, and capecitabine |
| trastuzumab | capecitabine and irinotecan hydrochloride (together referred to as "XELIRI") |
| fluorouracil or 5-FU | carboplatin and paclitaxel (Taxol ®) |
| paclitaxel | cisplatin and 5-FU |
| Oxaliplatin | epirubicin, cisplatin, and 5-FU (together referred to as "ECF") |
| Epirubicin | epirubicin, oxaliplatin, and 5-FU |
| Capecitabine | epirubicin, cisplatin, and capecitabine |
| oxaliplatin | irinotecan and 5-FU |
| Irinotecan | irinotecan, 5-FU, and leucovorin |
| Floxuridine | docetaxel, cisplatin, and 5-FU (together referred to as "DCF") |
| Porfimer | docetaxel, oxaliplatin, cisplatin, and 5-FU |
| aminolevulinic acid ("ALA") | docetaxel, oxaliplatin, cisplatin, and 5-FU |
| methyl aminolevulinate ("MAL") | docetaxel, cisplatin, 5-FU, and leucovorin |
| carboplatin | docetaxel, oxaliplatin, and 5-FU |
| Cisplatin | docetaxel, carboplatin, and 5-FU |
| | cisplatin and capecitabine |
| | oxaliplatin and 5-FU |
| | oxaliplatin, 5-FU, and leucovorin |
| | oxaliplatin and capecitabine |
| | epirubicin, cisplatin, and capecitabine |
| | epirubicin (Ellence ®), oxaliplatin, and capecitabine |
| | platinum plus fluoropyrimidine doublet (e.g., FOLFOX, CAPOX, S-1 plus oxaliplatin, cisplatin/FU, or S-1 plus cisplatin) |
| | a fluoropyrimidine, oxaliplatin, docetaxel |
| | capecitabine and irinotecan HCL |
| | irinotecan and cisplatin |
| | paclitaxel and capecitabine |
| | cisplatin and capecitabine |
| | paclitaxel and cisplatin |
| | docetaxel and cisplatin |

TABLE 1-continued

| Examples of Single Chemotherapeutic Agents | Examples of Combinations of Chemotherapeutic Agents |
|---|---|
| | paclitaxel and 5-FU |
| | 5-FU and leucovorin |
| | 5-FU, cisplatin, and leucovorin |
| | docetaxel and irinotecan |
| | paclitaxel and docetaxel |
| | ramucirumab and paclitaxel |

A pharmaceutically acceptable salt refers to those salts that retain the biological effectiveness and properties of neutral therapeutic agents and that are not otherwise unacceptable for pharmaceutical use. Pharmaceutically acceptable salts include salts of acidic or basic groups, which groups may be present in the therapeutic agents. The therapeutic agents used in present technology that are basic in nature are capable of forming a wide variety of salts with various inorganic and organic acids. Pharmaceutically acceptable acid addition salts of basic therapeutic agents used in the present technology are those that form non-toxic acid addition salts, i.e., salts comprising pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The therapeutic agents of the present technology that include an amino moiety may form pharmaceutically acceptable salts with various amino acids, in addition to the acids mentioned above. Suitable base salts are formed from bases which form non-toxic salts and examples are the aluminum, calcium, lithium, magnesium, potassium, sodium, zinc and diethanolamine salts.

A pharmaceutically acceptable salt may involve the inclusion of another molecule such as water or another biologically compatible solvent (a solvate), an acetate ion, a succinate ion or other counterion. The counterion may be any organic or inorganic moiety that stabilizes the charge on the parent compound. Furthermore, a pharmaceutically acceptable salt may have more than one charged atom in its structure. Instances in which multiple charged atoms are part of the pharmaceutically acceptable salt can have multiple counter ions. Hence, a pharmaceutically acceptable salt can have one or more charged atoms and/or one or more counterion.

The therapeutic agent or pharmaceutically acceptable salt thereof may be an essentially pure compound or be formulated with a pharmaceutically acceptable carrier such as diluents, adjuvants, excipients, or vehicles known to one skilled in the art. The carrier(s) must be "acceptable" in the sense of being compatible with the other ingredients of the formulations and not deleterious to the recipient thereof. For example, diluents include lactose, dextrose, sucrose, mannitol, sorbitol, cellulose, glycine, and the like. For examples of other pharmaceutically acceptable carriers, see Remington: The Science and Practice of Pharmacy (21st Edition, University of the Sciences in Philadelphia, 2005).

The therapeutic agent or pharmaceutically acceptable salt form may be jet milled or otherwise passed through a sieve to form consistent particle sizes further enabling the regulated and controlled release of the therapeutic agent. This process may be particularly helpful for highly insoluble therapeutic agents.

The therapeutic member may also contain one or more adjunctive agents for use with any of the above chemotherapeutic agents/combinations of chemotherapeutic agents and/or photosensitizing agents. For example, the therapeutic member may include an adjunctive agent in the form of a local analgesic to limit any pain caused by the placement of the device or the action of the chemotherapeutic agents. A local analgesic may also reduce pain associated with swallowing, thereby enabling the patient to improve his/her diet. In some embodiments of the technology, the therapeutic agent includes an analgesic, including but not limited to, anesthetics, local anesthetics, narcotics, and anti-inflammatory agents. The analgesic may comprise the pharmacologically active drug or a pharmaceutically acceptable salt thereof. Suitable local anesthetics include, but are not limited to, bupivacaine, ropivacaine, mepivacaine, etidocaine, levobupivacaine, trimecaine, carticaine, articaine, lidocaine, prilocaine, benzocaine, procaine, tetracaine, chloroprocaine, and combinations thereof. Preferred local anesthetics include bupivacaine and ropivacaine. Typically, local anesthetics produce anesthesia by inhibiting excitation of nerve endings or by blocking conduction in peripheral nerves. Such inhibition is achieved by anesthetics reversibly binding to and inactivating sodium channels. Sodium influx through these channels is necessary for the depolarization of nerve cell membranes and subsequent propagation of impulses along the course of the nerve. When a nerve loses depolarization and capacity to propagate an impulse, the individual loses sensation in the area supplied by the nerve. Any chemical compound possessing such anesthetic properties is suitable for use in the present technology.

Other therapeutic agents suitable for use as analgesics include narcotics, for example, cocaine, and anti-inflammatory agents. Examples of appropriate anti-inflammatory agents include steroids, such as prednisone, betamethasone, cortisone, dexamethasone, hydrocortisone and methylprednisolone. Other appropriate anti-inflammatory agents include non-steroidal anti-inflammatory drugs (NSAIDs), such as aspirin, Ibuprofen, naproxen sodium, diclofenac, diclofenac-misoprostol, celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, mefenamic acid, and other COX-2 inhibitors, and combinations thereof.

In some embodiments, the therapeutic agent of the present technology may include an adjunctive agent in the form of an antibiotic, antimicrobial or antifungal agent or combinations thereof to limit any risk of infection as the chemotherapeutic agent causes necrosis of the tumor. For example, suitable antibiotics and antimicrobials include, but are not limited to, amoxicillin, amoxicillin/clavulanate, cephalexin, ciprofloxacin, clindamycin, metronidazole, azithromycin, levofloxacin, sulfamethoxazole/trimethoprim, tetracycline(s), minocycline, tigecycline, doxycycline, rifampin, triclosan, chlorhexidine, penicillin(s), aminoglycides, quinolones, fluoroquinolones, vancomycin, gentamycin, cephalosporin(s), carbapenems, imipenem, ertapenem, antimicrobial peptides, cecropin-mellitin, magainin, dermaseptin, cathelicidin, α-defensins, and α-protegrins. Antifungal agents include, but are not limited to, ketoconazole, clortrimazole, miconazole, econazole, intraconazole, fluconazole, bifoconazole, terconazole, butaconazole, tioconazole, oxiconazole, sulconazole, saperconazole, voriconazole, terbinafine, amorolfine, naftifine, griseofulvin, haloprogin, butenafine, tolnaftate, nystatin, cyclohexamide, ciclopirox, flucytosine, terbinafine, and amphotericin B.

III. Polymers

As detailed above, the control region 104, the therapeutic region 106, and the base region 108 include one or more bioresorbable polymers, which preferably have a predetermined degradation rate. The terms "bioresorbable," or "bioabsorbable," mean that a polymer will be absorbed within the patient's body, for example, by a cell or tissue. These polymers are "biodegradable" in that all or parts the polymeric film will degrade over time by the action of enzymes, by hydrolytic action and/or by other similar mechanisms in the patient's body. In various embodiments, the biodegradable, bioresorbable polymer film can break down or degrade within the body to non-toxic components while a therapeutic agent is being released. Polymers used as base components of the multilayer films of the technology may break down or degrade after the therapeutic agent is fully released. The bioresorbable polymers are also "bioerodible," in that they will erode or degrade over time due, at least in part, to contact with substances found in the surrounding tissue, fluids, or by cellular action.

One or more of the polymers utilized within one or more of the control region 104, the therapeutic region 106, and the base region 108 may be selected based on their corresponding degradation profiles. For example, it may be beneficial to select one or more polymers that produce a degradation rate that allows for increased exposure of the mesh structure of the anchoring member (to improve fixation/prevent migration), yet accounts for the discontinued drug release (thus making the stent more susceptible to tumor ingrowth). For implantation within the esophagus for sustained drug release over weeks or months, a polymer, copolymer, or terpolymer may be selected based on the specific therapeutic agent and desired release profile. For example, poly(lactide-co-caprolactone) (PLCL)—may be particularly beneficial, as it is flexible, elastic, and degrades over 12-18 months, which may allow for longer release of therapeutic agents, such as chemotherapeutic agents.

The treatment portions of the present technology may be comprised of bioresorbable polymers. In some embodiments, both the therapeutic region and the control region comprise a polymer (or mix of polymers), which can be the same or different polymer (or mix of polymers) in the same or different amount, concentration, and/or weight percentage. In some embodiments, the control region comprises a polymer and the therapeutic region does not include a polymer. In some embodiments, the therapeutic region comprises a polymer and the control region 300 does not include a polymer.

The bioresorbable polymers used in the present technology preferably have a predetermined degradation rate. The terms "bioresorbable," or "bioabsorbable," mean that a polymer will be absorbed within the patient's body, for example, by a cell or tissue. These polymers are "biodegradable" in that all or parts the polymeric film will degrade over time by the action of enzymes, by hydrolytic action and/or by other similar mechanisms in the patient's body. In various embodiments, the biodegradable, bioresorbable polymer film can break down or degrade within the body to non-toxic components while a therapeutic agent is being released. Polymers used as base components of the depots of the present technology may break down or degrade after the therapeutic agent is fully released. The bioresorbable polymers are also "bioerodible," in that they will erode or degrade over time due, at least in part, to contact with substances found in the surrounding tissue, fluids or by cellular action.

Criteria for the selection of the bioresorbable polymer suitable for use in the present technology include: 1) in vivo safety and biocompatibility; 2) therapeutic agent loading capacity; 3) therapeutic agent releasing capability; 4) degradation profile; 5) potential for inflammatory response; and 6) mechanical properties, which may relate to form factor and manufacturability. As such, selection of the bioresorbable polymer may depend on the clinical objectives of a particular therapy and may involve trading off between competing objectives. For example, PGA (polyglycolide) is known to have a relatively fast degradation rate, but it is also fairly brittle. Conversely, polycaprolactone (PCL) has a relatively slow degradation rate and is quite elastic. Copolymerization provides some versatility if it is clinically desirable to have a mix of properties from multiple polymers. For biomedical applications, particularly as a biodegradable depot for drug release, a polymer or copolymer using at least one of poly(L-lactic acid) (PLA), PCL, and PGA are generally preferred. The physical properties for some of these polymers are provided in Table 2 below.

TABLE 2

| Materials | Tg (° C.) [1] | Tm (° C.) [1] | Elastic Modulus (GPa) [1] | Tensile Strength (MPa) [1] | Tensile Elongation (%) [1] | Degradation Time (months) [2] |
|---|---|---|---|---|---|---|
| PLA | 45-60 | 150-162 | 0.35-3.5 | 21-60 | 2.5-6 | 12-16 |
| PLLA | 55-65 | 170-200 | 2.7-4.14 | 15.5-150 | 3-10 | >24 |
| PDLA | 50-60 | — | 1.0-3.45 | 27.6-50 | 2-10 | 6-12 |
| PLA/PGA (50:50) | 40-50 | — | 1.0-4.34 | 41.4-55.2 | 2-10 | 3 |
| PGA | 35-45 | 220-233 | 6.0-7.0 | 60-99.7 | 1.5-20 | 6-12 |
| PCL | -60-65 | 58-65 | 0.21-0.44 | 20.7-42 | 300-1000 | >24 |

In many embodiments, the polymer may include polyglycolide (PGA). PGA is one of the simplest linear aliphatic polyesters. It is prepared by ring opening polymerization of a cyclic lactone, glycolide. It is highly crystalline, with a crystallinity of 45-55%, and thus is not soluble in most organic solvents. It has a high melting point (220-225° C.), and a glass transition temperature of 35-40° C. (Vroman, L., et al., Materials, 2009, 2:307-44). Rapid in vivo degradation of PGA leads to loss of mechanical strength and a substantial local production of glycolic acid, which in substantial amounts may provoke an inflammatory response.

In many embodiments, the polymer may include polylactide (PLA). PLA is a hydrophobic polymer because of the presence of methyl (—CH3) side groups off the polymer backbone. It is more resistant to hydrolysis than PGA because of the steric shielding effect of the methyl side groups. The typical glass transition temperature for representative commercial PLA is 63.8° C., the elongation at break is 30.7%, and the tensile strength is 32.22 MPa (Vroman, 2009). Regulation of the physical properties and biodegradability of PLA can be achieved by employing a hydroxy acids co-monomer component or by racemization of D- and L-isomers (Vroman, 2009). PLA exists in four forms: poly(L-lactic acid) (PLLA), poly(D-lactic acid) (PDLA), meso-poly(lactic acid) and poly(D,L-lactic acid) (PDLLA), which is a racemic mixture of PLLA and PDLA. PLLA and PDLLA have been the most studied for biomedical applications.

Copolymerization of PLA (both L- and D,L-lactide forms) and PGA yields poly(lactide-co-glycolide) (PLGA), which is one of the most commonly used degradable polymers for biomedical applications. In many embodiments, the polymer may include PLGA. In many embodiments, the polymer may include PLGA. Since PLA and PGA have significantly different properties, careful choice of PLGA composition can enable optimization of performance in intended clinical applications. Physical property modulation is even more significant for PLGA copolymers. When a composition is comprised of 25-75% lactide, PLGA forms amorphous polymers which are very hydrolytically unstable compared to the more stable homopolymers. This is demonstrated in the degradation times of 50:50 PLGA, 75:25 PLGA, and 85:15 PLGA, which are 1-2 months, 4-5 months and 5-6 months, respectively. In some embodiments, the polymer may be an ester-terminated poly (DL-lactide-co-glycolide) ("PLGA") in a molar ratio of 50:50 (DURECT Corporation).

In some embodiments, the polymer may include polycaprolactone (PCL). PCL is a semi-crystalline polyester with high organic solvent solubility, a melting temperature of 55-60° C., and glass transition temperature of −54° C. (Vroman, 2009). PCL has a low in vivo degradation rate and high drug permeability, thereby making it more suitable as a depot for longer term drug delivery. For example, Capronor® is a commercial contraceptive PCL product that is able to deliver levonorgestrel in vivo for over a year. PCL is often blended or copolymerized with other polymers like PLLA, PDLLA, or PLGA. Blending or copolymerization with polyethers expedites overall polymer erosion. Additionally, PCL has a relatively low tensile strength (~23 MPa), but very high elongation at breakage (4700%), making it a very good elastic biomaterial. PCL also is highly processable, which enables many potential form factors and production efficiencies.

Suitable bioresorbable polymers and copolymers for use in the present technology include, but are not limited to, poly(alpha-hydroxy acids), poly(lactide-co-glycolide) (PLGA or DLG), poly(DL-lactide-co-caprolactone) (DL-PLCL), polycaprolactone (PCL), poly(L-lactic acid) (PLA), poly(trimethylene carbonate) (PTMC), polydioxanone (PDO), poly(4-hydroxy butyrate) (PHB), polyhydroxyalkanoates (PHA), poly(phosphazene), polyphosphate ester), poly(amino acid), polydepsipeptides, poly(butylene succinate) (PBS), polyethylene oxide, polypropylene fumarate, polyiminocarbonates, poly(lactide-co-caprolactone) (PLCL), poly(glycolide-co-caprolactone) (PGCL) copolymer, poly(D,L-lactic acid), polyglycolic acid, poly(L-lactide-co-D,L-lactide), poly(L-lactide-co-glycolide), poly(D,L-lactide-co-glycolide), poly(gycolide-trimethylene carbonate), poly(glycolide-co-carolactone) (PGCL), poly (ethyl glutamate-co-glutamic acid), poly(tert-butyloxy-carbonylmethyl glutamate), poly(glycerol sebacate), tyrosine-derived polycarbonate, poly 1,3-bis-(p-carboxyphenoxy) hexane-co-sebacic acid, polyphosphazene, ethyl glycinate polyphosphazene, polycaprolactone co-butylacrylate, a copolymer of polyhydroxybutyrate, a copolymer of maleic anhydride, a copolymer of poly(trimethylene carbonate), polyethylene glycol (PEG), hydroxypropylmethylcellulose and cellulose derivatives, polysaccharides (such as hyaluronic acid, chitosan and starch), proteins (such as gelatin and collagen) or PEG derivatives and copolymers thereof. Other suitable polymers or copolymers include polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D-lactide, D,L-lactide, L-lactide, D,L-lactide-caprolactone (DL-CL), D,L-lactide-glycolide-caprolactone (DL-G-CL), dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate)hydroxypropyl cellulose, hydroxypropyl methylcellulose, hydroxyethyl methylcellulose, carboxymethylcellulose or salts thereof, Carbopol®, poly(hydroxyethylmethacrylate), poly(methoxyethylmethacrylate), poly(methoxyethoxy-ethylmethacrylate), polymethylmethacrylate (PMMA), methylmethacrylate (MMA), gelatin, polyvinyl alcohols, propylene glycol, or combinations thereof.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

As described above, it may be desirable in certain clinical applications using depots for controlled delivery of therapeutic agents to use copolymers comprising at least two of PGA, PLA, PCL, PDO, and PVA. These include, for example, poly(lactide-co-caprolactone) (PLCL) (e.g. having a PLA to PCL ratio of from 90:10 to 60:40, or 95:5 to 10:90) or its derivatives and copolymers thereof, poly(DL-lactide-co-caprolactone) (DL-PLCL) (e.g. having a DL-PLA to PCL ratio of from 90:10 to 50:50) or its derivatives and copolymers thereof, poly(glycolide-co-caprolactone) (PGCL) (e.g. having a PGA to PCL ratio of from 90:10 to 10:90, or 95:5 to 10:90) or its derivatives and copolymers thereof, or a blend of PCL and PLA (e.g. a ratio blend of PCL and PLA having a wt:wt ratio of 1:9 to 9:1). In one preferred embodiment, the bioresorbable polymer comprises a copolymer of polycaprolactone (PCL), poly(L-lactic acid) (PLA) and polyglycolide (PGA). In such a preferred embodiment, the ratio of PGA to PLA to PCL of the copolymer may be 5-60% PGA, 5-40% PLA and 10-90% PCL. In additional embodiments, the PGA:PLA:PCL ratio may be 40:40:20, 30:30:50, 20:20:60, 15:15:70, 10:10:80, 50:20:30, 50:25:25, 60:20:20, or 60:10:30. In some embodiments, the polymer is an ester-terminated poly (DL-lactide-co-glycolide-co-caprolactone) in a molar ratio of 60:30:10 (DURECT Corporation).

In some embodiments, a terpolymer may be beneficial for increasing the degradation rate and ease of manufacturing, etc.

Biocompatible non-degradable polymers included within the therapeutic region, control region, and/or base region disclosed herein may be selected from the group consisting of poly(ethylene-co-vinyl acetate), polyethylene, polypropylene, poly(vinyl acetate), poly(ethylene terephthalate), poly (ethylene glycol), poly(ethylene oxide), polyacrylic acid, poly(methylmethacrylate), polyhyaluronic acids, alginate, chitosan and mixtures thereof.

In some embodiments, the polymers within any region may be formed by heat compression. The polymer may also be formed into a thin film using a casting method.

In some embodiments, to attach the therapeutic member to the anchoring member, the therapeutic member formulation could be spray coated directly onto anchoring member, which is a common method but this method could not carry high amount of drug and the coating uniformity and adhesion to anchoring member is usually not good. Our film and layered based configuration of therapeutic member could be attached to anchoring member or delivered separately from anchoring member. For attaching to anchoring member, therapeutic member could be sutured, wrapped around, attached by chemical adhesion or heat bonding. The therapeutic member may be made of polymers of different properties such as elasticity, stretchability, or rigidity. If the therapeutic member includes a polymer with elastic properties, it may be attached to the anchoring member by leveraging such elastic properties. For example, the therapeutic member may comprise an elastic tube that covers individual stent struts or segments. If the therapeutic member includes a more elastic polymer, the therapeutic member may be attached such that the therapeutic member layer stretches with the final deployed anchoring member dimension. For example, the therapeutic member may be a cylindrical tube that covers the anchoring member in a collapsed state but expands with the anchoring member upon release of the anchoring member from a delivery sheath. If the therapeutic member includes a more rigid polymer, the therapeutic member may be attached in a configuration such that the length and width of the therapeutic member remains unchanged pre- and post-deployment (for example, see FIG. 21).

IV. Selected Dosing and Release Profiles for the Therapeutic Members of the Present Technology The therapeutic region 106 may contain a therapeutically effective dose of chemotherapeutic agent to be administered periodically or continuously over the course of at least six weeks. As used herein, "therapeutically effective dose" refers to an amount of chemotherapeutic agent required to resist tumor ingrowth and maintain luminal patency. In some embodiments, the chemotherapeutic agent may contain at least 40 mg, at least 50 mg, at least 60 mg, at least 70 mg, at least 80 mg, at least 90 mg, at least 100 mg, at least 200 mg, at least 300 mg, at least 400 mg, at least 500 mg, at least 600 mg, at least 700 mg, at least 800 mg, at least 900 mg, and at least 1000 mg of chemotherapeutic agent.

In various embodiments, the therapeutic member may release 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 12 mg, 14 mg, 15 mg, 17 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 280 mg, 300 mg, 320 mg, 340 mg, 360 mg, 380 mg, 400 mg, 420 mg, 440 mg, 460 mg, 480 mg, 500 mg, 540 mg, 580 mg, 620 mg, 660 mg, 700 mg, 740 mg, 780 mg, 820 mg, 860 mg, 900 mg, 940 mg, 980 mg, 1000 mg, 1020 mg, 2 mg to 1020 mg, 4 mg to 900 mg, 6 mg to 800 mg, 8 mg to 750 mg, 10 mg to 600 mg, 12 mg to 500 mg, 14 mg to 400 mg, 16 mg to 325 mg, 18 mg to 275 mg, 24 mg to 200 mg, 30 mg to 150 mg, 40 mg to 120 mg, 50 mg to 100 mg, 60 mg to 80 mg, 80 mg to 100 mg, 100 mg to 200 mg, 200 mg to 300 mg, 300 mg to 400 mg, 400 mg to 500 mg, 500 mg to 600 mg, 600 mg to 700 mg, 700 mg to 800 mg, 800 mg to 900 mg, or 900 mg to 1000 mg of chemotherapeutic agent per day, every other day, every three days, every four days, every five days, every six days, every week, every two weeks, every three weeks, monthly, and all subranges therebetween for a total of at least 3 days, at least 4 days, at least 5 days, at least 6 days, at least 7 days, at least 8 days, at least 10 days, at least 12 days, at least 15 days, at least 20 days, at least 25 days, at least 30 days, at least 6 weeks, at least 8 weeks, at least 10 weeks, at least 12 weeks, at least 14 weeks, at least 16 weeks, at least 18 weeks, at least 20 weeks, at least 22 weeks, at least 24 weeks, 2 to 10 days, 2 to 5 days, 5 to 10 days, 5 to 20 days, 10 to 20 days, 20 to 30 days, 20 to 40 days, 25 to 40 days, 30 to 60 days, 40 to 70 days, 50 to 80 days, 90 to 120 days, 30 days to 6 months, 60 days to 6 months, and 90 days to 6 months, 2 months to 8 months, 3 months to 9 months, 4 months to 10 months, 5 months to 11 months, 3 months to 12 months, 3 months to 13 months, 2 months to 14 months, 2 months to 15 months, or 3 months to 16 months.

The chemotherapeutic agent may be released continuously or in discrete dosages (any of the above dosages) at scheduled intervals (including any of the above intervals) during the foregoing time ranges.

In some embodiments, the therapeutic member and/or therapeutic region may include a first chemotherapeutic agent and a second chemotherapeutic agent different than the first chemotherapeutic agent. The first chemotherapeutic agent may be released continuously over any of the foregoing time ranges, while the second chemotherapeutic agent may be released in discrete dosages (any of the above dosages) at scheduled intervals (including any of the above intervals) over any of the foregoing time ranges. In this embodiment, the total number of days of release and the amount of chemotherapeutic agent released may be the same or different for the first and second chemotherapeutic agents. In some embodiments, the first and second chemotherapeutic agents may be released continuously over any of the foregoing time ranges. In this embodiment, the total number of days of release and the amount of chemotherapeutic agent released may be the same or different for the first and second chemotherapeutic agents. In various embodiments, both the first and second chemotherapeutic agents may be released in discrete dosages (any of the above dosages) at scheduled intervals (including any of the above intervals) over any of the foregoing time ranges. In this embodiment, the total number of days of release, the scheduled intervals, and the amount of chemotherapeutic agent released may be the same or different for the first and second chemotherapeutic agents. In any of the foregoing embodiments, the first and second chemotherapeutic agents may be contained in the same therapeutic region or different therapeutic region, the same layer within the therapeutic region or different layers, and/or the same therapeutic member or different therapeutic members. For those embodiments where the chemotherapeutic agent is delivered continuously, the release rate profile may be linear or non-linear.

In various embodiments, the therapeutic member releases 5%, 10%, 15%, 20%, 25%, 30%, 35%, 40%, 50% 55%, 60%, 65%, 70%, 75%, 80%, 85%, 90%, 95%, 99%, 100% of the chemotherapeutic agent over a period of 1 day to 6 months, 5 days to 5 months, 10 days to 4 months, 20 days to 3 months, or 1 month to 2 months 2 months to 8 months, 3 months to 9 months, 4 months to 10 months, 5 months to 11 months, 3 months to 12 months, 3 months to 13 months, 2 months to 14 months, 2 months to 15 months, or 3 months to 16 months after the therapeutic member is implanted in the esophageal lumen. In some embodiments, the therapeutic member releases no more than 50% of the chemotherapeutic agent therein over the first 2 week, 3 weeks, 4 weeks, 5 weeks, 6 weeks, 8 weeks, 10 weeks or 12 weeks.

V. Additional Embodiments

Figure 11A:
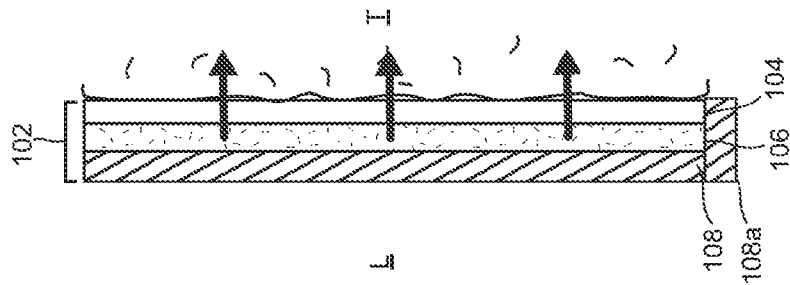
FIG. 11A is a cross-sectional view of a treatment device in accordance with the present technology, shown positioned adjacent a tumor within the esophagus of a patient.
Figure 11B:
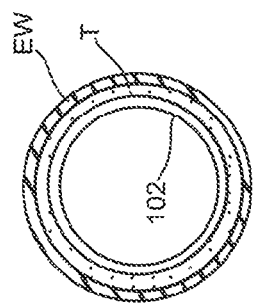
FIGS. 11B and 11C are cross-sectional end views of different configurations of the treatment device shown in FIG. 11A.

In some embodiments, the treatment device 10 comprises the therapeutic member 102 and does not include an anchoring member, integrated or otherwise. For example, as depicted in FIGS. 11A and 11B, the therapeutic member 102 may comprise a sleeve (e.g., an elongated tube) that includes any of the films detailed above. For example, the therapeutic member 102 may include a therapeutic region 106 having one or more therapeutic agents, a control region 104, and/or a base region 108 as described above. The portion of the therapeutic member 102 comprising the film (i.e., the portion administering the treatment) may be referred to as a treatment portion of the therapeutic member and/or sleeve. In some embodiments, the film comprises the entirety of the therapeutic member 102 and/or sleeve. In some embodiments, the film comprises only a portion of the therapeutic member 102 and/or sleeve.

Figure 11C:
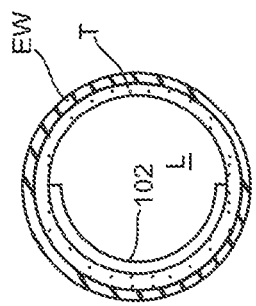
Figure 11D:
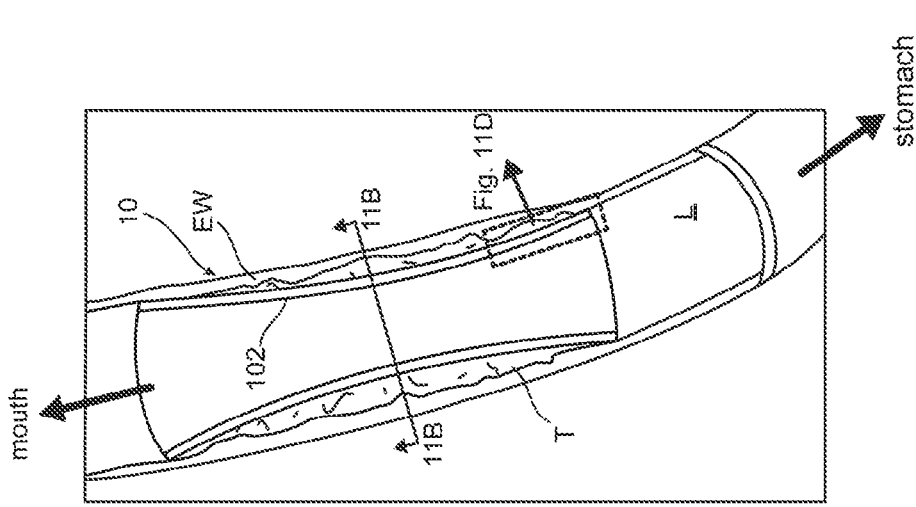
FIG. 11D is an enlarged cross-sectional view of a portion of the treatment device shown in FIG. 11A.

The sleeve may be delivered endoluminally by the clinician to the vicinity of the tumor and then positioned such that the treatment portion is positioned proximate to the tumor to ensure the tumor is getting a full dosage of the therapeutic agent. In some embodiments, all or one or more portions of the sleeve, film, and/or treatment portion may extend around less than the full circumference of the tumor and/or esophageal wall, as shown in FIG. 11C. The therapeutic region 106 and/or treatment portion may extend the entire length circumference of the sleeve, or the therapeutic region 106 and/or treatment portion may extend along only a portion of the length of the sleeve such that the sleeve comprises a single, discrete therapeutic region 106 and/or a single, discrete treatment portion. The therapeutic region 106 and/or treatment portion may extend the entire circumference of the sleeve, or the therapeutic region 106 and/or treatment portion may extend along only a portion of the circumference of the sleeve such that the sleeve comprises a single, discrete therapeutic region 106 and/or a single, discrete treatment portion. For example, the therapeutic region and/or treatment portion of the cuff may encompass a 30-degree arc of the cuff's circumference, and the clinician may position the therapeutic region and/or treatment portion proximate to the tumor. In some embodiments, the therapeutic region and/or treatment portion can encompass a 45-, 60-, 75-, 90-, 120-, 150-, or 180-degree portion of the cuffs circumference.

Figure 12A:
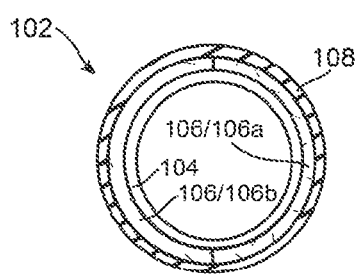
FIG. 12A is an enlarged cross-sectional end view of a therapeutic member in accordance with the present technology.
Figure 12B:
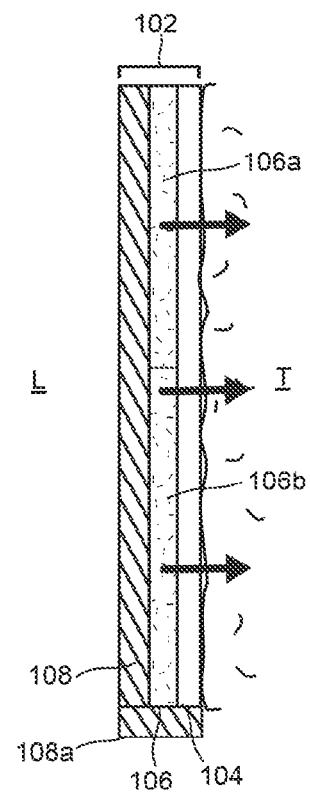
FIG. 12B is an enlarged cross-sectional view of a portion of a therapeutic member in accordance with the present technology.

In some embodiments, the sleeve may comprise multiple distinct therapeutic regions 106 and/or treatment portions (having the same or different therapeutic agents) that are adjacent or spaced apart circumferentially and/or longitudinally. For example, FIG. 12A is an example of several embodiments in which the sleeve and/or therapeutic member includes a first therapeutic region 106a extending around a first circumference of the sleeve, and a second therapeutic region 106b extending around a second circumference of the sleeve. In some embodiments, the sleeve and/or therapeutic member includes a first treatment portion extending around a first circumference of the sleeve, and a second treatment portion extending around a second circumference of the sleeve. FIG. 12B is an example of several embodiments in which the sleeve and/or therapeutic member includes a first therapeutic region 106a extending a first length of the sleeve, and a second therapeutic region 106b extending a second length of the sleeve. In some embodiments, the sleeve and/or therapeutic member includes a first treatment portion extending a first length of the sleeve, and a second treatment portion extending a second length of the sleeve.

Figure 13:
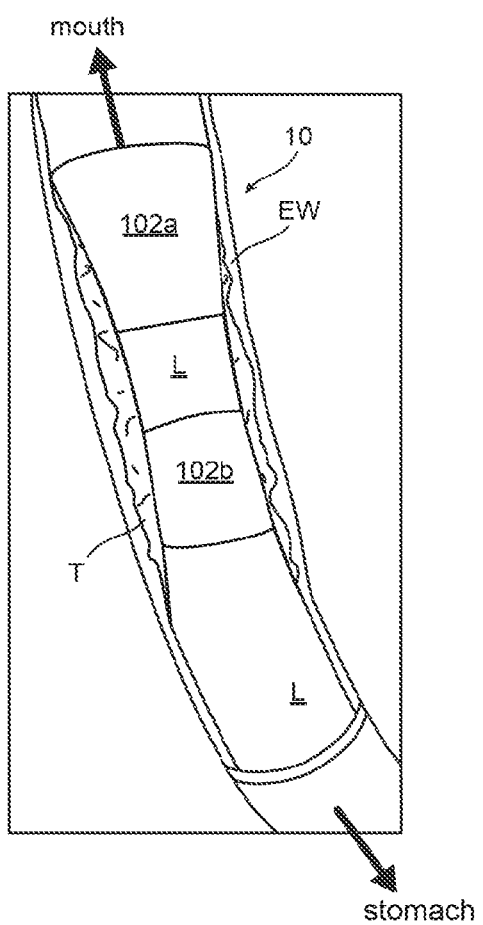
FIG. 13 shows a treatment device in accordance with the present technology positioned adjacent a tumor within the esophagus of a patient.

In some embodiments, for example as shown in FIG. 13, the therapeutic member 102 may be one or more cuffs (e.g., a short tube) comprised of any of the films detailed above. For example, the therapeutic member 102 may include a therapeutic region 106 having one or more therapeutic agents, a control region 104, and/or a base region 108 as described above. The portion of the therapeutic member 102 comprising the film (i.e., the portion administering the treatment) may be referred to as a treatment portion of the therapeutic member and/or cuff. In some embodiments, the film comprises the entirety of the therapeutic member 102 and/or cuff. In some embodiments, the film comprises only a portion of the therapeutic member 102 and/or cuff.

The cuff(s) may be delivered endoluminally by the clinician to the vicinity of the tumor and then positioned such that the therapeutic region 106 and/or the treatment portion of the cuff is positioned proximate to the tumor to ensure the tumor is getting a substantial dose of the therapeutic agent. In some embodiments, the entire cuff comprises the therapeutic region and/or treatment portion, or the therapeutic region and/or treatment portion may comprise a distinct band along the cuff's longitudinal axis. Given the longitudinal and rotational accuracy of the clinician's delivery technique, the cuff, in some embodiments, may be configured with a therapeutic region and/or treatment portion having a high density of therapeutic agent concentrated in a particular circumferential region of the cuff. For example, the therapeutic region and/or treatment portion of the cuff may encompass a 30-degree arc of the cuff's circumference, and the clinician may position the therapeutic region and/or treatment portion proximate to the tumor. In some embodiments, the therapeutic region and/or treatment portion can encompass a 45, 60, 75, 90, 120, 150, or 180-degree portion of the cuff's circumference.

In some of the cuff or sleeve embodiments described above, the therapeutic member may be configured for endoluminal placement with or without an integrated anchoring member. In cases without an integrated anchoring member, the therapeutic member may be fastened to the esophagus using any means for mechanical fixation (e.g., suture, staple, etc.). In several embodiments, a conventional, commercially-available esophageal stent can be used to secure the cuff or sleeve in place adjacent the tumor within the esophageal lumen. In such embodiments, the treatment provider may first deliver and position the endoluminal cuff or sleeve proximate to a vicinity of the esophagus requiring treatment (e.g., tumor) and then use a balloon to expand the cuff or sleeve to a deployed configuration such that the cuff or sleeve is proximate the tumor. Once the cuff or sleeve is positioned proximate to the tumor, the treatment provider may then select a commercially available esophageal stent for secure placement of the cuff or sleeve proximate to the esophageal wall.

Figure 14:
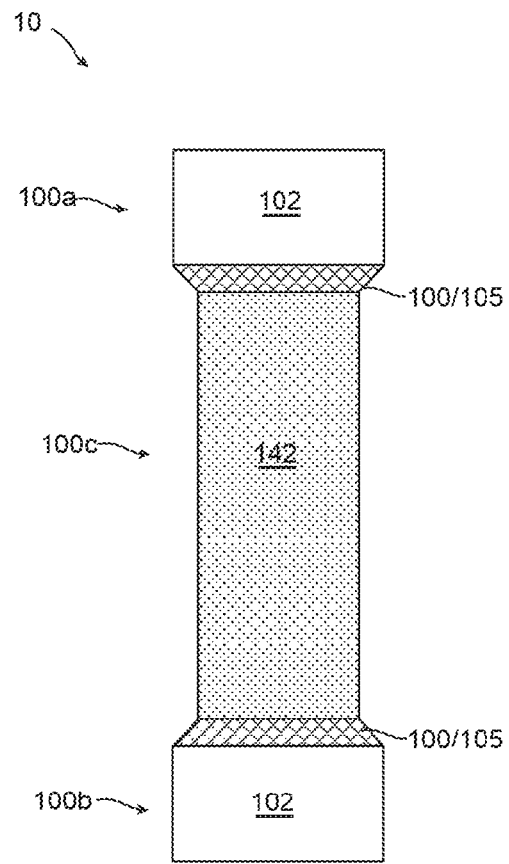
FIG. 14 is a front view of a treatment device including a cover in accordance with the present technology.

In some embodiments, the treatment device 10 may include a polymer cover along all or a portion of its length. The cover helps resist and/or prevent ingrowth of the tumor along the stent walls. In FIG. 14, the cover 142 is shown positioned around the body portion 100c of the anchoring member 100. In some embodiments, the cover 142 may be positioned at the interior and/or exterior surface of the body portion 100c (with or without the therapeutic member 102). The cover 142 may extend along all or a portion of the length of the body portion 100c, and/or about all or a portion of the circumference of the body portion 100c.

As shown in FIG. 14, the treatment device 10 may have two therapeutic members 102, each disposed at one of the first and second end portions 100a, 100b of the anchoring member 100. A first region 105 of the mesh structure of the anchoring member 100 may be exposed between the cover 142 and the therapeutic member 102 adjacent the first end portion 100a, and a second region 107 of the mesh structure of the anchoring member 100 may be exposed between the cover 142 and the therapeutic member 102 adjacent the second end portion 100b. The main cause of failure of conventional SEMS is tumor overgrowth at the ends of the stent that begins to occlude the esophageal lumen. Releasing and/or delivering the therapeutic agent at the ends of the anchoring member 100 may reduce or prevent such tumor overgrowth. The treatment device 10 may include any combination or configuration of exposed, covered, and/or film-adhered portions to improve fixation, prevent or reduce tumor ingrowth, and provide targeted delivery of therapeutic agent.

The cover 142 can be made from high density polyethylene (HDPE), low density polyethylene (LDPE), fluorinated ethylene propylene (FEP), polytetrafluoroethylene (PTFE), ethylene tetrafluoroethylene (ETFE), combinations thereof, and/or other suitable materials.

Figure 15:
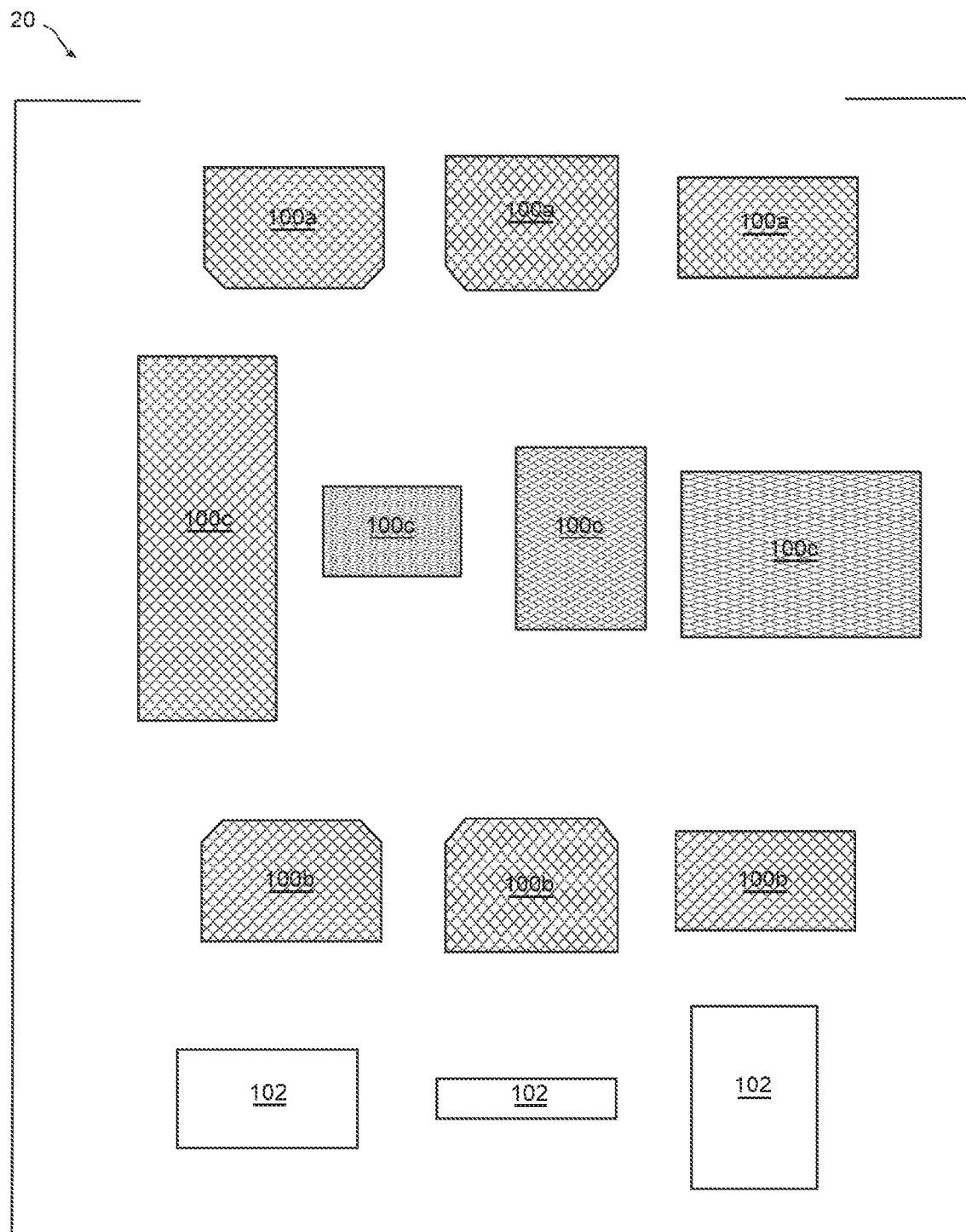
FIG. 15 shows a treatment system in accordance with the present technology.

FIG. 15 shows a treatment system 20 in accordance with the present technology that includes a plurality of independent anchoring member components and/or subcomponents and therapeutic members (or portions thereof) having a variety of shapes and sizes to account for the variability in presentation of esophageal tumors. The subcomponents of the system 20 are configured to be mixed-and-matched based on need. As shown in FIG. 15, the system 20 may include, for example: (a) several anchoring member options for the first end portion 100a having different shapes and sizes (e.g., flared end, no flared end, etc.), and different treatment portions based on differences in film coverage and/or composition, (b) several anchoring member options for body portion 100c having different shapes and sizes (i.e., wider diameter, narrower diameter, longer, shorter, etc.), and different treatment portions based on differences in film coverage and/or composition, and c) several anchoring member options for the second end portion 100b having different shapes and sizes (i.e., flared end, no flared end, etc.), and different treatment portions based on differences in film coverage and/or composition. In some embodiments, the system may include a plurality of treatment portions separate from the anchoring member subcomponents that have different shapes and sizes. The modularity provided by the treatment system 20 allows the clinician to determine which portions of the resulting modular treatment device should include the therapeutic member based upon the location of the tumor and its shape and volume. For example, in instances where an exceptionally large tumor is present in a distinct portion of the patient's esophagus, the treatment provide may use the modularity of the system to place multiple components, each having a treatment portion possessing a high concentration of chemotherapeutic agent, in close proximity to the tumor. The modularity of this system also enables subsequent interventions to place additional components based on newly developed circumstances. For example, a treatment system that is weakened due to tissue overgrowth at the proximal and/or distal regions of the implanted system can be bolstered by subsequently added components at the proximal and/or distal regions.

FIG. 16A is a front view of a treatment device 30 in accordance with the present technology. The treatment device 30 may include an expandable member 130 having a pre-set (e.g., heat set) helical and/or spiral configuration such that, in a deployed state, the member 130 self-expands to form a generally tubular structure defining a lumen extending therethrough. In FIG. 16A, adjacent turns of the expandable member 130 are spaced apart from one another by a gap. In other embodiments, however, adjacent turns of the expandable member 130 may touch or overlap one another such that the expandable member 130 forms a continuous tubular sidewall. A controllable delivery system for helical configurations may be provided so that the helical device may be gradually unwound, rewound, repositioned or replaced in its entirety. Such controlled delivery systems may be configured to begin to deploy the unwound portion of the treatment device 30 from either the proximal or distal end, in order to best target the tumor to be treated.

FIGS. 16B-16E are cross-sectional end views of different expandable member configurations in accordance with the present technology. The expandable member 130 may comprise a self-expanding support member 132 surrounded by a therapeutic member 102 (such as any of the therapeutic members detailed above). The support member 132 may be a superelastic wire (FIGS. 16B-16D) or ribbon (FIG. 16E). The therapeutic member 102 can be applied to the support member 132 by placing a film on either side of the support member 132 and bonding those layers together with the support member 132 sandwiched in between. Other suitable methods include via bonding, spray coat, dip coat, etc. The therapeutic member 102 can have any suitable cross-sectional shape, such as rectangular (FIGS. 16B and 16D), circular (FIG. 16C), spaceship-shaped (FIG. 16D), etc. In some embodiments, a plurality of any of the foregoing expandable members 130 may be braided together to form an integrated anchoring member and therapeutic member.

In some embodiments, the expandable member 130 may be formed entirely of a therapeutic member that is heat set to the desired spiral or helical shape. In such embodiments, the expandable member 130 may be implanted without a support member or other anchoring member.

In several embodiments, the helical or spiral expandable member 130 may be formed entirely of the therapeutic member and may be used with a separate, tubular anchoring member. In such embodiments, for example, the expandable member may be adhered to one end of the anchoring member via any of the fixation methods disclosed above with reference to FIGS. 2A-2D.

In some embodiments (not shown), the therapeutic member may be shape set into pleats and attached at one or more locations to the anchoring member. As the assembly expands (via self-expansion or other manual expansion methods described above), the pleats unfold and conform to the tubular shape of the anchoring member.

In some embodiments, the anchoring member may be a plurality of braided filaments or a laser-cut stent. The filaments of the braid or the stent wall may have recesses extending at least partially therethrough. The openings may include one or more therapeutic members disposed therein. For example, the anchoring member could be rolled and/or pressed along the therapeutic member in the form of a sheet (such as any of the films disclosed above), thereby forcing the therapeutic member into the openings.

In some embodiments, the treatment device may comprise a fully biodegradable/bioresorbable anchoring member comprising a polymer configured to bulk erode over the course of one year or more. The therapeutic agent (including a chemotherapeutic agent), can be encased and/or impregnated in the polymer anchoring member or reside as a film layer disposed on the outer surface of the anchoring member. In some embodiments, the polymer anchoring member can be encased within a polymer film (i.e., layers of film could reside on either side of the frame and those layers are bonded together with the stent sandwiched in between).

According to some embodiments of the present technology, the treatment device may comprise mainly flexible materials (e.g., a polymer, a drug-eluting fabric, etc.), that would allow the device to conform to the shape/topography of the tumor, adjust as the shape/topography of the tumor changes in response to the therapeutic agent, and perhaps most importantly, conform to the shape of the esophagus (which has a circular shape at rest, but ovular when squeezed). Additional benefits include ability to have a smaller constrained diameter. Other embodiments may be non-conforming or partially conforming, allowing some flexibility for swallowing but preventing the tumor from ever causing complete occlusion of the esophagus.

Figure 17A:
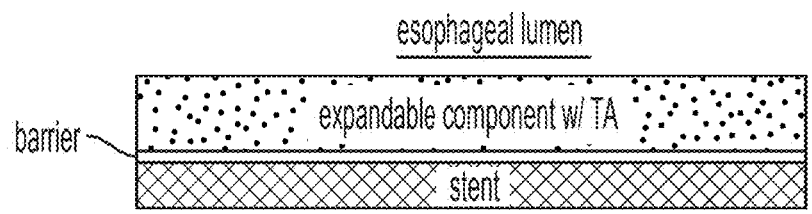
FIGS. 17A and 17B show different embodiments of treatment devices having an expandable component.
Figure 17B:
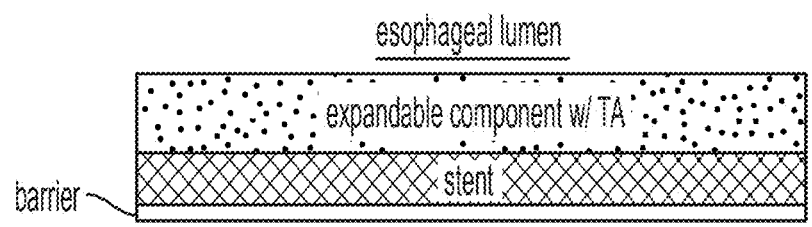

FIGS. 17A and 17B are cross-sectional views of a treatment device including an anchoring member (such as any of the anchoring members described herein) and a therapeutic member in the form of an expandable gel or hydrogel containing the therapeutic agent. The gel or hydrogel may be incorporated into the aforementioned film constructs. For example, the therapeutic member 102 may be coated or otherwise include a bioresorbable adhesive derived from polyethylene glycol (PEG or PEO), for example, or from other hydrogels. The PEG or hydrogel may also be integral to the therapeutic member via mixing in solution with the therapeutic member materials and not a separate coating. As the therapeutic member is inserted and expanded in the body, bodily fluids activate the PEG, which swells, encapsulates and adheres to the anchoring member. The expandable gel may be disposed on the anchoring member and is configured to swell to at least two times its size under physiologic conditions so that the gel pushes through the openings in the wall of the anchoring member. Such an embodiment may be beneficial as esophageal tumors may deform the esophageal lumen from a generally cylindrical shape to an irregular shape, which can make it difficult for a cylindrically-shaped anchoring member to expand into full or nearly full apposition with the esophageal wall and/or tumor. As such, often times gaps remain between the anchoring member and the esophageal wall and/or tumor. The treatment device shown in FIGS. 17A and 17B address this challenge by allowing the gel to expand into those spaces, thereby providing a more effective release of the therapeutic agent. The gel or hydrogel may also act as an adhesive to firmly secure the assembly to the tissue. The gel or hydrogel may be delivered separately from the anchoring and therapeutic members. For example, a balloon may be coated with a hydrogel, expand the anchoring member and coat the anchoring member simultaneously. The therapeutic member may be sequentially deployed against the hydrogel coated anchoring member. The reverse deployment may occur also, such that the anchoring member is expanded against the hydrogel coated therapeutic member.

Figure 18:
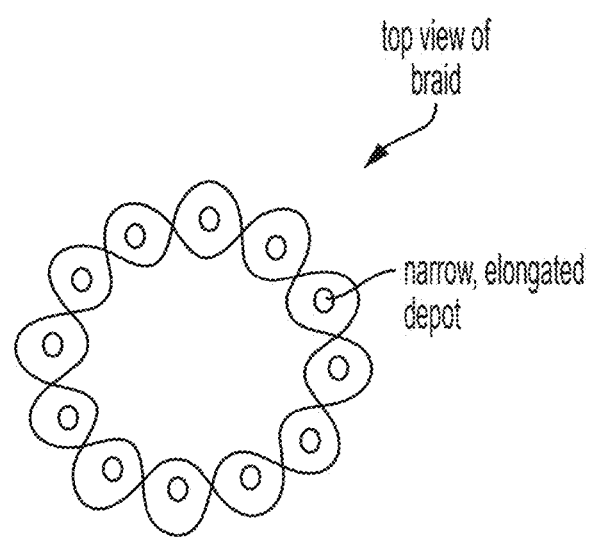
FIG. 18 is an end view of a treatment device in accordance with the present technology.

FIG. 18 is a cross-sectional end view of a treatment device configured in accordance with the present technology. In some embodiments, the treatment device may include an anchoring member formed of a generally tubular mesh structure comprising a plurality of braided or woven filaments that overlap one another along the length of the anchoring member. The treatment device may further include one or more elongated, generally cylindrical therapeutic members extending along the length of the device and positioned between the overlapping filaments. These longitudinal elements may be incorporated into the braided structure during the initial braiding process, or they may be threaded into the braid at a later point in the production process. In some embodiments, such elongated therapeutic members may be incorporated into the woven tubular member by manual placement once the woven member has been braided by conventional means, or a braiding machine may be configured to automatically feed the longitudinal members into the braiding process, achieving the incorporation of therapeutic members automatically.

Figure 19:
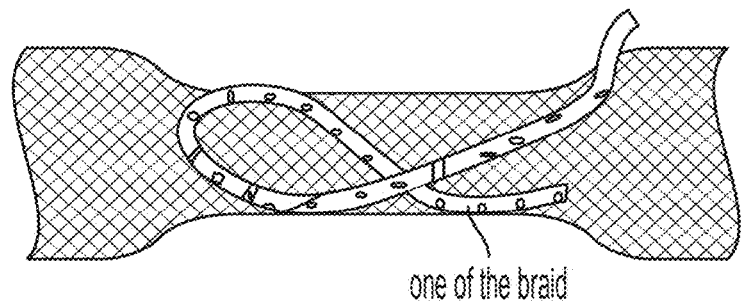
FIG. 19 is a side view of a treatment device in accordance with the present technology.

In some embodiments, the treatment device may be delivered to the treatment site in the form of a liquid. FIG. 19, for example, shows one such embodiment in which the treatment device includes an anchoring member formed of a plurality of braided or woven filaments. At least one of the plurality of filaments is a hollow a tube having a plurality of openings along its length. The distal end of an elongated delivery member may be coupled to the proximal end of the hollow filament and/or coupled to an adapter that couples the delivery member to multiple hollow filaments. A proximal end of the delivery member may be positioned at an extracorporeal location. The therapeutic member can be delivered through the hollow filament(s) such that the therapeutic member flows through the openings to deliver the therapeutic agent at the treatment site.

Figure 20:
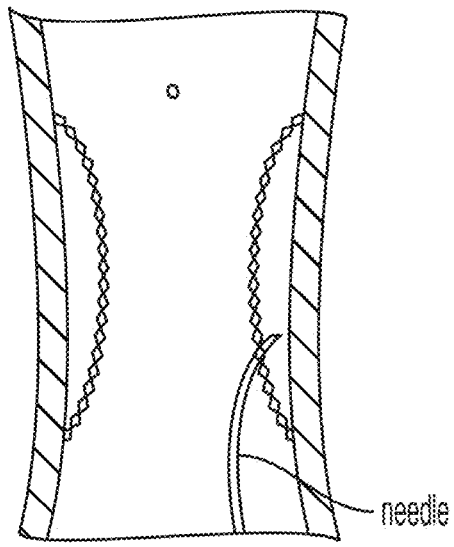
FIG. 20 is a cross-sectional view of a treatment device in accordance with the present technology, shown positioned within the esophagus in an expanded state.

FIG. 20 is a cross-sectional view of a treatment device configured to deliver a therapeutic agent in liquid or gel form. In some embodiments, the treatment device may include an anchoring member having a cover at its outer surface and flared ends such that at least a portion of the body of the anchoring member is spaced apart from the esophageal wall and/or tumor, thereby creating a space between the anchoring member and the esophageal wall and/or the tumor. In some embodiments, a delivery device, such as an elongated shaft or needle, could be delivered to the treatment site, and a distal portion of the delivery device could be advanced through an opening in the mesh structure of the anchoring member and through the cover. A therapeutic agent could then be delivered via the delivery device into the space between the anchoring member and the esophageal wall and/or tumor.

In cases of recurrence, a drug-eluting balloon may be delivered to the treatment site and expanded within the lumen of the anchoring member to improve luminal patency, deliver a therapeutic agent, and/or position a new therapeutic member.

A variety of delivery systems known in the art may be employed to deliver a therapeutic and anchoring member transluminally including those incorporating a balloon, guidewire and catheter-based system.

In some embodiments, the treatment device may be configured to provide photodynamic therapy (PDT). For example, in some embodiments, the therapeutic member may include one or more photosensitizing agents (e.g., porphyrins, chlorins, and dyes) configured to elicit cell death when exposed to a specific wavelength of light. Photosensitizing agents provide several advantages over chemotherapeutic agents, including increased cytotoxicity and minimal or no resistance. To activate the photosensitizing agent, the clinician may activate a light source positioned within the patient's body (i.e., within the esophageal lumen), and/or a light source positioned at an extracorporeal position. The light source may be a laser, light-emitting diode (LED), or other suitable light source. For example, in some embodiments, the light source is a laser directed through a fiber optic cable (e.g., via an endoscope) to the implanted therapeutic member. In other embodiments, the light source may be coupled to the treatment device. In some embodiments, the light source is coupled to or integrated with the treatment device (e.g., via the anchoring member) such that the light source is delivered to the treatment site with the treatment device. The implanted light source may be activated via an external control, in response to local physiologic conditions, automatically after a predetermined amount of time, and other suitable means. The therapeutic member for these embodiments may be completely opaque, so that the applied light causes only activation of the photosensitizing agent which has already been released into the tumor. After a period of time, additional un-activated photosensitizing agent will be released from the therapeutic member into the tumor, and the light activation process can be repeated.

In some cases it may be desirable to remove the treatment device after several months, especially when the local release of chemotherapeutic agents (by the therapeutic member) is very effective in preventing or slowing tumor growth, and/or causing the tumor to regress. In these and other scenarios, it may be desirable to replace the treatment device with a new one having at least a new therapeutic member and the same or different anchoring member (if the anchoring member is used). In some embodiments, the anchoring member and/or therapeutic member may have a textured outer surface to reduce or prevent migration and that does not allow ingrowth. In some embodiments, the therapeutic member and/or anchoring member may have a few loops at one end or the other to allow the device to be grabbed, re-compressed, and removed. In some embodiments, it may be desirable to leave the therapeutic member and anchoring member in the patient, but allow for the treatment portion of the therapeutic member to be replaced or supplemented by a new treatment portion.

Figure 21:
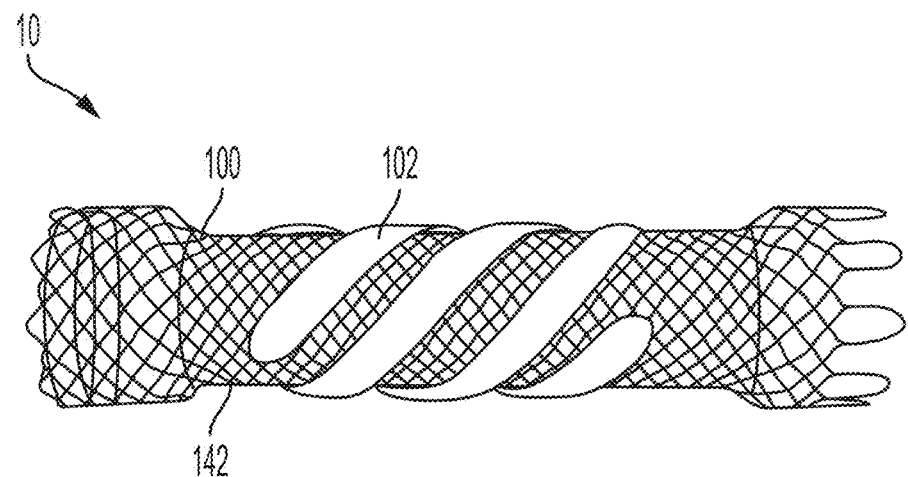
FIG. 21 shows a treatment device in accordance with the present technology, shown in an expanded state in accordance with the present technology.
Figure 22:
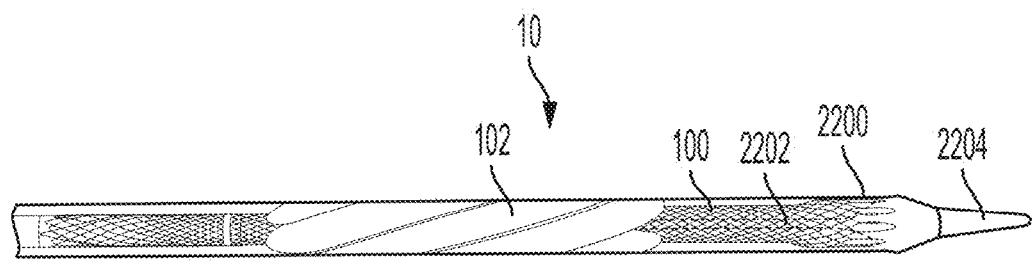
FIG. 22 shows the treatment device of FIG. 21 in a collapsed state positioned within a delivery sheath, in accordance with the present technology.

FIG. 21 shows an embodiment of a treatment device 10 of the present technology in the expanded state, and FIG. 22 shows the treatment device 10 in a collapsed state positioned within a delivery sheath 2200. As shown in FIGS. 21 and 22, the therapeutic member 102 comprises a treatment portion comprising a strip that curls around a central longitudinal axis of the anchoring member 100 such that, when the treatment device 10 is implanted within a body lumen (such as an esophagus), the strip curves around and is in contact with an inner surface of the wall defining the body lumen. The strip may be any of the films and/or treatment portions described herein. The strip may be attached to the anchoring member 100 such that the therapeutic region releases the drug towards the wall of the body lumen. For example, the strip may be arranged such that the therapeutic region is radially outward of the base region (i.e., the base region is closer to or in direct contact with the anchoring member 100). The treatment portion may optionally include a control region. In such embodiments, the strip may be positioned such that the control region is between therapeutic region and the wall of the body lumen and/or tumor when the device 10 is implanted within the body lumen.

As best shown in FIG. 21, the strip may form helical windings that wrap multiple times around the anchoring member 100. In some embodiments, the strip curves around only a portion of the circumference of the anchoring member, or only a single time around the anchoring member 100. Adjacent windings of the strip may be spaced apart in the expanded state (as shown in FIG. 21), or in some embodiments may abut or overlap one another. In some aspects of the technology, some or all of the windings of the strip are parallel to the windings comprising the struts or braided wires of the anchoring member. As such, the strip elongates to collapse with the anchoring member 100 and compresses to expand with the anchoring member 100.

The strip may be sewn, adhered, or otherwise coupled to the anchoring member 100 along all or a portion of the length of the strip 102 and/or length and/or circumference of the anchoring member 100. In some embodiments, the therapeutic member and/or treatment portion is a standalone device. The treatment device 10 may further include a polymer and/or fabric cover 142 at an interior surface of the anchoring member, as shown in FIG. 21. In some embodiments, the treatment device 10 may additionally or alternatively include a cover at an exterior surface.

As shown in FIG. 22, the treatment device 10 of FIG. 21 may be configured to fit in a collapsed state within a delivery sheath 2200. An elongated member 2202 may extend through a central lumen of the anchoring member 100 and attach to a nosecone 2204 at its distal end. A proximal portion of the nosecone 2204 may contain a distal portion of the self-expandable anchoring member 100.

Figure 23A:
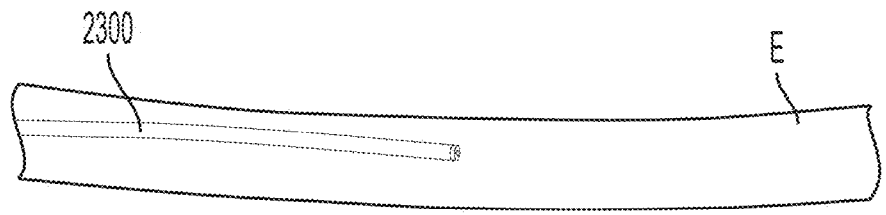
FIGS. 23A-23G depicts a method for positioning the treatment device of FIG. 21 in a body lumen in accordance with the present technology.
Figure 23B:
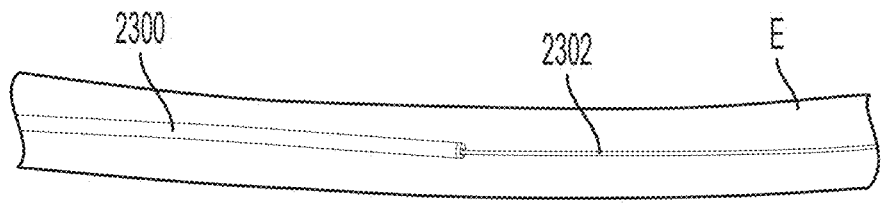
Figure 23C:
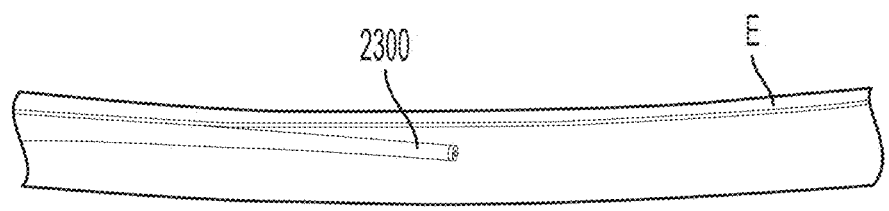
Figure 23D:
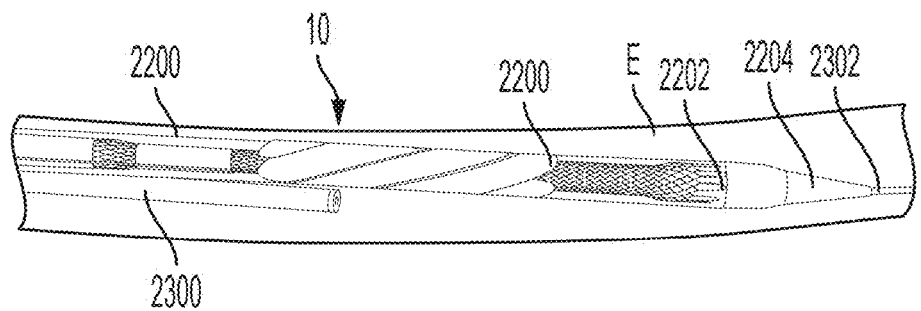
Figure 23E:
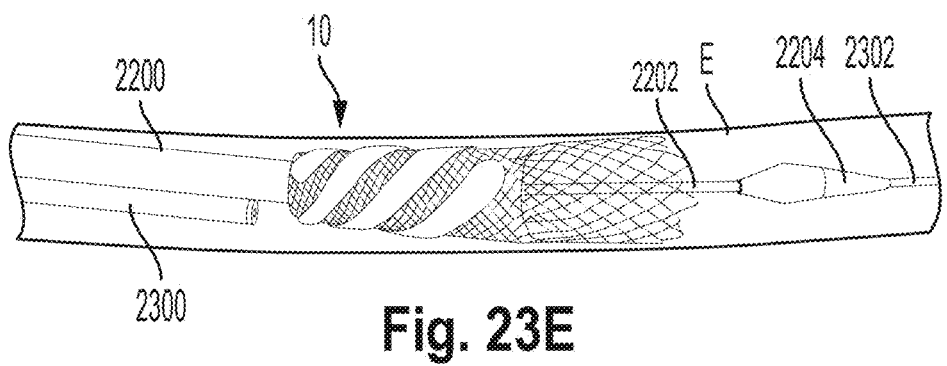
Figure 23F:
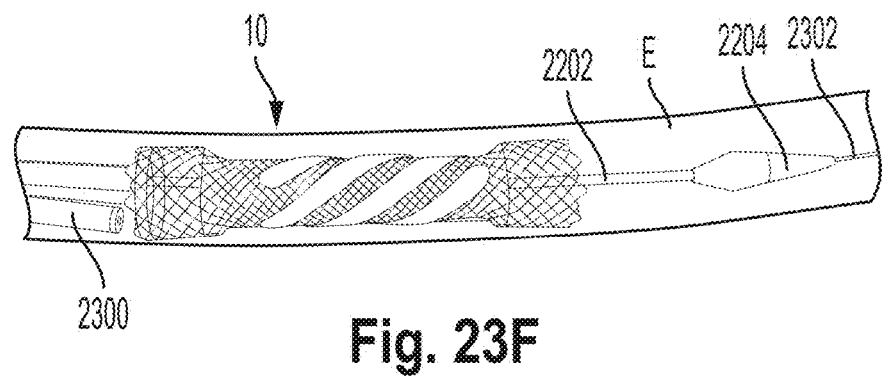
Figure 23G:
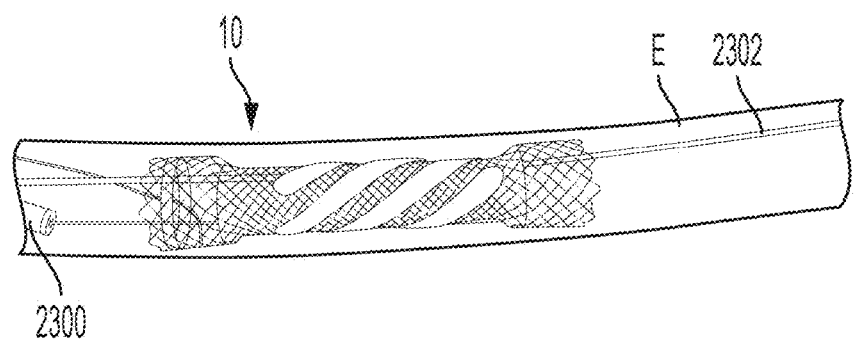
Figure 24:
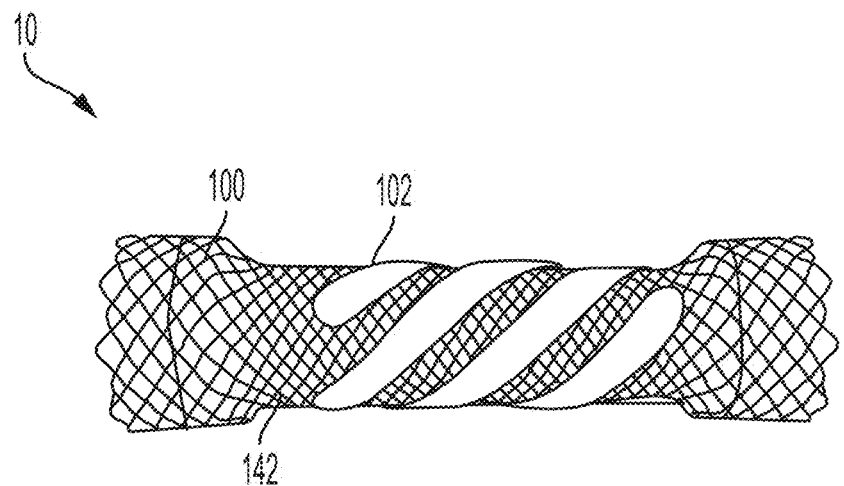
FIG. 24 shows a treatment device in accordance with the present technology, shown in an expanded state in accordance with the present technology.
Figure 25:
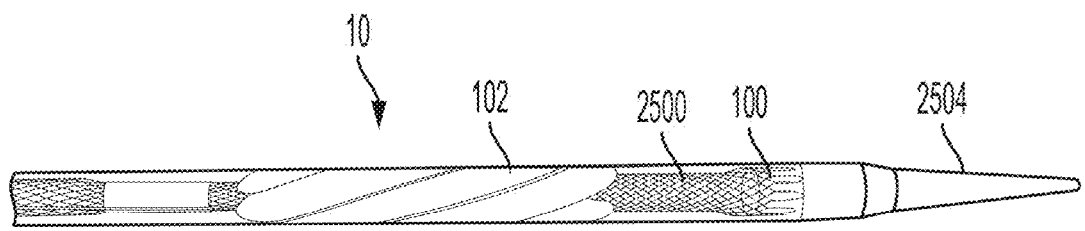
FIG. 25 shows the treatment device of FIG. 24 in a collapsed state positioned within a delivery sheath, in accordance with the present technology.
Figure 26A:
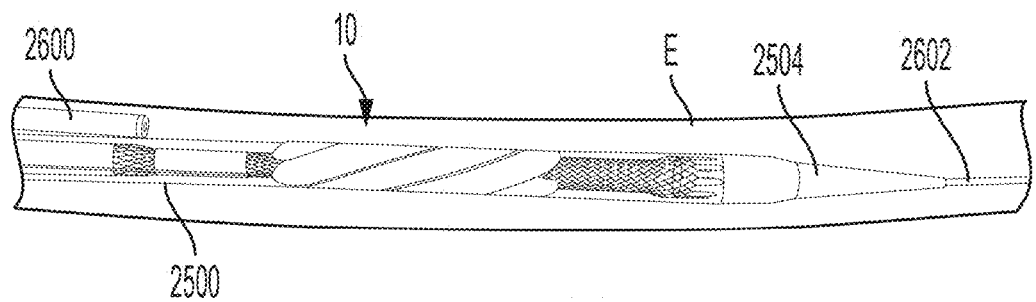
FIGS. 26A-26D depicts a method for positioning the treatment device of FIG. 24 in a body lumen in accordance with the present technology.
Figure 26B:
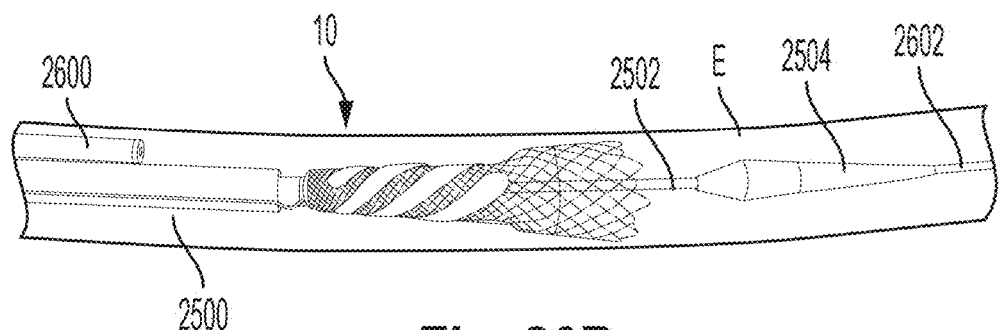
Figure 26C:
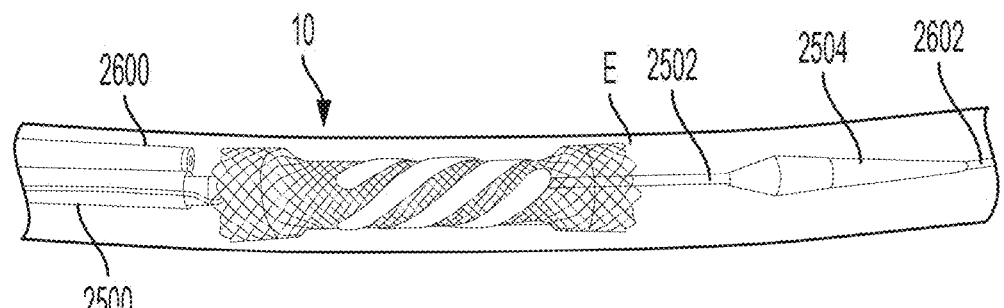
Figure 26D:
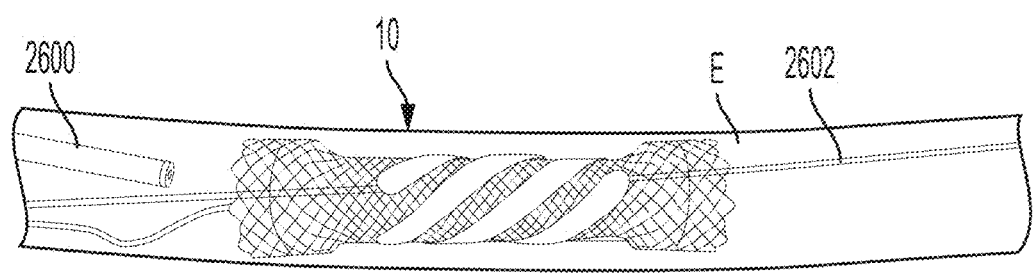

FIGS. 23A-23G depict a method for deploying the treatment device 10 within a body lumen E. As shown in FIGS. 23A-23C, a catheter 2300 may be advanced to a treatment site and a guidewire 2302 may be advanced to the treatment site through the catheter 2300. Once at the treatment site, the treatment device 10 may be advanced over the guidewire 2302. As shown in FIGS. 23D-23G, while holding the elongated member 2202 in place, the delivery sheath 2200 may be withdrawn to allow the treatment device 10 to expand such that the strip is in contact with a portion of the tumor and/or wall defining the body lumen.

The treatment device 10 and delivery system (and associated method for delivery) shown in FIGS. 24-26D may be generally similar to the treatment device 10 and associated delivery system and method shown in FIGS. 21-23G, except with a larger diameter anchoring member.

Figure 27A:
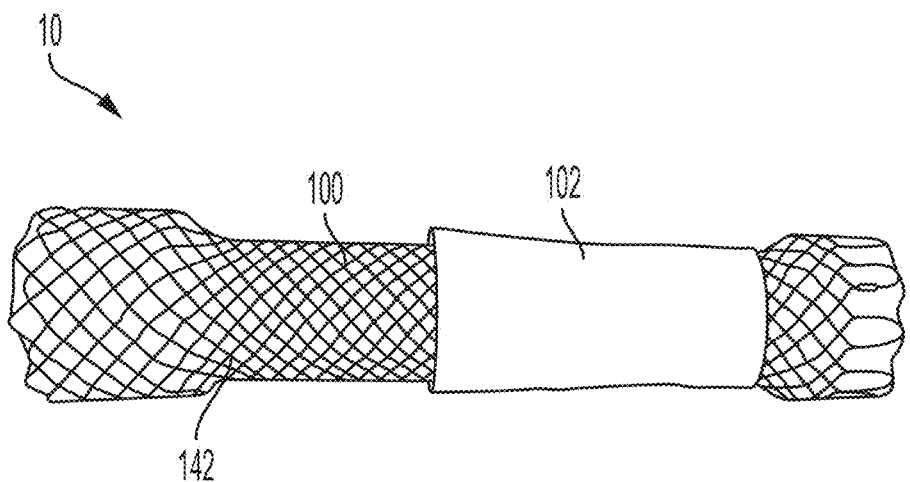
FIGS. 27A-27B show different views of a treatment device in accordance with the present technology.
Figure 27B:
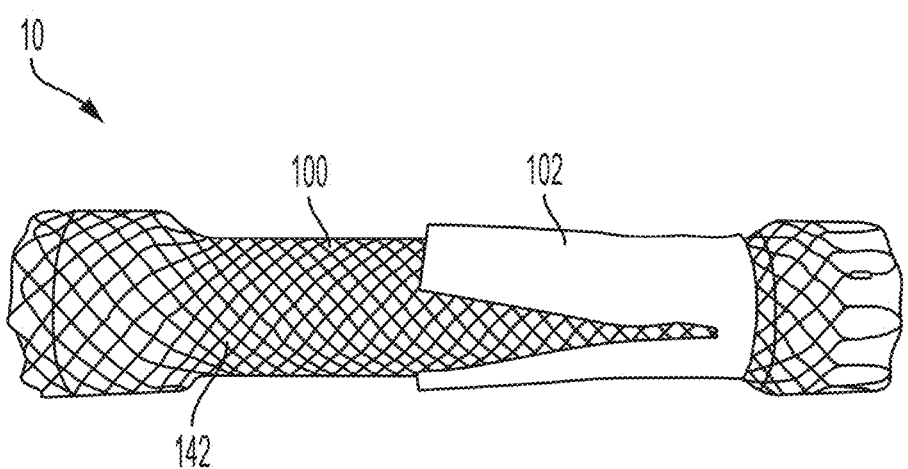

FIGS. 27A and 27B are different views of a treatment device 10 having a therapeutic member 102 comprising only a treatment portion. The treatment portion may be a sheet that is wrapped around the circumference of the anchoring member 100. The sheet may comprise any of the treatment portions and/or films described herein. The edges of the sheet that extend axially along the anchoring member 100 may not be attached such that they are free to move independently of one another. As shown, in some embodiments only the distal end of the sheet may be attached to the anchoring member 100 and the proximal end of the anchoring member may not be attached such that it is free to move relative to the anchoring member. In some embodiments, only the proximal end of the sheet may be attached to the anchoring member, or both ends of the sheet may be attached to the anchoring member.

Figure 28:
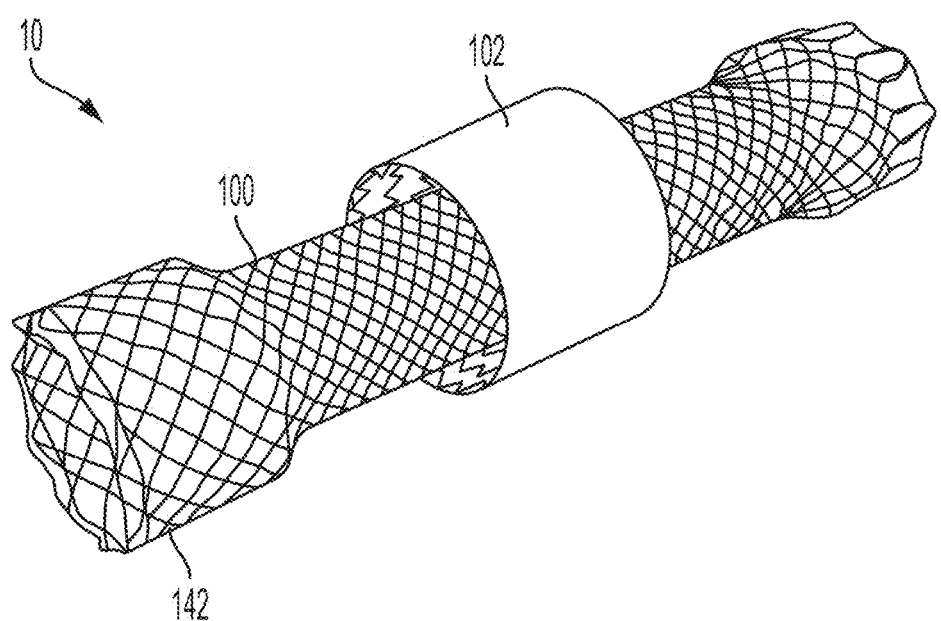
FIG. 28 is a perspective view of a treatment device in accordance with the present technology.

FIG. 28 is a perspective view of a treatment device 10 comprising an anchoring member 100 and a therapeutic member 102. In FIG. 28, the therapeutic member 102 is shown positioned over the anchoring member 100. The anchoring member 100 and the therapeutic member 102 may be delivered to the treatment site separately or simultaneously. The therapeutic member 102 may include a support member 198 (such as a stent) covered by a treatment portion 198 (such as any of the treatment portions and/or films described herein).

Figure 29A:
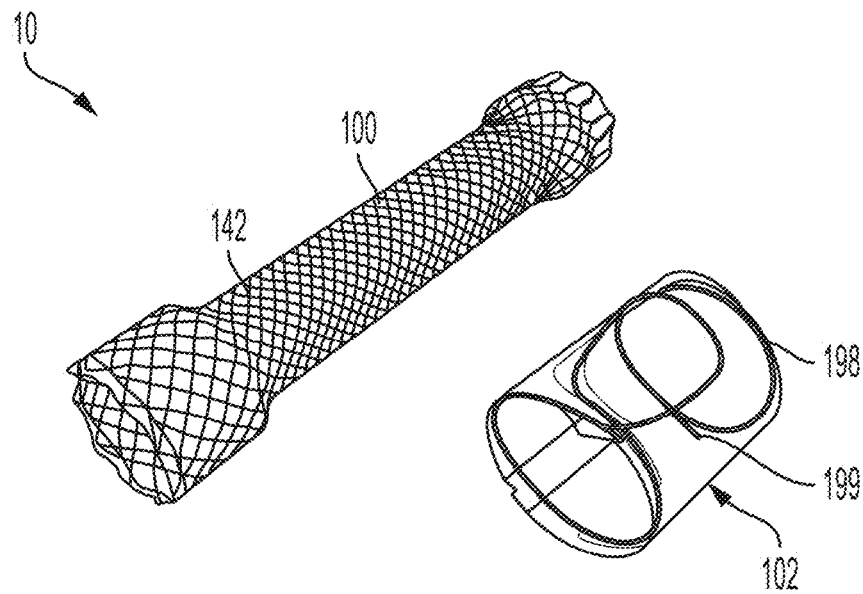
FIGS. 29A-29B are perspective views of a treatment device in accordance with the present technology.
Figure 29B:
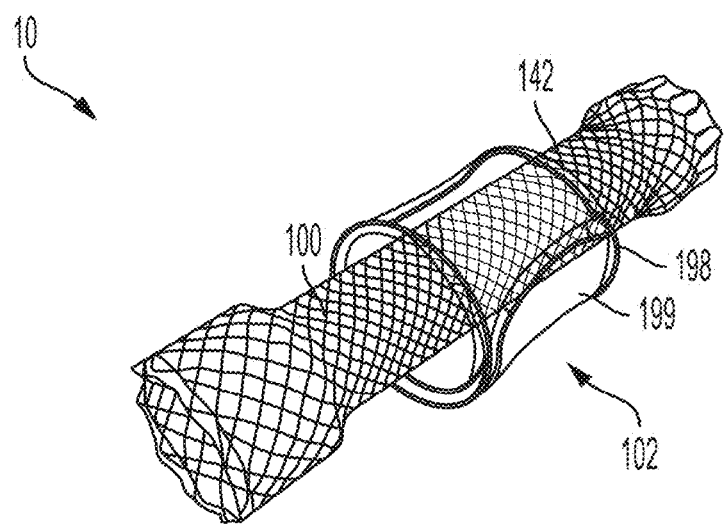

FIGS. 29A-29B are perspective views of a treatment device 10 comprising an anchoring member 100 and a therapeutic member 102 in accordance with the present technology. In FIG. 29A, the therapeutic member 102 is shown separated from the anchoring member 100, and in FIG. 29B, the therapeutic member 102 is shown positioned over the anchoring member 100. The anchoring member 100 and the therapeutic member 102 may be delivered to the treatment site separately or simultaneously. The therapeutic member 102 may include a treatment portion 199 (such as any of the treatment portions and/or films described herein) in the form of a strip that curls onto itself in the expanded configuration. The therapeutic member 102 may further include a support member 198 extending along only a periphery of the strip. The strip may curl about itself such that its longitudinal edges overlap (as shown), or the strip may curl about itself to form a 'C' shape or cuff such that its longitudinal edges are spaced apart.

Figure 31A:
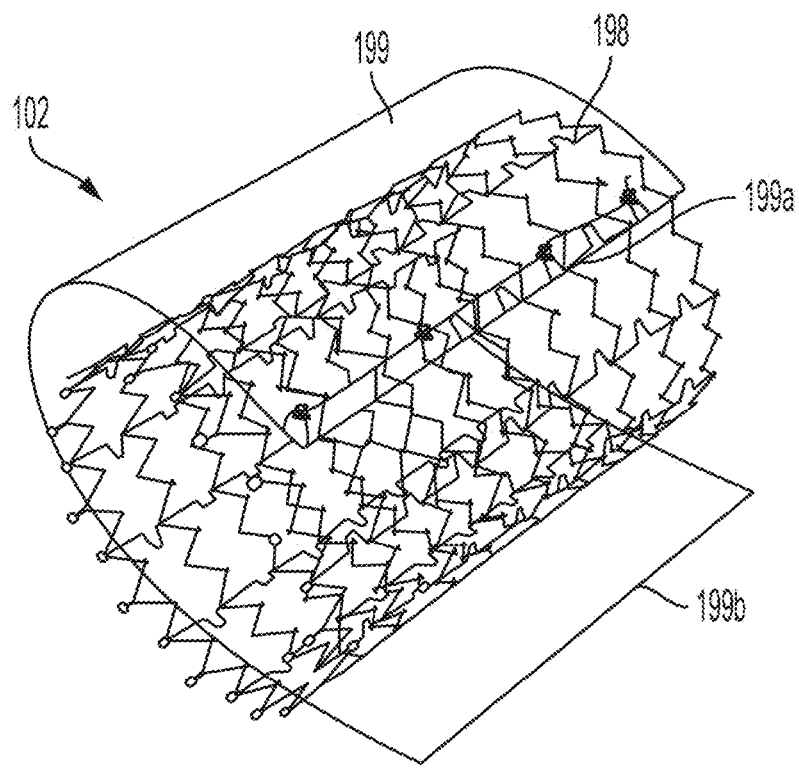
FIGS. 31A and 31B are perspective and top views, respectively of a therapeutic member in accordance with the present technology.
Figure 31B:
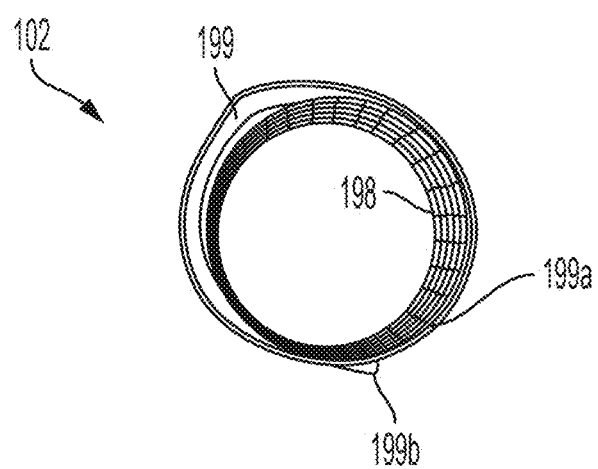

FIGS. 31A and 31B are perspective and top views, respectively, of a therapeutic member 102 of the present technology comprising a support member 198 and a treatment portion 199 in the form of a strip that is wrapped around the support member 198. The strip extends between two longitudinal ends 199a and 199b and has a width extending between lateral edges. The width of the strip may be the same or different (greater or less than) than the width of the support member 198. As shown, one of the longitudinal ends of the strip may be attached to the support member 198, and the other longitudinal end of the strip may be free (i.e., not attached to the support member 198). The strip may curl over itself in the expanded configuration such that the longitudinal ends overlap. In some embodiments, the longitudinal ends of the strip do not overlap and are spaced apart about the circumference of the support member 198.

Figure 30:
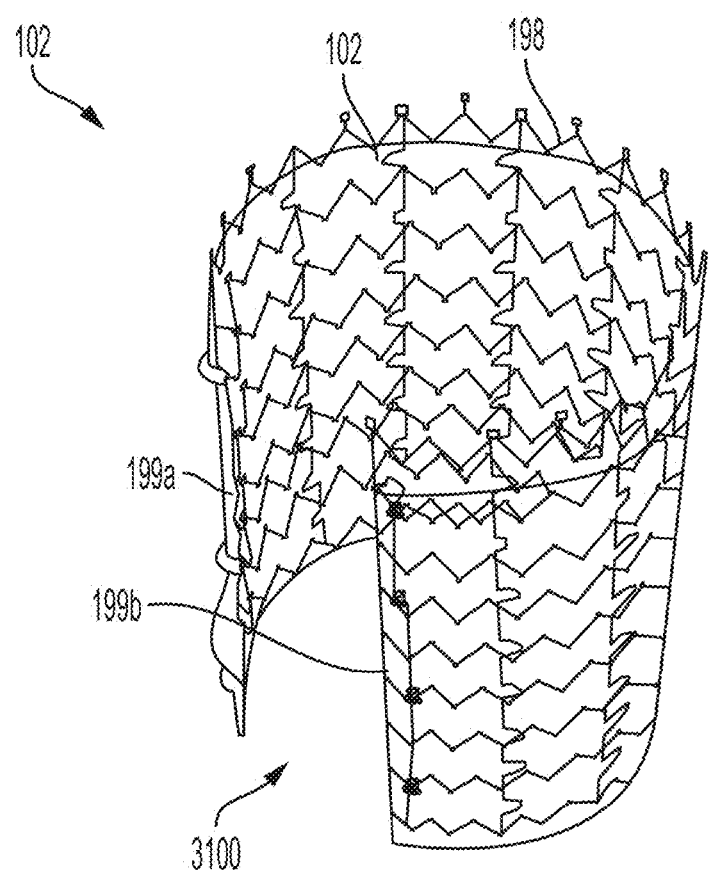
FIG. 30 is a perspective view of a therapeutic member in accordance with the present technology.

FIG. 30 shows a therapeutic member 102 that is similar to the therapeutic member of FIGS. 31A and 31B, except the support member 198 is a cuff and has circumferential edges that are spaced apart. The longitudinal ends 199a, 199b of the strip 199 may also be spaced apart such that the strip forms a cuff.

Figure 32A:
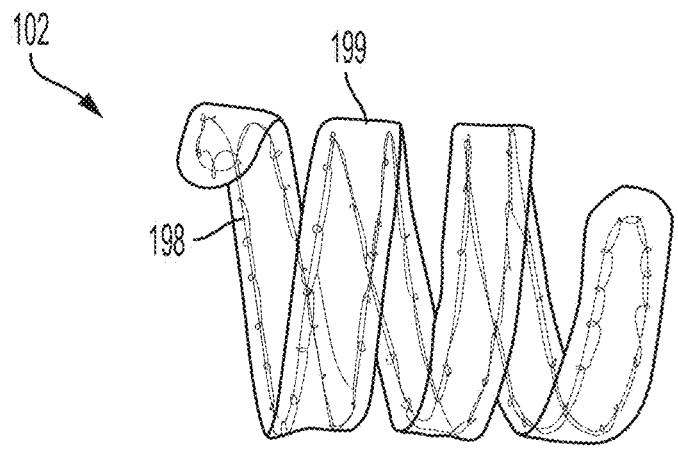
FIG. 32A is a therapeutic member in an expanded state in accordance with the present technology.
Figure 32B:
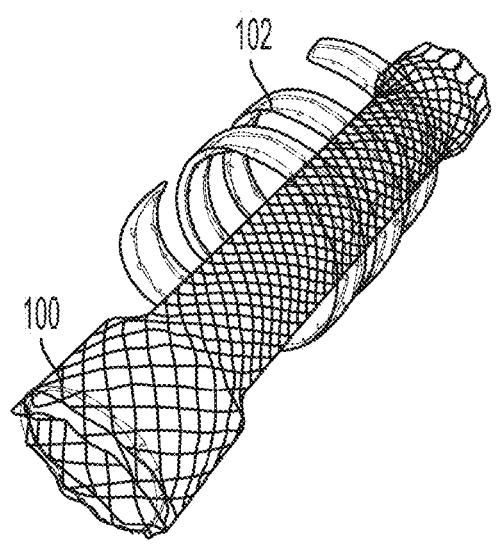
FIG. 32B is a treatment device including a therapeutic member of FIG. 32A in accordance with the present technology.
Figure 33A:
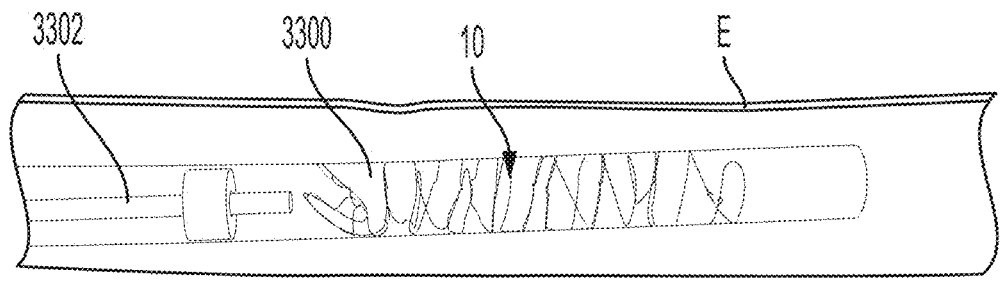
FIGS. 33A-33C depict a method for positioning the therapeutic member of FIG. 32A in a body lumen in accordance with the present technology.
Figure 33B:
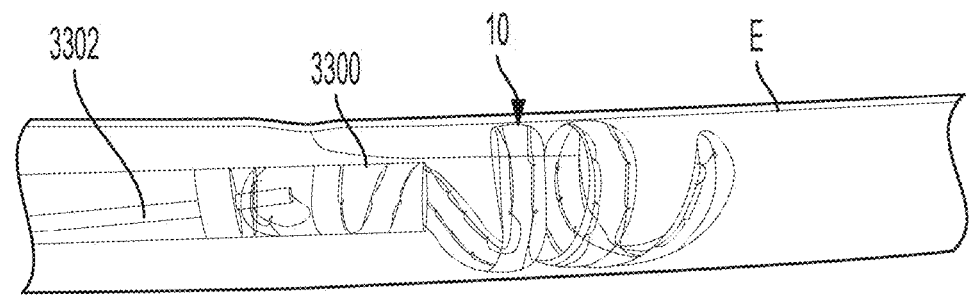
Figure 33C:
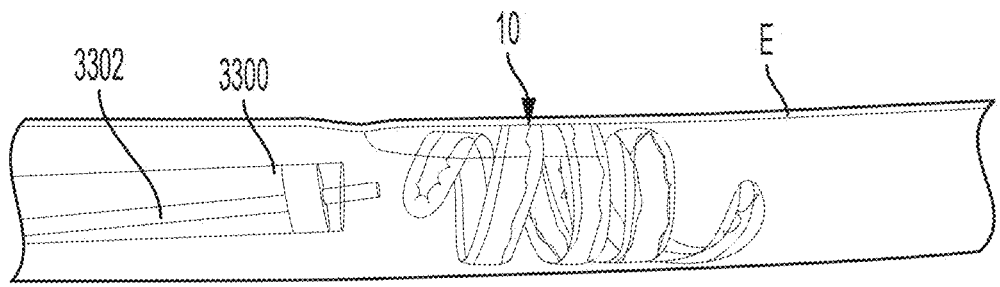
Figure 34A:
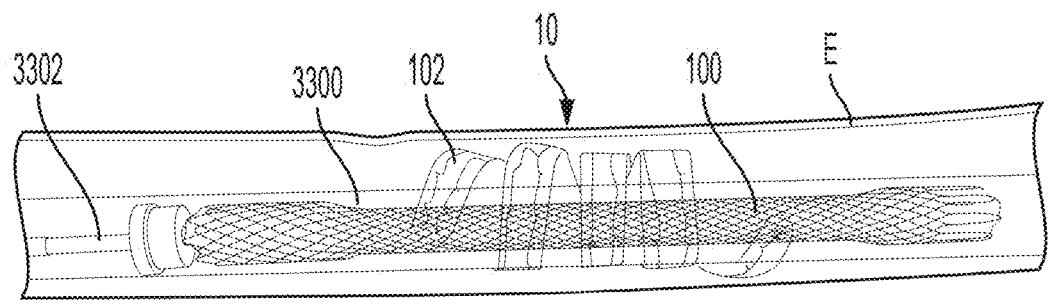
FIG. 34A-34B depict a method for positioning the treatment device of FIG. 32B in a body lumen in accordance with the present technology.
Figure 34B:
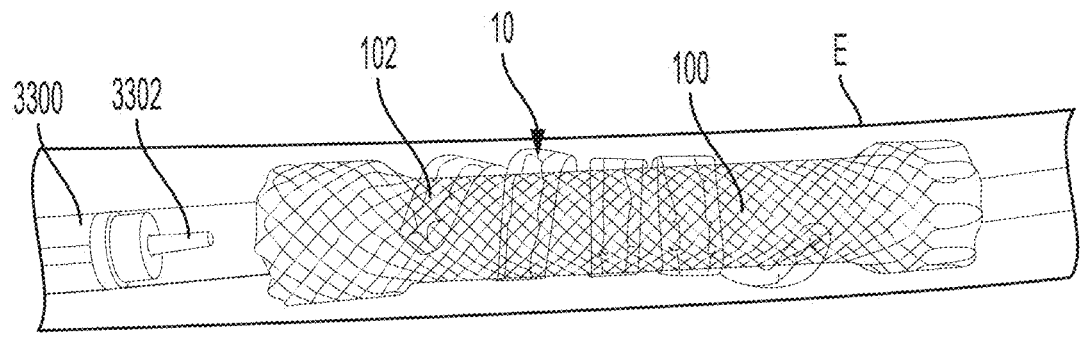

FIG. 32A is a side view of a therapeutic member 102 comprising a treatment portion formed of a spiral strip, and a support member 198 extending along the periphery of the strip. FIG. 32B shows the therapeutic member 102 positioned over an optional anchoring member 100. The anchoring member 100 and the therapeutic member 102 may be delivered to the treatment site separately or simultaneously. FIGS. 33A-33C depict a method for delivering and expanding the therapeutic member 102 of FIG. 32A to a treatment site independent of an anchoring member. For example, the therapeutic member 102 may be positioned within a delivery sheath (not shown) and the delivery sheath withdrawn to allow the therapeutic member 102 to expand. As shown in FIGS. 34A-34B, the anchoring member 100 may be delivered to the treatment site in a collapsed state within a delivery sheath 3300 and positioned within a lumen of the already-expanded therapeutic member. A proximal end of the anchoring member 100 may be coupled to a distal end of an elongated member 3302 also extending through the sheath 3300. The sheath 3300 may be proximally withdrawn, thereby allowing the anchoring member 100 to expand.

Figure 35A:
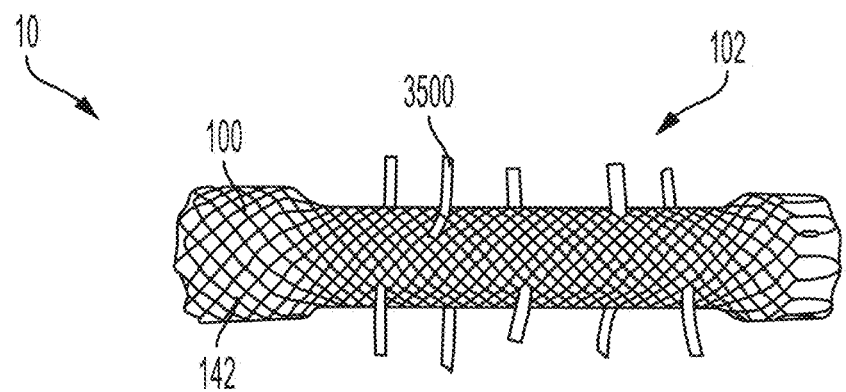
FIG. 35A-35B are side and perspective views in accordance with the present technology.
Figure 35B:
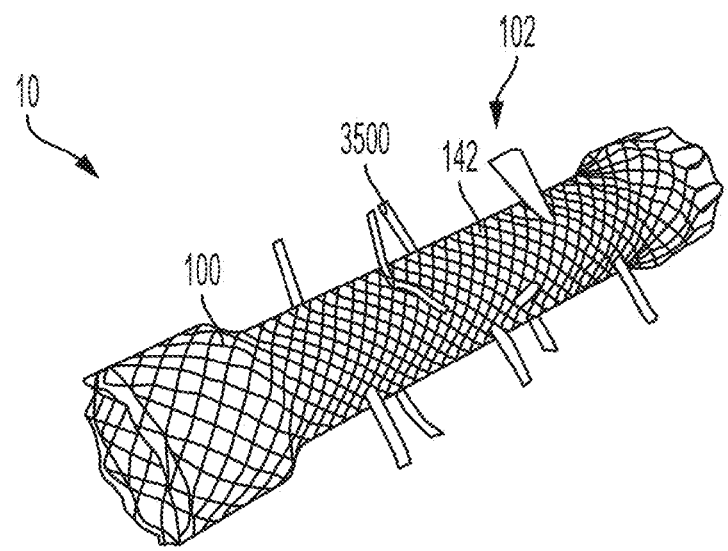

FIGS. 35A-35B are side and perspective view of a treatment device 10 configured in accordance with the present technology. The treatment device 10 may comprise an anchoring member 100 and a therapeutic member 102 in the form of a plurality of strips 3500 extending radially outwardly from the anchoring member 100.

Figure 36:
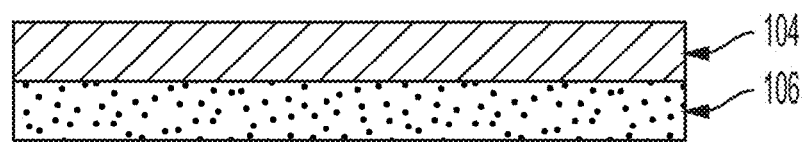
Figure 37:
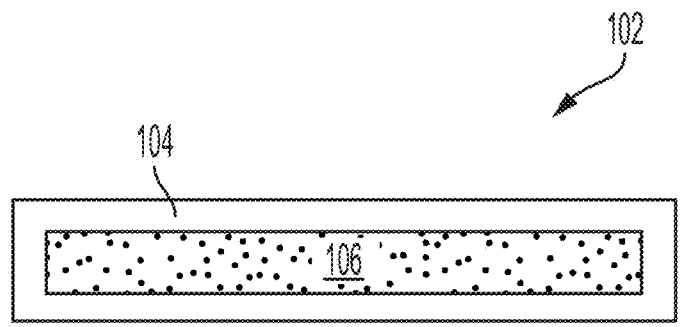

FIGS. 36-45 show various embodiments of treatment portions (or films) for use with the therapeutic members 102 and/or treatment devices 10 of the present technology. For example, as shown in FIG. 36, the treatment portion may comprise a film comprising a control region 104 positioned on a therapeutic region 106 such that at least a portion of the therapeutic region 106 is exposed. FIG. 37 shows a therapeutic member 102 and/or treatment portion comprising a therapeutic region 106 completely encapsulated by a control region 104. As a result, the control region 104 substantially prevents contact between the chemotherapeutic agent and physiologic fluids, thereby preventing an uncontrolled, burst release of the chemotherapeutic agent when implanted. Over time, the releasing agent imbedded in the polymer of the control region contacts physiologic fluids and dissolves, thereby forming micro-diffusion openings in the control region. The combination of the restriction imposed by the control region and the micro-diffusion openings formed by dissolution of the releasing agent enables a controlled, linear release of the therapeutic agent from the depot over the course of several days, weeks, or months. Although the therapeutic member 102 is shown as a rectangular, thin film in FIGS. 36-45, in other embodiments the therapeutic member 102 may have other shapes, sizes, or forms In various embodiments of the therapeutic member 102 and/or treatment portion described herein, for example as depicted in FIGS. 38A-38D, the control region may take several different forms. In one embodiment, depicted in FIG. 38A, the control region may comprise a single layer of biodegradable, bioresorbable polymer mixed with a releasing agent. In an alternative embodiment, depicted in FIG. 38B, the control region itself may comprise a structure having multiple layers of biodegradable, bioresorbable polymer. The multiple layer structure depicted in the control region of FIG. 38B may be a few as two layers of biodegradable, bioresorbable polymer or as many as 10 or 15 layers or more. The layers of this multiple layer structure may additionally or alternatively comprise multiple microthin sheets or layers (i.e., microlayers), where each microthin layer has a thickness of from approximately 5 µm to 100 µm, 5 µm to 50 µm, 5 µm to 25 µm, 5 µm to 10 µm, 5 µm to 7 µm or 7 µm to 9 µm. In this embodiment of the control region, at least one layer of the multilayer structure may comprise a polymer mixed with a releasing agent and at least one other layer of the multilayer structure may comprise a polymer having no releasing agent mixed therein. In still another alternative embodiment of the control layer of the multilayer film, depicted in FIG. 38C, the control layer may comprise a multilayer structure wherein multiple layers have a releasing agent mixed into each polymer layer, but these layers may have the releasing agent in different concentrations. Alternatively, in an embodiment of a control layer having a multilayer structure depicted in FIG. 38D, multiple layers have a releasing agent mixed into each polymer layer, but these layers may have different releasing agents.

In various embodiments of the therapeutic member 102 and/or treatment portion described herein, for example as depicted in FIGS. 39A-39E, the therapeutic region may take several different forms. In some embodiments, as shown in FIG. 39A, the therapeutic agent layer may comprise a layer of essentially pure therapeutic agent, or a pharmaceutically acceptable salt thereof, only (i.e., no polymer or other agents). In an alternative embodiment, as shown in FIG. 39B, the therapeutic agent layer may comprise a single layer of polymer loaded with a therapeutic agent. In this embodiment, the therapeutic agent may be dissolved into the polymer which is then applied as a single layer to the film construct via any number of methods (e.g., dip coating, spray coating, solvent casting, etc.). Alternatively, the therapeutic agent may be imbedded or impregnated in the polymer layer in a solid, fibrous or particulate form.

In an alternative embodiment of the therapeutic agent layer, depicted in FIG. 39C, the therapeutic agent layer may comprise a microlayer structure of multiple micro-thin sheets of biodegradable, bioresorbable polymer, each micro-thin sheet (or layer) loaded with therapeutic agent. In this microlayer embodiment of the therapeutic agent layer, the micro-thin sheets have a substantially uniform construction and are stacked and bonded together. These micro-thin polymer sheets may each have a thickness from approximately 5 μm to 100 μm, 5 μm to 50 μm, 5 μm to 25 μm, 5 μm to 10 μm, 5 μm to 7 μm, or 7 to 9 μm thick, with the overall thickness of the therapeutic agent layer based on the total number of micro-thin sheets that are stacked. Due to heat compression bonding, the thickness of the total microlayer structure will be less than the sum of the thicknesses of each micro-thin sheet. The reduction in thickness of the microlayer structure from the sum of the thicknesses of each micro-thin sheet may be 50%, 40%, 30%, 25% or 20%. As described below in greater detail, this multilayer structure of the therapeutic agent layer may provide increased control over therapeutic agent release kinetics. In an alternative embodiment to the therapeutic agent layer having a multi-layer or microlayer structure, depicted in FIG. 6D, the individual sheets or layers of the therapeutic agent layer may not have uniform construction or properties. In this configuration, each sheet may have differences in dimensions (e.g., thickness), polymer composition, relative proportion/concentration of polymer to therapeutic agent to releasing agent (optional), etc., in order to achieve the most clinically desirable release kinetics. In still an alternative embodiment, depicted in FIG. 6E, the therapeutic agent layer may comprise electrospun nanofibers made of a biodegradable, bioresorbable polymer that is loaded with therapeutic agent.

In other embodiments of the multilayer film, the therapeutic agent layer may comprise more than one therapeutic agent. In such embodiments, the therapeutic agent layer may comprise a first therapeutic agent and a second therapeutic agent, wherein the multilayer film is configured to release from the therapeutic agent layer the first and second therapeutic agents at the same time. This configuration may be particularly useful in treatments where multi-modal pharmacological therapy is clinically indicated. For example, the management of postoperative pain generally calls for the surgeon to administer a "cocktail" of select therapeutic agents (e.g., local anesthetic, NSAID, and the like) to the surgical site at the conclusion of a surgery. In another example, the treatment or prevention of infection often indicates the administration of multiple antibiotics (e.g., vancomycin, tobramycin, gentamicin, rifampin, minocycline, and the like). In some embodiments, each of the releasing agent/polymer layers may have different releasing agents in different concentrations (see, for example, FIG. 39D). As shown in FIG. 39E, in some embodiments, one or more of the regions of the treatment portion may be formed of electrospun microfibers.

In some embodiments, the treatment portion and/or therapeutic member 102 may be configured to release the therapeutic agent in an omnidirectional manner. In other embodiments, the treatment portion and/or therapeutic member 102 may include one or more base regions 108 covering one or more portions of the therapeutic region 106 and/or control region 104, such that release of the therapeutic agent is limited to certain directions. The base region 108 may provide structural support for the treatment portion. The base region 108 may comprise a low porosity, high density of bioresorbable polymer configured to provide a directional release capability to the treatment portion. In this configuration, the substantial impermeability of this low porosity, high density polymer structure in the base region 108 blocks or impedes the passage of agents released from the therapeutic region 106. Accordingly, the agents released from the therapeutic region 106 take a path of less resistance through the control region 104 opposite from the base region, particularly following the creation of diffusion openings in the control region 104.

Figure 40:
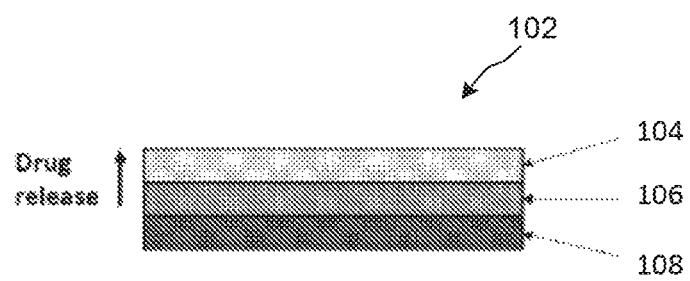

An example a treatment portion 100 of the present technology having a base region 108 is shown in FIG. 40. The base region 108 may comprise a low porosity, high density of bioresorbable polymer configured to provide a directional release capability to the multi-region treatment portion. In this configuration, the low porosity, high density polymer structure in the base region 108 blocks or impedes passage of agents release from the therapeutic region 106. Accordingly, the agents released from the therapeutic region 106 take a path of lesser resistance through the control region opposite from the base region, particularly following the creation of channels in the control region. In an additional embodiment, the porosity of other regions of the multi-region treatment portion can be varied to facilitate the release of therapeutic agent. For example, in this embodiment, the base region, the therapeutic region 106, and the control region 104 of the multi-region treatment portion depicted in FIG. 40 may have different porosities ranging from low porosity in the base region 108 to higher porosities in the therapeutic agent and control regions to facilitate the release of therapeutic agent from the multi-region treatment portion. In additional embodiments, the porosities of the edges of the multi-region treatment portion, or within portions of any of the individual regions, can be varied to properly regulate or manipulate the release of therapeutic agent.

Figure 41:
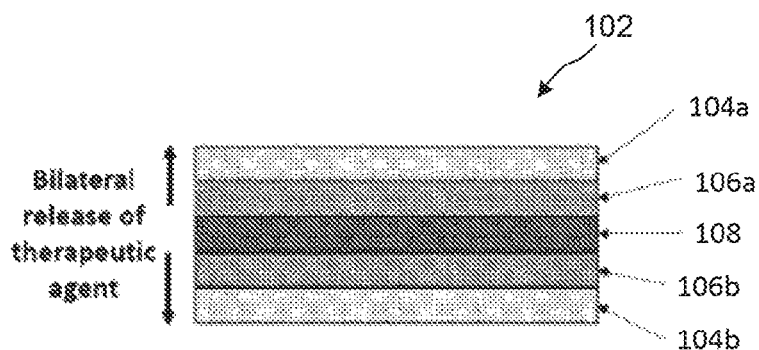
Figure 42:
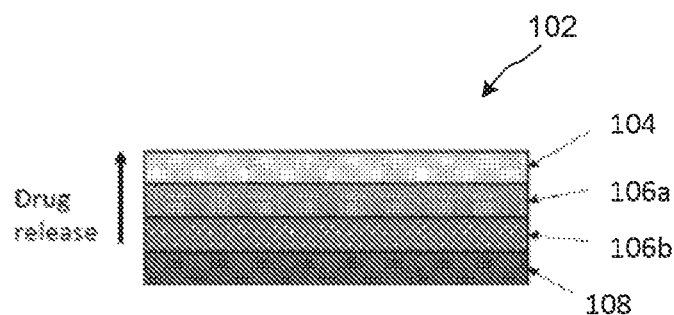

In the embodiment depicted in FIG. 41, the multi-region treatment portion provides for a bilateral or bidirectional release of therapeutic agent. This bidirectional release capability is accomplished through symmetric layering about a high density base region, wherein, as described above, the therapeutic agent releases along a path of less resistance, thereby releasing away from the high density base region. More specifically, disposed on one side of the base region 108 is a control region 104a and a therapeutic region 106a and, disposed on the other side of the base region, is a control region 104b and a therapeutic region 106b that are substantially similar to the pair on the other side. These pairs on either side of the base region 108 are configured to produce substantially equivalent, bidirectional release of therapeutic agent. In an alternate embodiment, a bidirectional release that is not equivalent (i.e., the therapeutic agent and/or rate of release in each direction is not the same) may be accomplished by asymmetric layering, whereby the control region and therapeutic region pairs on either side of the base region 108 are substantially different.

In additional embodiments, it may be desirable for the multi-region treatment portion to release multiple therapeutic agents. This capability can be particularly useful when multimodal pharmacological therapy is indicated. In the embodiment shown in FIG. 42, the multi-region treatment portion comprises a topmost or outermost control region 104a, a first therapeutic region 106a adjacent to the control region, a second therapeutic region 106b adjacent to the first therapeutic region 106a, and a base region 108 adjacent to the second therapeutic region 106b. In this embodiment, the first therapeutic region 106a and the second therapeutic region 106b comprise a first therapeutic agent and a second therapeutic agent, respectively. In certain embodiments, the first and second therapeutic agents are different. In one embodiment, the multi-region treatment portion is configured to release the first and second therapeutic agents in sequence, simultaneously, or in an overlapping fashion to yield a complementary or synergistic benefit. In this configuration, the presence and function of the control region 104a may also ensure consistent and, if desired, substantially even release of multiple therapeutic agents residing beneath. Since many conventional drug delivery devices can fail to provide an even release of multiple drugs with different molecular weights, solubility, etc., the role of the control region in achieving a substantially even release of different therapeutic agents can be a significant advantage.

In some embodiments, the first therapeutic agent and second therapeutic agent are the same therapeutic agent but are present in the first and second therapeutic regions, respectively, in different relative concentrations to represent different dosages to be administered. In some embodiments, the first and second therapeutic agents of the first and second therapeutic regions, respectively, may have no clinical association or relationship whatsoever. For example, in an embodiment for use as part of a total joint replacement (e.g., total knee arthroplasty, total hip arthroplasty) or other surgical procedure, it may be clinically desirable to administer in the vicinity of the surgical site both an analgesic (e.g., local anesthetic) to treat and better manage postoperative pain for several days or weeks following the surgery and an antibiotic to treat or prevent surgical site infection associated with the surgery or implanted prosthesis (if any) for several weeks or months following the surgery. In this embodiment, the first therapeutic region 106a may comprise a therapeutically effective dose of local anesthetic to substantially provide pain relief for no less than 3 days and up to 15 days following the surgery and the second therapeutic region 106b may comprise a therapeutically effective dose of antibiotics to substantially provide a minimally effective concentration of antibiotic in the vicinity of the surgical site for up to three months following the surgery.

Figure 43:
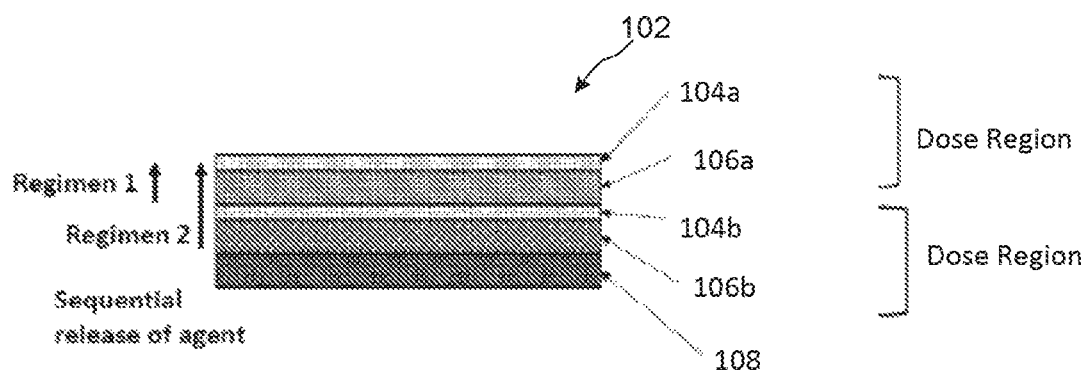

In some embodiments, as shown in FIG. 43, the treatment portion 100 comprises a first dosage region and a second dosage region, wherein the first and second dosage regions correspond to first and second dosage regimens. More specifically, each dosage region comprises a control region and therapeutic region pair, wherein each pair is configured for controlled release of a therapeutic agent from the therapeutic region 106a, 106b in accordance with a predetermined dosage regimen. For example, in treating and/or managing postoperative pain, it may be desirable for the multi-region treatment portion to consistently release 50-400 mg/day of local anesthetic (e.g., bupivacaine, ropivacaine and the like) for at least 2-3 days following surgery (i.e., first dosage regimen) and then release a local anesthetic at a slower rate (e.g., 25-106 mg/day) for the next 5 to 10 days (i.e., second dosage regimen). In this exemplary embodiment, the first dosage region, and the control region and therapeutic region pair therein, would be sized, dimensioned, and configured such that the multi-region treatment portion releases the first therapeutic agent in a manner that is consistent with the prescribed first dosage regimen. Similarly, the second dosage region, and the control region and therapeutic region pair therein, would be sized, dimensioned and configured such that the multi-region treatment portion releases the second therapeutic agent in a manner that is consistent with the prescribed second dosage regimen. In another embodiment, the first and second dosage regions may correspond to dosage regimens utilizing different therapeutic agents. In one embodiment, the multi-region treatment portion 100 is configured to administer the first and second dosage regimens in sequence, simultaneously, or in an overlapping fashion to yield a complementary or synergistic benefit. In an alternate embodiment of this scenario, the first and second dosage regimens, respectively, may have no clinical association or relationship whatsoever. For example, as described above with respect to the embodiment depicted in FIG. 42, the first dosage regimen administered via the first dosage region may be treating or managing postoperative pain management and the second dosage regimen administered via the second dosage region may be treating or preventing infection of the surgical site or implanted prosthesis (if any).

Figure 44:
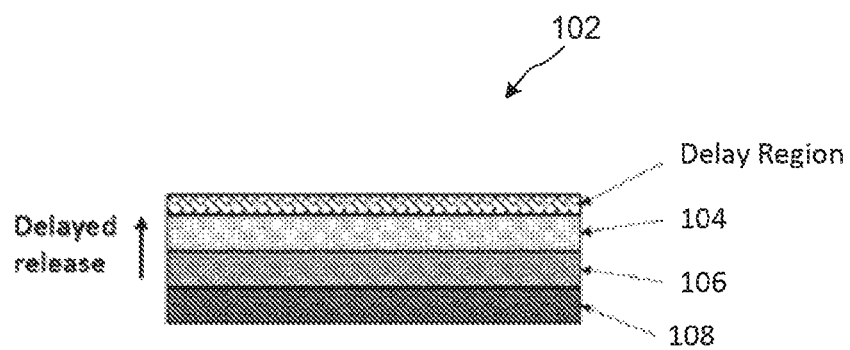

Certain embodiments of the present invention utilize delayed release agents. As illustrated in FIG. 44, the treatment portion 100 may include a delay region as the outermost (i.e., topmost) region to the multi-region treatment portion and adjacent to a control region 104 comprising a releasing agent. The delay region presents a barrier to physiologic fluids from reaching and dissolving the releasing agent within the control region. In one embodiment, the delay region may comprise a delayed release agent mixed with a bioresorbable polymer, but without a releasing agent. Delayed release agents are different from the releasing agents used in the multi-region treatment portion of the invention. Delayed release agents dissolve in physiological fluids more slowly than do releasing agents and thus provide the possibility for release of a therapeutic agent a defined amount of time following implantation of the multi-region treatment portion. In embodiments where a delayed release agent is not present in the delay region, it may take more time for the physiological fluids to traverse the delay region and contact the releasing agent. Only when the physiological fluids make contact with the control region will the releasing agent begin to dissolve, thus allowing the controlled release of the therapeutic agent. Delayed release agents may be advantageously used in the therapeutic methods of the invention wherein the therapeutic agent is not immediately required. For example, a nerve blocking agent may be injected prior to a surgical procedure, numbing the entire area around a surgical site. The controlled release of a local anesthetic is not required in such a surgery until the nerve block wears off.

Suitable delayed release agents for use in the present invention are pharmaceutically acceptable hydrophobic molecules such as fatty acid esters. Such esters include, but are not limited to, esters of myristoleic acid, sapienic acid, vaccenic acid, stearic acid, arachidic acid, palmitic acid, erucic acid, oleic acid, arachidonic acid, linoleic acid, linoelaidic acid, eicosapentaenoic acid, docosahexaenoic acid. Preferred esters include stearic acid methyl ester, oleic acid ethyl ester, and oleic acid methyl ester. Other suitable delayed release agents include tocopherol and esters of tocopherol, such as tocopheryl nicotinate and tocopheryl linolate.

Figure 45:
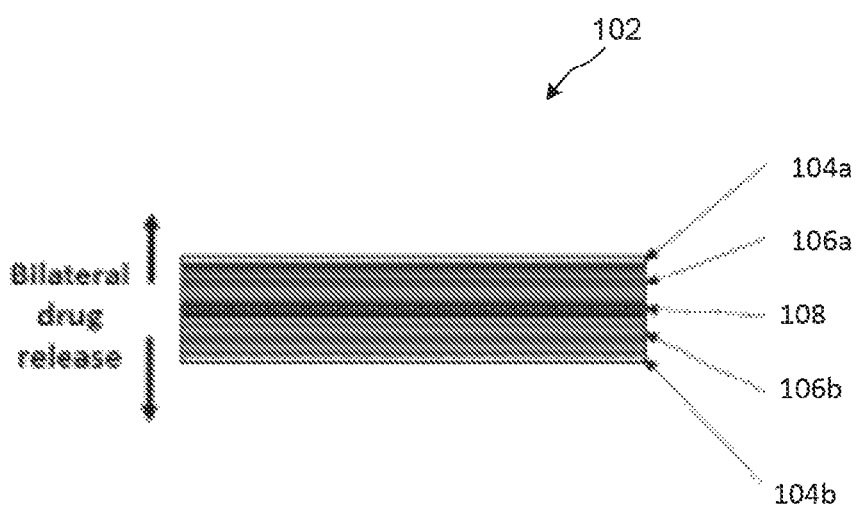

FIG. 45 shows another embodiment of a therapeutic member 102 comprising a treatment portion having bidirectional release of the chemotherapeutic agent. The therapeutic member 102 includes a base region 108 sandwiched between two therapeutic regions 106a, 106b, and two control regions 104a, 104b positioned outwardly (further from the base region 108) of the therapeutic regions 104a, 104b.

Figure 46:
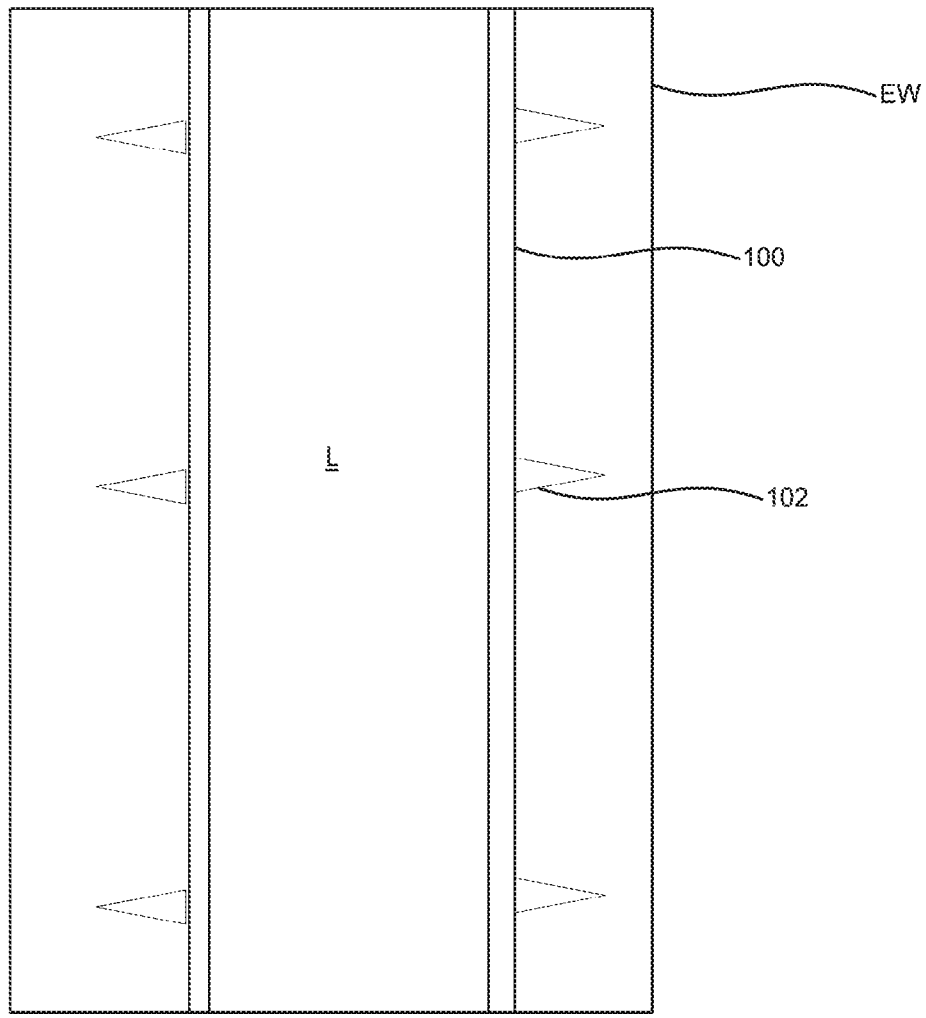
FIG. 46 is a cross-sectional side view of a treatment device implanted within a body lumen.

FIG. 46 is a cross-sectional side view of a treatment device 10 implanted within a body lumen. As demonstrated by FIG. 46, any of the treatment devices 10 disclosed herein may be configured for extraluminal administration of a chemotherapeutic agent, such as at a depth within the esophageal wall, including within different layers of esophageal tissue (i.e., within the mucosal layer, within the submucosal layer, and/or within the muscular layer, etc.) and/or between the different tissue layers of the esophageal wall (e.g., in an annular space between the mucosal layer and a submucosal layer, between a submucosal layer and a muscle layer, etc.). The treatment device 10 may be delivered intraluminally, as discussed above. To maximize the local delivery and potency of the chemotherapeutic agent, it may be desirable for the treatment device to be enabled to administer the chemotherapeutic agent within the tissue and/or the space between layers. Administration of the chemotherapeutic agent to or into the annular space between layers allow for the chemotherapeutic agent to remain locally, proximate to the tumor, rather than being lost down the esophagus. Additionally, administration to this annular space may provide greater, and more central, access to the tumor itself as opposed to intraluminal administration, which might only be directed at the outer regions of the tumor. Representative embodiments of this configuration include an anchoring member 100 having a therapeutic member 4600 that extends into the esophageal tissue, as shown in FIG. 46. More specifically, upon deployment of the anchoring member the therapeutic member is configured to pierce the mucosal layer such that the therapeutic member is positioned in or proximate to the annular space existing between the mucosal and submucosal layers and/or the submucosal and muscular layers of the esophagus. In some embodiments, the piercing creates a channel or opening that provides direct access to the space. Upon positioning proximate to or within the annular space, the therapeutic member is configured to administer a therapeutic dosage of chemotherapeutic agent into the annular space.

Figure 47:
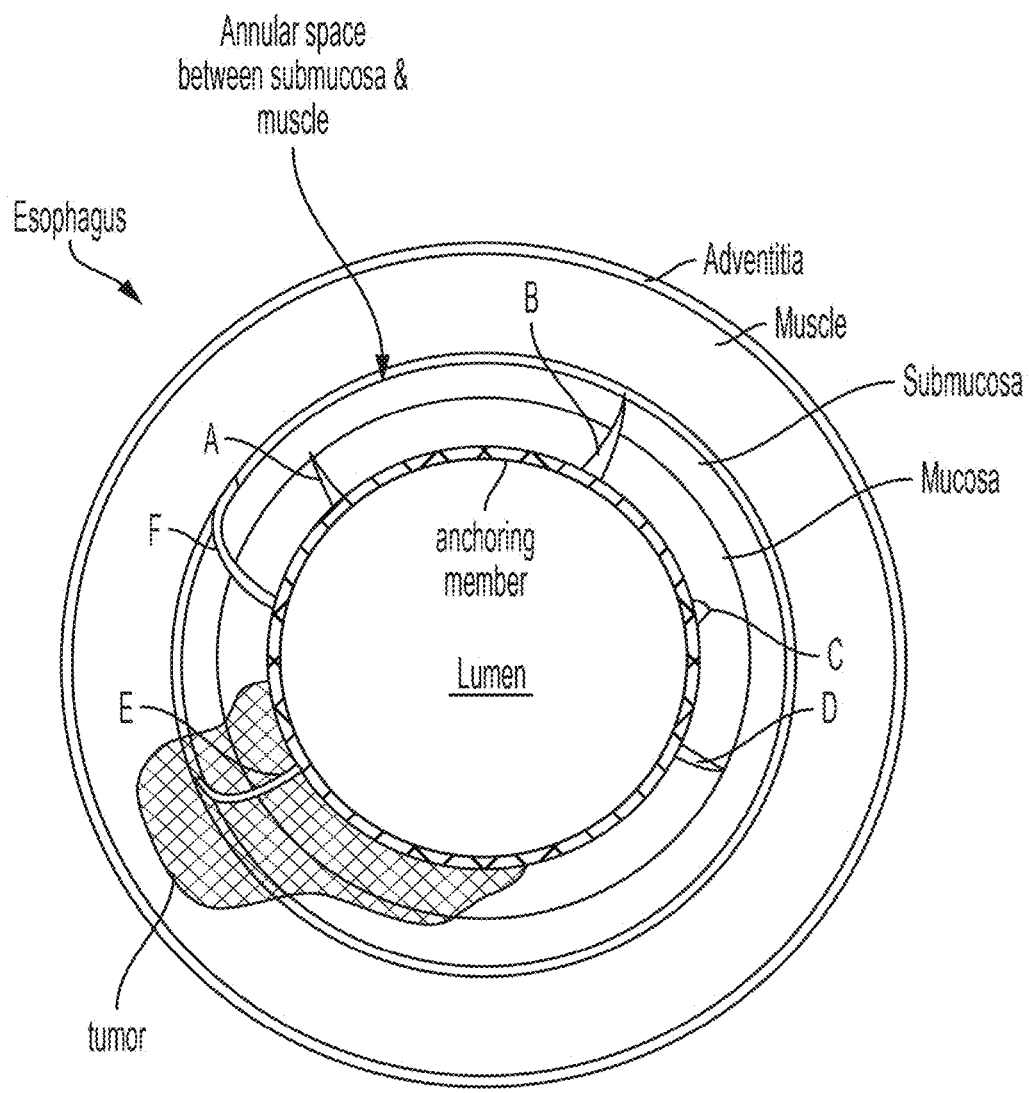
FIG. 47 is a cross-sectional end view showing multiple variations of a treatment device in accordance with the present technology.

FIG. 47 is a cross-sectional end view showing multiple variations of protruding portions and/or therapeutic members configured to access tissue within the interior portion of the esophageal wall. The treatment device 10, for example, may have one or more protruding portions protruding radially outwardly from an exterior portion of the anchoring member 100 and/or therapeutic member 102 that are configured to pierce or atraumatically gain access to an interior portion of the esophageal wall. In some embodiments, the therapeutic member is comprised of the protruding portion(s). The protruding portions may be positioned along all or portion of length of anchoring member and/or lumen, and/or along all or portion of circumference of the anchoring member and/or lumen. In some embodiments, the protruding portion(s) may be curved (e.g., F and E in FIG. 47), and some protruding portion(s) may be linear (e.g., A, B, C, D in FIG. 47). In some embodiments, the protruding portion(s) may comprise a flap with a sharp edge (e.g., E). When expanded the tip or leading edge of the protruding portion penetrates the esophageal wall tissue to a particular depth. In some embodiments, the anchoring member 100 and/or the therapeutic member 102 may be rotated to engage the tissue with the leading edge or tip of the protruding portion. Continued rotation of the anchoring member 100 and/or therapeutic member 102 may push the protruding portion through the tissue in a radial direction, both avoiding or reducing the likelihood of puncturing the muscular layer, but also to position more surface area of the protruding portion into the annular space.

The protruding portion(s) may access a range of depths within the esophageal wall. In some embodiments, different protruding portions on the same anchoring member and/or therapeutic member may access different depths. In some embodiments, the protruding portion(s) terminates within mucosal tissue (e.g., C). In some embodiments, the protruding portion(s) terminates at a depth within the esophageal wall between mucosal tissue and submucosal tissue (e.g., D). In some embodiments, the protruding portion(s) terminates within submucosal tissue (e.g., A). In some embodiments, the protruding portion(s) terminates at a depth within the esophageal wall between submucosal tissue and muscle tissue (e.g., F, E, B). In some embodiments, the protruding portion(s) terminates within muscle tissue. The protruding portion(s) may be configured to curve as it extends into the esophageal tissue. In some embodiments, the protruding portion(s) curves around at least a portion of an annular space between a submucosal layer and a muscle layer of the esophageal wall (e.g., F).

VI. Examples

The following examples are offered by way of illustration and not by way of limitation.

Example 1 shows the sustained release of paclitaxel in a multilayer film with varying amounts of releasing agent.

Multilayer films comprising paclitaxel with three different amounts of releasing agent were prepared according to the following procedures.

Preparation of bioresorbable polymer/drug films. A drug layer comprised of 438 mg poly(L-lactide-co-ε-caprolactone)(PLCL) (Corbion; Lenexa, KS) having a PLA to PCL ratio of from 90:10 to 60:40, 81 mg paclitaxel (Fujian South Pharmaceutical Co. Ltd; Fujian, People's Republic of China), Tween 20 (Sigma-Aldrich Pte Ltd; Singapore) and 7 g dichloromethane (DCM) (Merck; Kenilworth, NJ) was made by mixing the components thoroughly. One film was prepared with a Tween 20 to polymer ratio of 1:10 ("Normal Tween"), while another film was prepared with a ratio of 2:10 ("Double Tween"). An additional film was prepared without the addition of Tween 20 ("No Tween"). The resulting blends were poured onto a flat plate and drawn by a film applicator to form a thin film upon drying (<200 μm thickness). For each sample, a polymer base layer and a drug layer were aligned and compressed by a heat compressor at >60° C., 6 MPa for >50 seconds. The thin films were cut to form 2 cm×2 cm samples with overall film thickness <0.2 mm.

In vitro drug elution testing of paclitaxel multilayer films. The purpose of this procedure was to measure the release of paclitaxel from multilayer films into a receiving fluid consisting of 15% MeOH. The in vitro release procedure consisted of placing a known size of film into an apparatus containing the receiving fluid. The in vitro release apparatus consisted of either a 20 ml or a 100 ml glass bottle. A receiving fluid in the amount of either 12 ml or 50 ml was added to each sample bottle. During the release study, the apparatus was placed in a water bath maintained at 37±2° C. At predetermined intervals, samples of the receiving fluid were removed and analyzed for paclitaxel concentration by UV-Vis Spectrophotometer.

Figure 48:
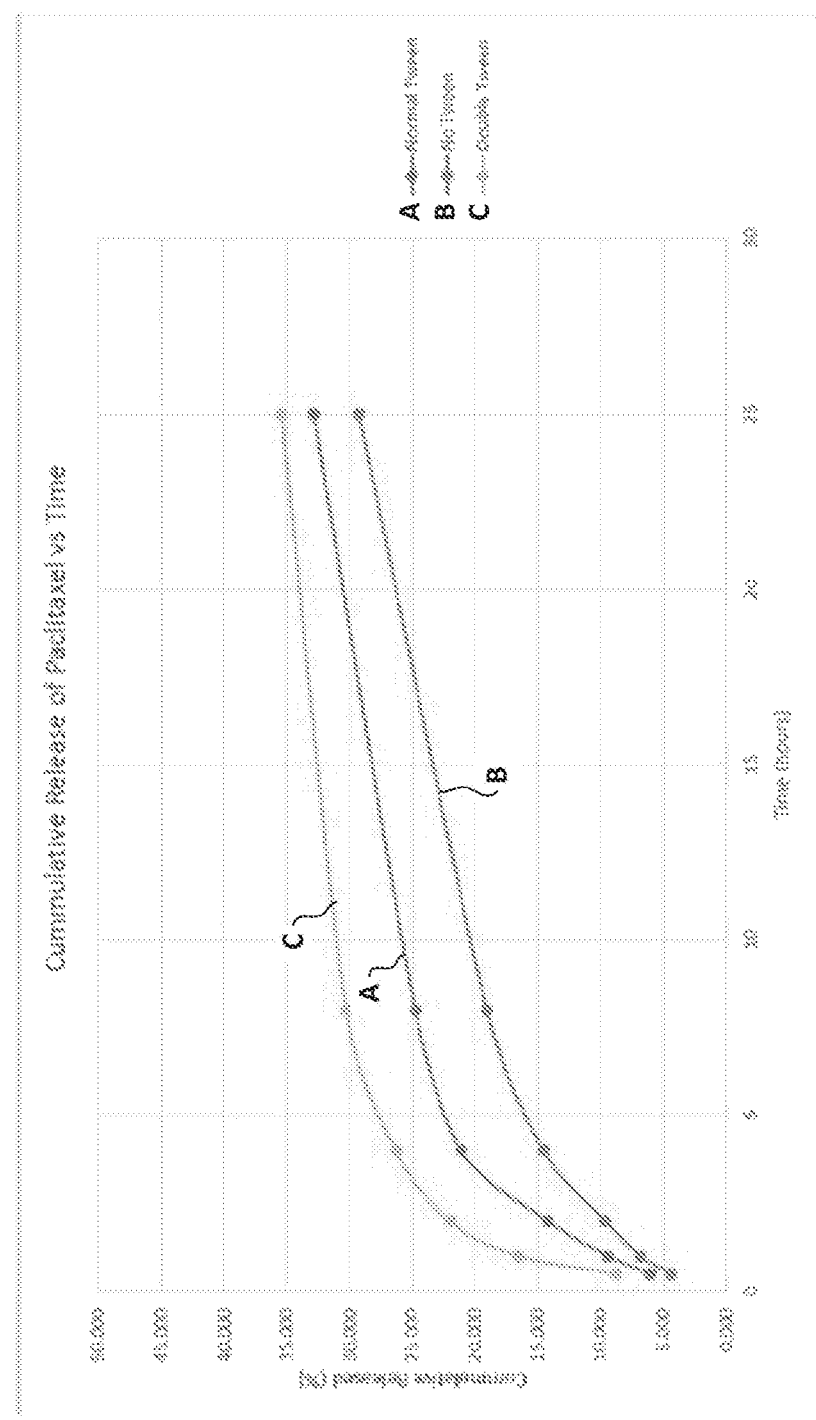
FIGS. 48-51B are graphs showing elution profiles for different treatment portion configurations in accordance with the present technology.

Elution profile. FIG. 48 shows the cumulative release profiles of these paclitaxel films. The results show the effect of the use of different amounts of releasing agent Tween 20 in the therapeutic agent layer. The sample containing no Tween 20 had the slowest rate of release of drug (No Tween). The rate of release increased as the amount of Tween 20 increased (Normal Tween and Double Tween).

Figure 49A:
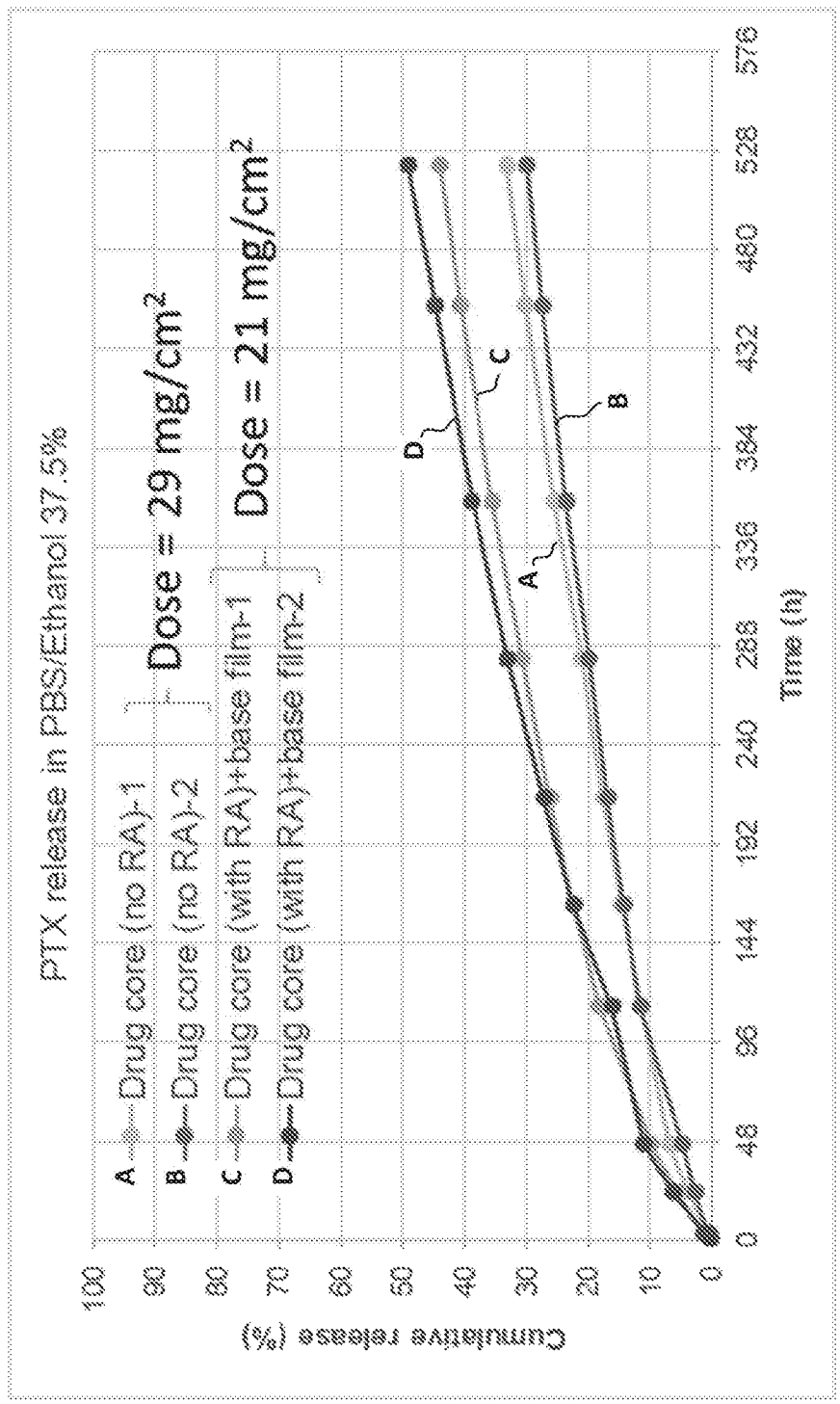
Figure 49B:
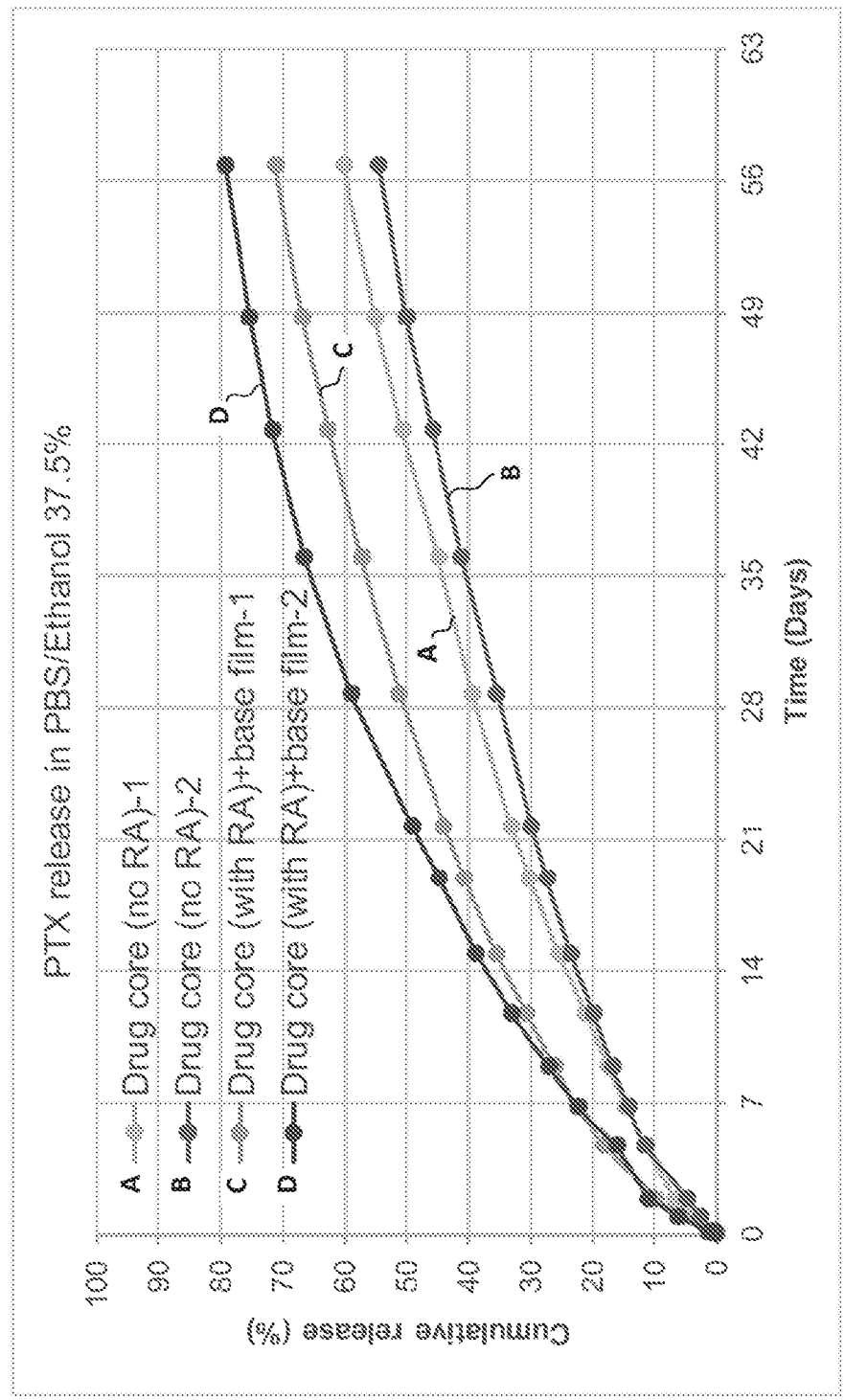

Examples 2 and 3 are shown in FIGS. 49A and 49B, respectively, and show elution profiles of treatment portions of the present technology with different therapeutic regions ("drug core") having different amounts of releasing agent ("RA"), and with different numbers of base regions. The therapeutic regions included paclitaxel at different dosages.

Figure 50:
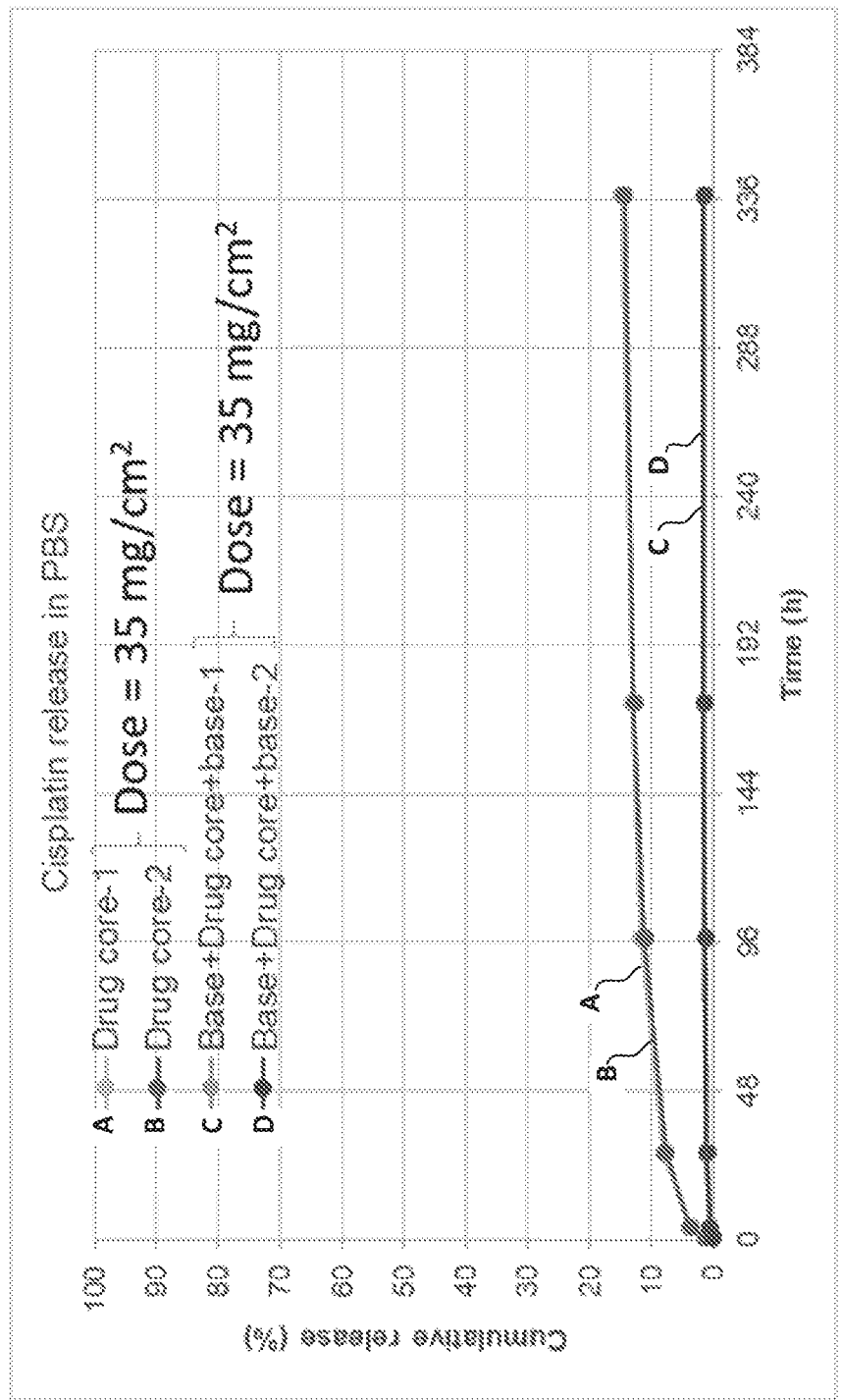

Example 4 is shown at FIG. 50, and show elution profiles of treatment portions of the present technology with different therapeutic regions ("drug core") having different amounts of releasing agent ("RA"). The therapeutic regions included cisplatin at different dosages.

Figure 51A:
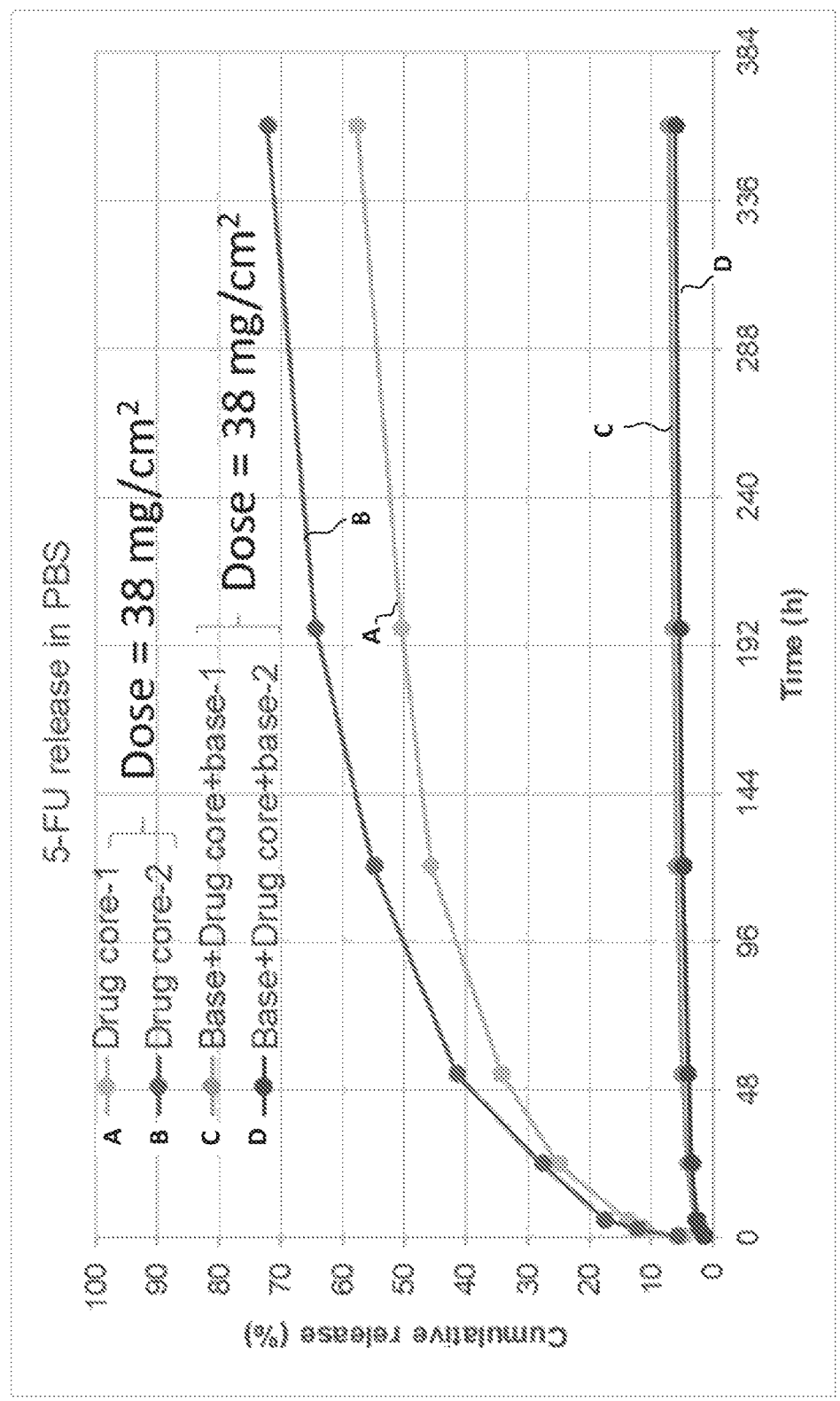
Figure 51B:
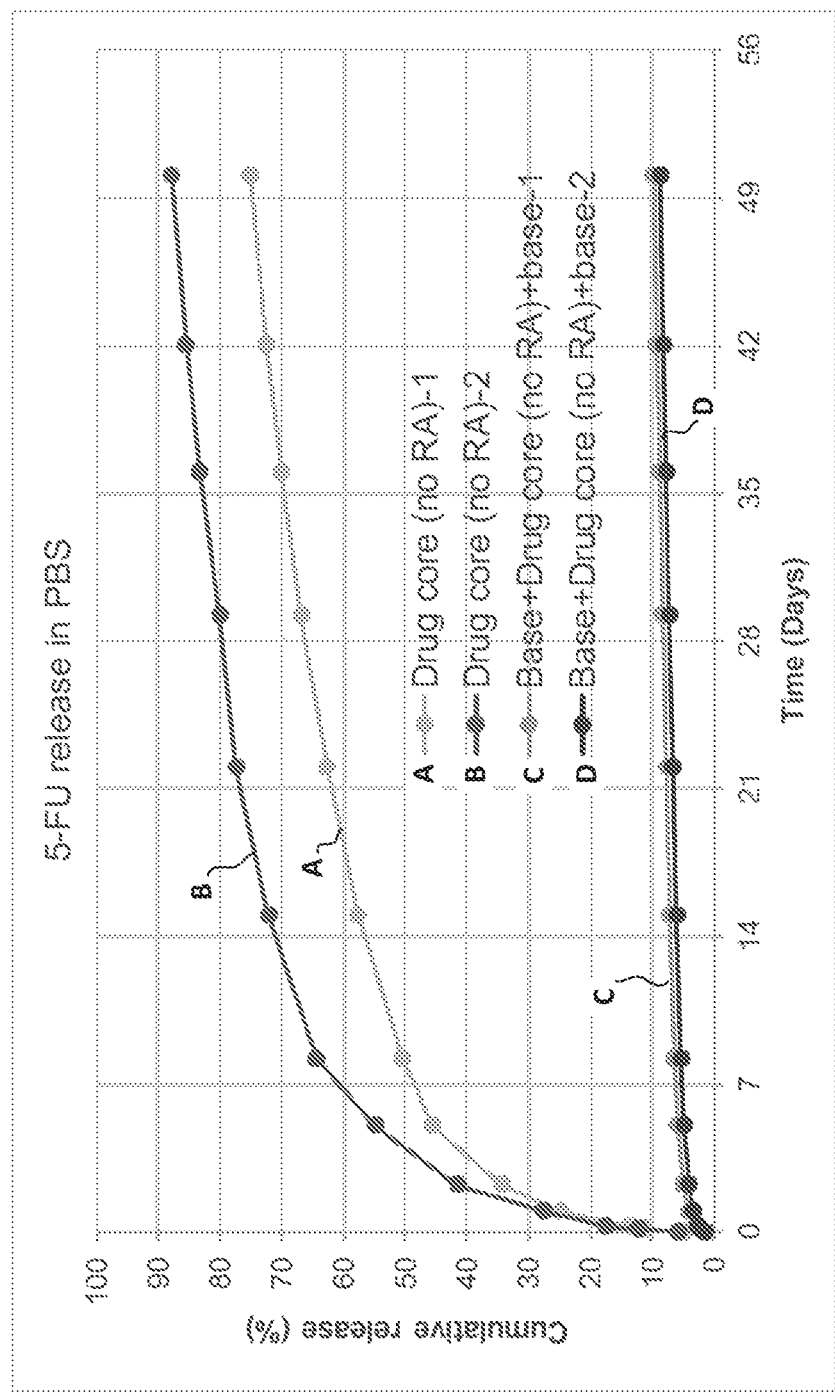

Examples 5 and 6 are shown in FIGS. 51A and 51B, respectively, and show elution profiles of treatment portions of the present technology with different therapeutic regions ("drug core") having different amounts of releasing agent ("RA"), and with different numbers of base regions. The therapeutic regions included 5-FU at different dosages.

VII. Conclusion

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for treating a patient with a cancerous tumor within a body lumen, the system comprising:
   an implant configured for endoluminal placement via a delivery system into the body lumen of the patient, the implant having a longitudinal axis, and wherein the implant comprises:
      a therapeutic member comprising a treatment portion for controlled release of a chemotherapeutic agent, the treatment portion comprising:
         a therapeutic region comprising the chemotherapeutic agent, a first bioresorbable polymer and a releasing agent, wherein the chemotherapeutic agent, the first bioresorbable polymer, and the releasing agent are mixed together, wherein the therapeutic region has first and second longitudinal ends, and wherein the releasing agent is configured to dissolve when the therapeutic member is placed in vivo to form channels in the therapeutic region, and
         a substantially impermeable base region having a first portion and a second portion integral with the first portion, the first portion adjacent the therapeutic region along the longitudinal axis of the implant and the second portion extending radially over one or both of the first and second longitudinal ends of the therapeutic region, wherein the base region comprises a second bioresorbable polymer,
      wherein the treatment portion releases the chemotherapeutic agent in a direction away from the substantially impermeable base region; and
   a metallic anchoring member configured to provide structural support for the therapeutic member following endoluminal placement of the implant,
   wherein the anchoring member radially surrounds the therapeutic member such that the anchoring member is positioned between the therapeutic member and the treatment site, and
   wherein the therapeutic member extends around only a portion of the inner circumference of the anchoring member and is configured to administer a therapeutically effective dose to the treatment site through one or more openings in the metallic anchoring member for a sustained period following endoluminal placement of the implant in the body lumen of the patient.

2. The system of claim 1, wherein the body lumen is an esophagus.

3. The system of claim 1, wherein the body lumen is a portion of the gastrointestinal tract.

4. The system of claim 1, wherein the anchoring member is a stent having sufficient radial resistance to provide structural integrity to the body lumen.

5. The system of claim 1, wherein the anchoring member is configured to prevent and/or slow penetration of the tumor into the lumen.

* * * * *